US011179286B2

(12) United States Patent
Freeman et al.

(10) Patent No.: US 11,179,286 B2
(45) Date of Patent: Nov. 23, 2021

(54) ADAPTIVE BODY POSITIONING

(71) Applicant: ZOLL Medical Corporation, Chelmsford, MA (US)

(72) Inventors: Gary A Freeman, Waltham, MA (US); Ulrich Herken, Medford, MA (US); Christopher L Kaufman, Somerville, MA (US); Nikhil S Joshi, San Jose, CA (US)

(73) Assignee: ZOLL Medical Corporation, Chelmsford, MA (US)

( * ) Notice: Subject to any disclaimer, the term of this patent is extended or adjusted under 35 U.S.C. 154(b) by 544 days.

(21) Appl. No.: 15/787,735

(22) Filed: Oct. 19, 2017

(65) Prior Publication Data

US 2018/0110667 A1   Apr. 26, 2018

Related U.S. Application Data

(60) Provisional application No. 62/411,062, filed on Oct. 21, 2016.

(51) Int. Cl.
*A61G 13/08* (2006.01)
*A61G 15/02* (2006.01)
(Continued)

(52) U.S. Cl.
CPC ............ *A61G 13/08* (2013.01); *A61B 5/4836* (2013.01); *A61B 5/6891* (2013.01); *A61G 1/04* (2013.01);
(Continued)

(58) Field of Classification Search
CPC ...... A61G 13/08; A61G 13/04; A61G 13/121; A61G 1/04; A61G 7/005; A61G 7/015;
(Continued)

(56) References Cited

U.S. PATENT DOCUMENTS 3,804,082 A   4/1974 Tarjan
3,870,038 A   3/1975 Arblaster
(Continued)

FOREIGN PATENT DOCUMENTS

CN   201346293 Y   11/2009
CN   201437005 U    4/2010
(Continued)

*Primary Examiner* — Nicholas F Polito
*Assistant Examiner* — Morgan J McClure
(74) *Attorney, Agent, or Firm* — Zoll Medical Corporation

(57) ABSTRACT

A patient support structure for assisting cardiopulmonary resuscitation (CPR) treatment of a patient is described. The patient support structure includes a base frame, one or more patient support sections supported by the base frame, at least one tilt adjuster coupled to at least one of the patient support sections and configured to tilt the at least one of the patient support sections, around a transverse axis of the patient support structure, to a tilt angle, and a chest compression (CC) device mount disposed on at least one of the patient support sections and configured to adjustably secure a CC device to the patient support structure. The tilt angle may be a target tilt angle and the patient support structure may further include a processor configured to determine the target tilt angle based on at least one of sensor input and user input.

31 Claims, 27 Drawing Sheets

(51) Int. Cl.

| | |
|---|---|
| *A61H 31/00* | (2006.01) |
| *A61G 13/12* | (2006.01) |
| *A61G 7/005* | (2006.01) |
| *A61B 5/00* | (2006.01) |
| *A61G 7/015* | (2006.01) |
| *A61G 7/05* | (2006.01) |
| *A61G 1/04* | (2006.01) |
| *A61G 13/04* | (2006.01) |
| *A61G 7/07* | (2006.01) |
| *A61G 15/12* | (2006.01) |
| *A61B 5/107* | (2006.01) |
| *A61B 5/11* | (2006.01) |
| *A61B 5/316* | (2021.01) |
| *A61B 5/318* | (2021.01) |

(52) U.S. Cl.
CPC ............ *A61G 7/005* (2013.01); *A61G 7/015* (2013.01); *A61G 7/05* (2013.01); *A61G 7/072* (2013.01); *A61G 13/04* (2013.01); *A61G 13/121* (2013.01); *A61G 15/02* (2013.01); *A61H 31/00* (2013.01); *A61H 31/006* (2013.01); *A61H 31/008* (2013.01); *A61B 5/1071* (2013.01); *A61B 5/1116* (2013.01); *A61B 5/316* (2021.01); *A61B 5/318* (2021.01); *A61B 2505/01* (2013.01); *A61G 15/12* (2013.01); *A61G 2203/22* (2013.01); *A61G 2203/42* (2013.01); *A61G 2210/30* (2013.01)

(58) Field of Classification Search
CPC .......... A61G 7/05; A61G 7/072; A61G 15/02; A61G 15/12; A61G 2203/22; A61G 2203/42; A61G 2210/30; A61B 5/4836; A61B 5/6891; A61B 5/04012; A61B 5/0402; A61B 5/1071; A61B 5/1116; A61B 2505/01; A61H 31/00; A61H 31/006; A61H 31/008; A47C 20/04; A47C 20/041

See application file for complete search history.

(56) References Cited

U.S. PATENT DOCUMENTS

| | | | |
|---|---|---|---|
| 4,019,501 A | 4/1977 | Harris | |
| 4,077,400 A | 3/1978 | Harrigan | |
| 4,095,590 A | 6/1978 | Harrigan | |
| 4,398,313 A | 8/1983 | Mitchell | |
| 4,588,383 A | 5/1986 | Parker | |
| 4,610,254 A | 9/1986 | Morgan | |
| 4,770,164 A | 9/1988 | Lach et al. | |
| 4,863,385 A | 9/1989 | Pierce | |
| 4,928,674 A | 5/1990 | Halperin et al. | |
| 5,137,458 A | 8/1992 | Ungs | |
| 5,285,792 A | 2/1994 | Sjoquist | |
| 5,402,884 A | 4/1995 | Gilman | |
| 5,496,257 A | 3/1996 | Kelly | |
| 5,579,919 A | 12/1996 | Gilman | |
| 5,645,571 A | 7/1997 | Olson | |
| 5,662,690 A | 9/1997 | Cole | |
| 5,697,955 A | 12/1997 | Stolte | |
| 5,700,281 A | 12/1997 | Brewer | |
| 5,720,059 A | 2/1998 | Allevato et al. | |
| 5,738,637 A | 4/1998 | Kelly et al. | |
| 5,792,190 A | 8/1998 | Olson | |
| 5,797,969 A | 8/1998 | Olson | |
| 5,853,292 A | 12/1998 | Eggert | |
| 5,913,685 A | 6/1999 | Hutchins | |
| 5,955,956 A | 9/1999 | Stendahl | |
| 6,066,106 A | 5/2000 | Sherman et al. | |
| 6,083,246 A | 7/2000 | Stendahl | |
| 6,101,413 A | 8/2000 | Olson | |
| 6,125,299 A | 9/2000 | Groenke | |
| 6,142,962 A | 11/2000 | Mollenauer et al. | |
| 6,213,960 B1 | 4/2001 | Sherman et al. | |
| 6,282,736 B1* | 9/2001 | Hand | A61B 6/0428 5/600 |
| 6,306,107 B1 | 10/2001 | Myklebust | |
| 6,334,070 B1 | 12/2001 | Nova | |
| 6,356,785 B1 | 3/2002 | Snyder | |
| 6,370,428 B1 | 4/2002 | Snyder | |
| 6,390,996 B1 | 5/2002 | Halperin | |
| 6,398,745 B1 | 6/2002 | Sherman et al. | |
| 6,405,082 B1 | 6/2002 | Borgenicht | |
| 6,616,620 B2 | 9/2003 | Sherman et al. | |
| 6,690,616 B1 | 2/2004 | Bahr et al. | |
| 6,697,671 B1 | 2/2004 | Nova | |
| 6,768,922 B2 | 7/2004 | Faller | |
| 6,827,695 B2 | 12/2004 | Palazzolo | |
| 6,952,605 B1 | 10/2005 | Scarberry | |
| 7,108,665 B2 | 9/2006 | Halperin et al. | |
| 7,127,758 B2 | 10/2006 | Gabbay | |
| 7,220,235 B2 | 5/2007 | Geheb et al. | |
| 7,270,639 B2 | 9/2007 | Jensen et al. | |
| 7,347,832 B2 | 3/2008 | Jensen et al. | |
| 7,354,407 B2 | 4/2008 | Quintana et al. | |
| RE40,471 E | 8/2008 | Groenke | |
| 7,429,250 B2 | 9/2008 | Halperin et al. | |
| 7,546,651 B2 | 6/2009 | Groteke | |
| 7,569,021 B2 | 8/2009 | Sebelius et al. | |
| 7,602,301 B1 | 10/2009 | Stirling et al. | |
| 7,706,878 B2 | 4/2010 | Freeman | |
| 7,729,757 B2 | 6/2010 | Parascandola | |
| 7,908,691 B2 | 3/2011 | Small | |
| 8,336,142 B1 | 12/2012 | See | |
| 8,397,326 B2* | 3/2013 | Lafleche | A61G 7/05761 5/713 |
| 8,511,308 B2 | 8/2013 | Hecox | |
| 8,572,778 B2* | 11/2013 | Newkirk | G06F 3/04842 5/600 |
| 8,717,181 B2* | 5/2014 | Tallent | G08B 25/008 340/573.4 |
| 8,795,209 B2 | 8/2014 | Herken | |
| 9,248,062 B2* | 2/2016 | Valentino | A61G 1/0256 |
| 9,750,661 B2* | 9/2017 | Lurie | A61G 13/1215 |
| 9,801,782 B2* | 10/2017 | Lurie | A61H 31/005 |
| 10,245,209 B2* | 4/2019 | Lurie | A61H 31/004 |
| 10,596,064 B2* | 3/2020 | Kaufman | A61H 31/006 |
| 2001/0011159 A1 | 8/2001 | Cantrell et al. | |
| 2001/0047140 A1 | 11/2001 | Freeman | |
| 2002/0007832 A1 | 1/2002 | Doherty | |
| 2002/0147534 A1 | 10/2002 | Delcheccolo et al. | |
| 2003/0004547 A1 | 1/2003 | Owen | |
| 2003/0036044 A1 | 2/2003 | Pastrick | |
| 2003/0040775 A1 | 2/2003 | Faller | |
| 2003/0055458 A1 | 3/2003 | Hamilton | |
| 2003/0083699 A1 | 5/2003 | Hamilton | |
| 2003/0100852 A1 | 5/2003 | Palmer et al. | |
| 2003/0216785 A1 | 11/2003 | Edwards | |
| 2004/0030272 A1 | 2/2004 | Kelly et al. | |
| 2004/0082888 A1 | 4/2004 | Palazzolo | |
| 2005/0070964 A1 | 3/2005 | Hansen | |
| 2010/0022904 A1 | 1/2010 | Centen | |
| 2011/0092864 A1 | 4/2011 | Woerlee et al. | |
| 2012/0083720 A1 | 4/2012 | Canten et al. | |
| 2013/0218055 A1 | 8/2013 | Fossan | |
| 2013/0231593 A1 | 9/2013 | Yannopoulos et al. | |
| 2014/0171840 A1 | 6/2014 | Aelen | |
| 2014/0276269 A1* | 9/2014 | Illindala | A61H 31/006 601/41 |
| 2014/0309564 A1* | 10/2014 | Jensen | A61H 31/006 601/41 |
| 2015/0047646 A1 | 2/2015 | Marinkovic | |
| 2015/0057580 A1* | 2/2015 | Illindala | A61H 31/006 601/41 |
| 2015/0231026 A1 | 8/2015 | Lurie | |
| 2015/0265793 A1 | 9/2015 | Davis | |
| 2015/0351982 A1* | 12/2015 | Krenik | A47C 23/06 5/616 |
| 2015/0352367 A1 | 12/2015 | Quan et al. | |
| 2016/0058660 A1 | 3/2016 | Lurie et al. | |

(56) References Cited

U.S. PATENT DOCUMENTS

| | | | |
|---|---|---|---|
| 2016/0128899 A1 | 5/2016 | Lurie et al. | |
| 2016/0135706 A1 | 5/2016 | Sullivan et al. | |
| 2016/0158098 A1 | 6/2016 | Paradis et al. | |
| 2016/0193095 A1* | 7/2016 | Roussy | A61G 7/002 5/11 |
| 2016/0338904 A1* | 11/2016 | Lurie | A61G 13/129 |

FOREIGN PATENT DOCUMENTS

| | | |
|---|---|---|
| CN | 102106779 A | 6/2011 |
| CN | 102164573 A | 8/2011 |
| CN | 202078515 | 12/2011 |
| JP | 2000176025 | 6/2000 |
| JP | 2002514107 | 5/2002 |
| JP | 2002360711 | 12/2002 |
| JP | 2003525712 | 9/2003 |
| WO | 2000027334 A2 | 5/2000 |
| WO | 2002091905 | 11/2002 |
| WO | 2003024521 | 3/2003 |
| WO | 2004112683 A1 | 12/2004 |
| WO | 2005037179 A1 | 4/2005 |
| WO | 20122001541 A1 | 1/2012 |

\* cited by examiner

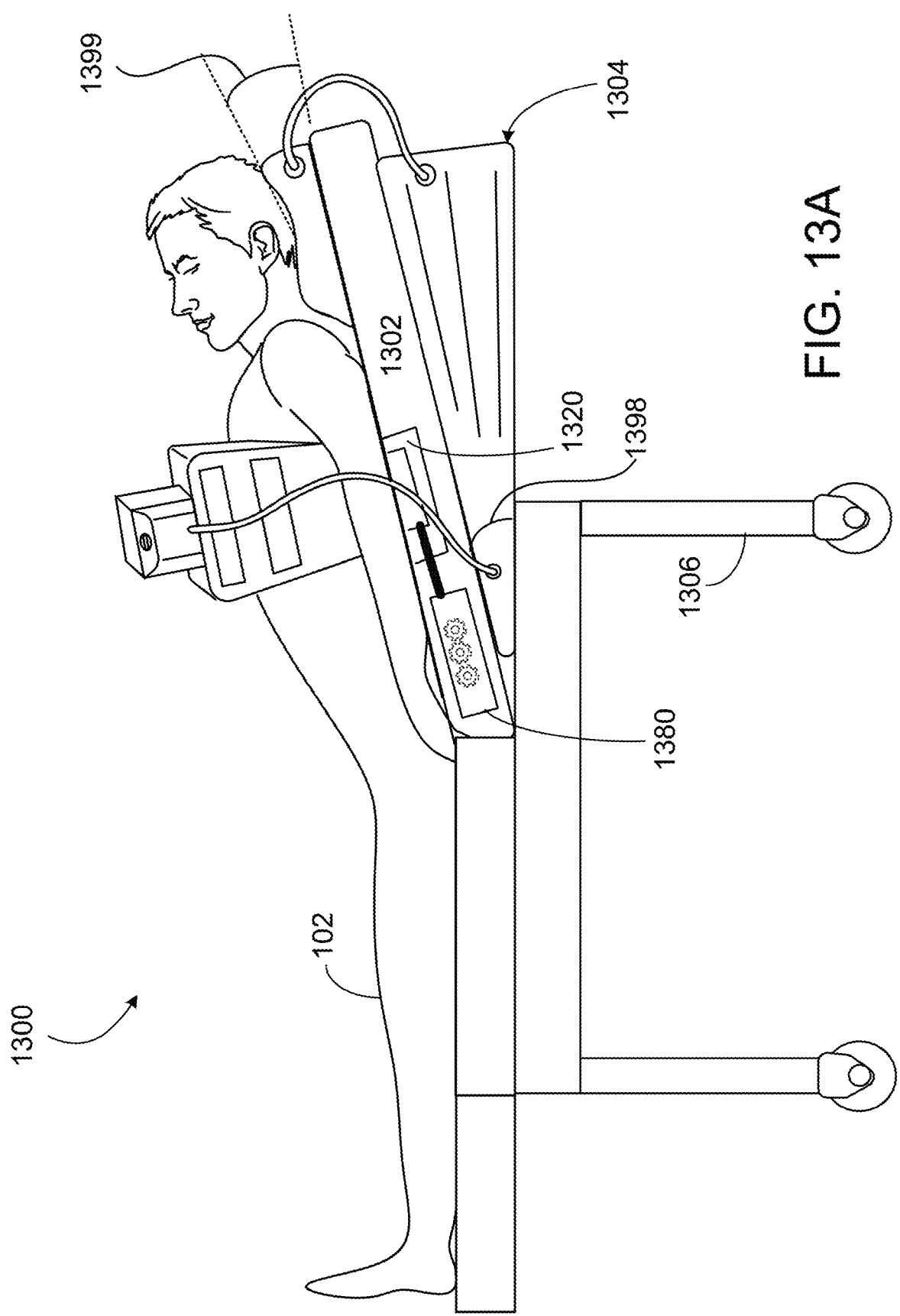

ADAPTIVE BODY POSITIONING

CROSS-REFERENCE TO RELATED APPLICATIONS

This application claims the benefit under 35 U.S.C. § 119(e) of U.S. Provisional Application No. 62/411,062 filed Oct. 21, 2016. All subject matter set forth in the above referenced application is hereby incorporated by reference in its entirety into the present application as if fully set forth herein.

BACKGROUND

Acute care is delivered to patients in emergency situations in the pre-hospital and hospital settings for patients experiencing a variety of acute medical conditions involving the timely diagnosis and treatment of disease states that, left alone, will likely degenerate into a life-threatening condition and, potentially, death within a period of 72 hours or less. Stroke, dyspnea (difficulty breathing), traumatic arrest, myocardial infarction and cardiac arrest are a few examples of disease states for which acute care is delivered to patients in an emergency setting. Acute care comprises different treatment and/or diagnosis, depending upon the disease state. Cardiac arrest is one example that highlights critical interactions between the heart and the brain, and it remains a leading cause of death. Other examples include shock, traumatic brain injury, dehydration, kidney failure, congestive heart failure, wound healing, diabetes, stroke, respiratory failure, and orthostatic hypotension.

Despite advances in the field of circulatory enhancement, the need for improved approaches for treating patients with impaired circulation remains an important medical challenge. One example of acute care is cardio-pulmonary resuscitation (CPR), which is a process by which one or more care providers may attempt to resuscitate a patient who may have suffered an adverse cardiac event by taking one or more actions, for example, providing chest compressions and ventilation to the patient. During the first five to eight minutes after CPR efforts begin, chest compressions are an important element of CPR because chest compressions help maintain blood circulation through the body and in the heart itself. Evidence indicates that promptly re-establishing systemic blood flow and thereby maintaining threshold levels of coronary and cerebral perfusion may increase the success of the CPR treatment.

SUMMARY

An example of a patient support structure for assisting cardiopulmonary resuscitation (CPR) treatment of a patient according to the disclosure includes a base frame, one or more patient support sections wherein at least one of the one or more patient support sections is coupled to and supported by the base frame, at least one tilt adjuster coupled to at least one of the one or more patient support sections and configured to tilt the at least one of the one or more patient support sections, around a transverse axis of the patient support structure, to a tilt angle, and a chest compression (CC) device mount disposed on at least one of the one or more patient support sections and configured to adjustably secure a CC device to the patient support structure.

Implementations of such a patient support structure may include one or more of the following features. The CC device mount may be configured to couple to a complementary mounting structure of the CC device. The CC device mount may be configured to secure the CC device to the patient support structure without coupling to a complementary mounting structure on the CC device. The patient support structure may include an alignment feature wherein the alignment feature comprises one or more indicators of a position of an anatomical reference point of the patient that will align the patient with the CC device when the CC device is secured to the patient support structure. The one or more indicators may include one or more of a bump, a protrusion, a marking, a divot, and a lighted indicator. The patient support structure may include a manual position adjuster configured for manual adjustment of a position of the CC device relative to the patient support structure. The patient support structure may include an automated position adjuster configured to automatically adjust a position of the CC device relative to the patient support structure. The automated position adjuster may be configured to automatically adjust the position of the CC device in response to a control signal from one or more of a tilt controller disposed in the patient support structure a defibrillator, the CC device, and a computing device. The tilt angle may be a first tilt angle and the at least one tilt adjuster may be configured to adjust the at least one of the one or more patient support sections to a second tilt angle during CPR treatment. The automated position adjuster may be configured to automatically adjust the position of the CC device based on the adjustment of the tilt angle. The one or more patient support sections may include a first patient support section configured to support an upper body of the patient. The at least one tilt adjuster may be configured to tilt the first patient support section to the tilt angle. The patient support structure may include one or more angle indicators configured to indicate the tilt angle. The one or more angle indicators may include electronic angle indicators and mechanical angle indicators. The one or more angle indicators may include a marker that indicates one or more of a target angle and a target angular range. The patient support structure may include one or more accelerometers and the one or more angle indicators may be configured to display angles determined based on an accelerometer signal. The at least one tilt adjuster may be a manual tilt adjuster configured to tilt the at least one of the one or more patient support sections in response to manipulation of the manual tilt adjuster by a care provider. The at least one tilt adjuster may be an automated tilt adjuster configured to tilt the at least one of the one or more patient support sections in response to a control signal from one or more of a tilt controller disposed in the patient support structure, a defibrillator, the CC device, and a computing device. The patient support structure may be at least one of a bed, stretcher, litter, cot, gurney, a stretcher chair, and a pram. The patient support structure may include two or more patient support sections, and a spacer pivotally coupled to the at least two patient support sections and configured to elevate one of the two or more patient support sections relative to another of the two or more patient support sections. The at least one tilt adjuster may be configured to tilt a first patient support section configured to support the legs of the patient to a first tilt angle and to tilt a second patient support section configured to support the thorax of the patient to a second tilt angle. The at least one tilt adjuster may be configured to tilt the first patient support section up relative to the top of the base frame and to tilt the first patient support section down relative to the top of the base frame. The patient support structure may include an adjustable head support mechanically coupled to one of the one or more patient support sections via a mechanical coupling configured to enable movement of the adjustable head support from a stowed position to a head support position.

An example of a patient support structure for assisting cardiopulmonary resuscitation (CPR) treatment of a patient according to the disclosure includes a base frame, one or more patient support sections wherein at least one of the one or more patient support sections is coupled to and supported by the base frame, at least one tilt adjuster coupled to at least one of the one or more patient support sections and configured to tilt the at least one of the one or more patient support sections, around a transverse axis of the patient support structure, to a target tilt angle, and a processor configured to determine the target tilt angle based on at least one of sensor input and user input.

Implementations of such a patient support structure may include one or more of the following features. The patient support structure may include a tilt controller that includes an input device, wherein the user input is a tilt angle provided to the input device of the tilt controller. The sensor input may include one or more accelerometer signals indicative of one or more current tilt angles of the one or more patient support sections. The target tilt angle may be between approximately 0 and 40 degrees. The target tilt angle may be between approximately 0 and 30 degrees. The target tilt angle may be between approximately 10 and 30 degrees. The target tilt angle may be between approximately 10 and 20 degrees. The target tilt angle may be between approximately 20 and 30 degrees. The target tilt angle may be between approximately 25 and 30 degrees. The target tilt angle may be between approximately 20 and 25 degrees. The patient support structure may include a user interface and the processor may be further configured to provide the target tilt angle to the user interface. The user interface may include a display configured to display the target tilt angle. The processor may be further configured to provide a target tilt angle range to the user interface. The user interface may be a display configured to display the target tilt angle range. The processor may be further configured to provide the target tilt angle to one or more of a defibrillator, a CC device, and a computing device via a communicative connection between the processor and the one or more of the defibrillator, the CC device, and the computing device. The patient support structure may include an automated tilt adjuster and the processor may be further configured to provide a control signal indicative of the target tilt angle to the automated tilt adjuster. The automated tilt adjuster may be configured to automatically tilt at least one of the one or more patient support sections to the target tilt angle in response to the control signal from the processor. The patient support structure may include one or more angle indicators configured to indicate a current tilt angle of the one or more patient support sections. The one or more angle indicators may be coupled to an alarm configured to emit an alarm signal if the current tilt angle does not correspond to the target tilt angle. The processor may include a tilt angle module configured to determine the target tilt angle based on a physiological parameter of the patient. The processor may be configured to receive sensor input indicative of the physiological parameter of the patient. The processor may be configured to receive the sensor input from one or more of electrodes, a chest compression sensor, a motion sensor, and an optical sensor. The optical sensor may be a near infrared spectroscopy (NIRS) sensor. The processor may include a tilt angle module configured to determine the target tilt angle based on a physiological phase of the patient. The physiological phase of the patient may include one or more of a return of spontaneous circulation (ROSC) phase, a cardiac event, a respiratory event, an electrical phase, a metabolic phase, and a circulatory phase. The processor may include a tilt angle module configured to determine the target tilt angle based on a phase of CPR treatment. The phase of CPR treatment may include one or more of an elapsed time of CPR treatment, a number of delivered CPR compressions, a number of delivered CPR ventilations, a number of delivered defibrillation shocks, and an interval within a compression cycle. The patient support structure may be at least one of a bed, stretcher, litter, cot, gurney, a stretcher chair, and a pram. The patient support structure may include two or more patient support sections, and a spacer pivotally coupled to the two or more patient support sections and configured to elevate one of the two or more patient support sections relative to another of the two or more patient support sections. The at least one tilt adjuster may be configured to tilt a first patient support section configured to support the legs of the patient to a first tilt angle and to tilt a second patient support section configured to support the thorax of the patient to a second tilt angle. The at least one tilt adjuster may be configured to tilt the first patient support section up relative to the top of the base frame and to tilt the first patient support section down relative to the top of the base frame. The patient support structure may include an adjustable head support mechanically coupled to one of the one or more patient support sections via a mechanical coupling configured to enable movement of the adjustable head support from a stowed position to a head support position.

An example of a patient support structure for assisting cardiopulmonary resuscitation (CPR) treatment of a patient according to the disclosure includes a base frame, two or more patient support sections wherein at least one of the two or more patient support sections is coupled to and supported by the base frame, and a spacer pivotally coupled to the two or more patient support sections and configured to elevate one of the two or more patient support sections relative to another of the two or more patient support sections.

Implementations of such a patient support structure may include one or more of the following features. A first patient support section of the two or more patient support sections may be configured to support the head of the patient and a second patient support section of the two or more patient support sections may be configured to support the torso of the patient. The spacer may be configured to elevate the first patient support section relative to one the second patient support section such that a distance between the first patient support section and the base frame approximately 2 to 50 cm. The spacer may be configured to elevate the first patient support section relative to one the second patient support section such that a distance between the first patient support section and the base frame approximately 2 to 50 cm. The patient support structure may include at least one tilt adjuster coupled to at least one of the two or more patient support sections and configured to tilt the at least one of the two or more patient support sections, around a transverse axis of the patient support structure, to a tilt angle. The patient support structure may include a processor configured to determine the tilt angle based on at least one of sensor input and user input. The target tilt angle may be between approximately 0 and 40 degrees. The target tilt angle may be between approximately 0 and 30 degrees. The target tilt angle may be between approximately 10 and 30 degrees. The target tilt angle may be between approximately 10 and 20 degrees. The target tilt angle may be between approximately 20 and 30 degrees. The target tilt angle may be between approximately 25 and 30 degrees. The target tilt angle may be between approximately 20 and 25 degrees. The patient support structure may include one or more angle indicators configured to indicate the tilt angle. The patient support structure may include one or more accelerometers and a processor, wherein the processor may be configured to determine the tilt angle based on an accelerometer signal. The patient support structure may include a chest compression (CC) device mount disposed on at least one of the two or more patient support sections and configured to engage one or more fasteners provided by a CC device and adjustably secure the CC device to the patient support structure. The patient support structure may include an alignment feature wherein the alignment feature may include one or more indicators of a position of an anatomical reference point of the patient that will align the patient with the CC device when the CC device is coupled to the patient support structure. The patient support structure may include a manual position adjuster configured for manual adjustment of a position of the CC device relative to the patient support structure. The patient support structure may include an automated position adjuster configured to automatically adjust a position of the CC device relative to the patient support structure. The automated position adjuster may be configured to automatically adjust the position of the CC device in response to a control signal from one or more of a tilt controller disposed in the patient support structure, a defibrillator, the CC device, and a computing device. The patient support structure may be at least one of a bed, stretcher, litter, cot, gurney, a stretcher chair, and a pram.

An example of a system for assisting cardiopulmonary resuscitation (CPR) treatment of a patient according to the disclosure includes a patient support structure that includes a base frame, two or more patient support sections wherein at least one of the two or more patient support sections is coupled to and supported by the base frame and further wherein the two or more patient support sections comprise a first patient support section configured to support the legs of the patient and a second patient support section configured to support the thorax of the patient, and at least one tilt adjuster coupled to the two or more patient support sections and configured to tilt the first patient support section around a transverse axis of the patient support structure to a first tilt angle and to tilt the second patient support section around the transverse axis of the patient support structure to a second tilt angle, and a chest compression (CC) device adjustably coupled to the patient support structure.

Implementations of such a system may include one or more of the following features. The patient support structure may further include a CC device mount disposed on at least one of the two or more patient support sections and configured to engage one or more fasteners provided by a CC device and adjustably couple the CC device to the patient support structure. The at least one tilt adjuster may be an automated tilt adjuster configured to tilt the first patient support section to the first tilt angle in response to a control signal from one or more of a tilt controller disposed in the patient support structure, a defibrillator, the CC device, and a computing device. The automated tilt adjuster may be configured to adjust the first tilt angle during CPR treatment. The automated tilt adjuster may be configured to tilt the first patient support section up relative to the top of the base frame and to tilt the first patient support section down relative to the top of the base frame. The at least one tilt adjuster may be an automated tilt adjuster configured to tilt the second patient support section to the second tilt angle in response to a control signal from one or more of a tilt controller disposed in the patient support structure, a defibrillator, the CC device, and a computing device. The automated tilt adjuster may be configured to adjust the second tilt angle during CPR treatment. The patient support structure may include one or more angle indicators configured to indicate one or more of the first tilt angle and the second tilt angle. The system may include one or more accelerometers and a processor, wherein the processor is configured to determine one or more of the first tilt angle and the second tilt angle based on accelerometer signals. The patient support structure may include a chest compression (CC) device mount disposed on at least one of the two or more patient support sections and configured to engage one or more fasteners provided by a CC device and adjustably secure the CC device to the patient support structure. The patient support structure may include an alignment feature wherein the alignment feature comprises one or more indicators of a position of an anatomical reference point of the patient that will align the patient with the CC device when the CC device is coupled to the patient support structure. The system may include a manual position adjuster configured for manual adjustment of a position of the CC device relative to the patient support structure. The system may include an automated position adjuster configured to automatically adjust a position of the CC device relative to the patient support structure. The automated position adjuster may be configured to automatically adjust the position of the CC device in response to a control signal from one or more of a tilt controller disposed in the patient support structure, a defibrillator, the CC device, and a computing device. The patient support structure may be at least one of a bed, stretcher, litter, cot, gurney, a stretcher chair, and a pram.

An example of a patient support structure for assisting cardiopulmonary resuscitation (CPR) treatment of a patient according to the disclosure includes a base frame, one or more patient support sections wherein at least one of the one or more patient support sections is coupled to and supported by the base frame, and an adjustable head support mechanically coupled to one of the one or more patient support sections via a mechanical coupling configured to enable movement of the adjustable head support from a stowed position to a head support position.

Implementations of such a patient support structure may include one or more of the following features. The patient support structure may include a head support storage compartment. The patient support structure may include a spacer configured to raise and lower the adjustable head support relative to the one of the one or more patient support sections. The adjustable head support may be approximately wedge shaped. The patient support structure may include at least one tilt adjuster coupled to at least one of the one or more patient support sections and configured to tilt the at least one of the one or more patient support sections, around a transverse axis of the patient support structure, to a tilt angle. The patient support structure may include one or more angle indicators configured to indicate the tilt angle. The patient support structure may include one or more accelerometers and a processor, wherein the processor may be configured to determine the tilt angle based on an accelerometer signal. The patient support structure may include a chest compression (CC) device mount disposed on at least one of the one or more patient support sections and configured to engage one or more fasteners provided by a CC device and adjustably secure the CC device to the patient support structure. The patient support structure may include an alignment feature wherein the alignment feature includes one or more indicators of a position of an anatomical reference point of the patient that will align the patient with the CC device when the CC device is coupled to the patient support structure. The patient support structure may include a manual position adjuster configured for manual adjustment of a position of the CC device relative to the patient support structure. The patient support structure may include an automated position adjuster configured to automatically adjust a position of the CC device relative to the patient support structure. The automated position adjuster may be configured to automatically adjust the position of the CC device in response to a control signal from one or more of a tilt controller disposed in the patient support structure, a defibrillator, the CC device, and a computing device. The patient support structure may be at least one of a bed, stretcher, litter, cot, gurney, a stretcher chair, and a pram.

An example of a patient support structure for assisting cardiopulmonary resuscitation (CPR) treatment of a patient according to the disclosure includes a base frame, one or more patient support sections wherein at least one of the one or more patient support sections is coupled to and supported by the base frame, and an tilt adjuster coupled to at least one of the one or more patient support sections, the tilt adjuster including one or more inflation devices, a chest compression (CC) device configured to enable inflation and deflation of the one or more inflation devices, a control unit communicatively coupled to the CC device, and fluid conduits coupling the CC device to the one or more inflation devices.

Implementations of such a patient support structure may include one or more of the following features. The one or more patient support sections may include a first patient support section configured to support the torso of the patient and the one or more inflation devices may include a bellows configured to tilt the first patient support section relative to the base frame. The one or more patient support sections may include a second patient support section configured to support the head of the patient and the one or more inflation devices may include a head support bladder disposed on the second patient support section and configured to elevate the head of the patient relative to the torso of the patient. The patient support structure may include a CC device mount disposed on at least one of the one or more patient support sections and configured to engage one or more fasteners provided by the CC device and adjustably secure the CC device to the patient support structure. The patient support structure may include an alignment feature wherein the alignment feature includes one or more indicators of a position of an anatomical reference point of the patient that will align the patient with the CC device when the CC device is coupled to the patient support structure. The patient support structure may include a manual position adjuster configured for manual adjustment of a position of the CC device relative to the patient support structure. The patient support structure may include an automated position adjuster configured to automatically adjust a position of the CC device relative to the patient support structure. The automated position adjuster may be configured to automatically adjust the position of the CC device in response to a control signal from the control unit and based on a change in a tilt angle of the one or more patient support sections in response to inflation of the one or more inflation devices. The patient support structure may be at least one of a bed, stretcher, litter, cot, gurney, a stretcher chair, and a pram.

BRIEF DESCRIPTION OF THE DRAWINGS

Various aspects of the disclosure are discussed below with reference to the accompanying figures, which are not intended to be drawn to scale. The figures are included to provide an illustration and a further understanding of various examples, and are incorporated in and constitute a part of this specification, but are not intended to limit the scope of the disclosure. The drawings, together with the remainder of the specification, serve to explain principles and operations of the described and claimed aspects and examples. In the figures, each identical or nearly identical component that is illustrated in various figures is represented by a like numeral. For purposes of clarity, not every component may be labeled in every figure. A quantity of each component in a particular figure is an example only and other quantities of each, or any, component could be used.

FIGS. 10A and 1B are schematic diagrams of an example of patient support structure.

FIGS. 13A and 13B are schematic diagrams of an example of a patient support structure.

DETAILED DESCRIPTION

Figure 1:
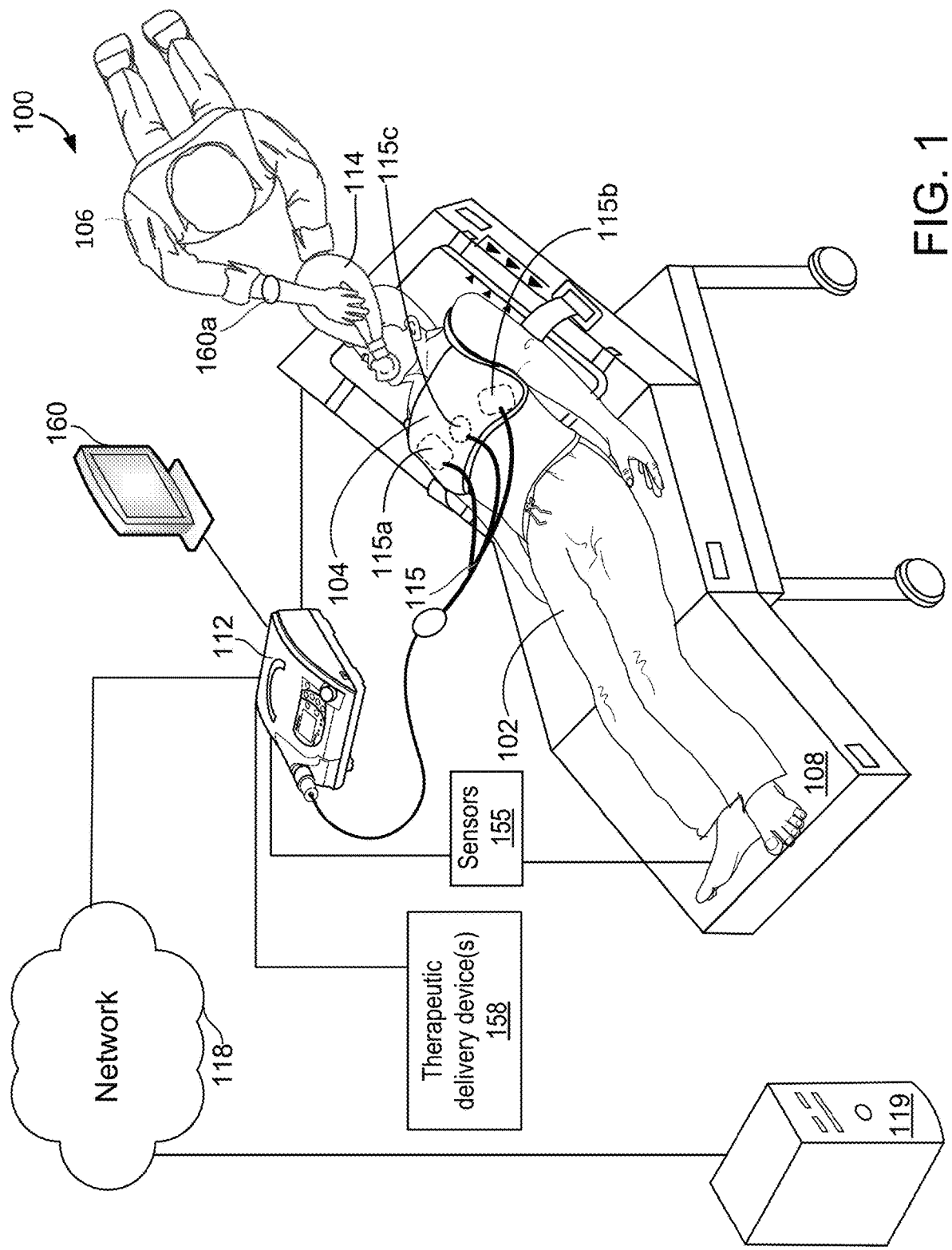
FIG. 1 is a schematic illustration of an example of a system, including a patient support structure, for providing medical treatment to a patient.

This document describes elevation systems and techniques that may be used to re-establish systemic blood flow and thereby maintain threshold levels of coronary and cerebral perfusion during a cardiopulmonary resuscitation (CPR) treatment. Implementations of the present disclosure are generally directed to systems and methods for assisting CPR treatment of a patient in need of emergency assistance, such as a patient suffering from cardiac arrest. In particular, implementations of the present disclosure are generally directed to an apparatus including a patient support structure (e.g., bed, stretcher, litter, cot, gurney, pram, etc.) that is configured to support the patient. The patient support is further configured to raise and lower at least a portion of the patient's upper body (e.g., head, shoulders, neck) and/or lower body (e.g., legs, ankles, feet) to an adjustable tilt angle. The tilt angle may improve and/or enhance CPR treatment. Generally, at least a portion of the back of the patient is in contact with a surface of the patient support, for example, when the patient is lying down on the patient support.

A chest compression (CC) device may be adjustably coupled to the patient support structure. For example, the patient support structure may be equipped with a CC device mount adapted to secure the CC device to the patient support structure. The CC device may be an automatic chest compression device. The patient may be positioned so as to be in alignment with the CC device such that chest compressions are applied at a preferred location (e.g., sternum) on the patient. Further, as the patient's upper body is raised or lowered, the chest compression device may remain aligned with the preferred location through positional adjustment of the chest compression device on the patient support structure. The position may be determined and/or adjusted manually by a care provider. Alternatively or additionally, the position may be automatically adjusted based on a tilt angle of the patient support.

A processor associated with the system 100 may further provide an indication of recommending adjustments to a tilt of the upper body of the patient based on one or more inputs to the processor. The recommended adjustments may include a tilt angle and/or a rate of tilt adjustment. The inputs may be indicative of a physiological parameter, measured signal(s), physiological phase and/or phase of resuscitative treatment. In an implementation, one or more non-invasive sensors may monitor the response of the patient to resuscitative treatment provided while maintaining the body in a tilted position. The one or more non-invasive sensors may provide the inputs indicative of the physiological parameter, the measured signal(s), and/or the physiological phase of the patient. Placing the patient in a tilted position during resuscitation (e.g., administration of chest compressions) may serve to improve and/or enhance blood circulation and/or ventilation. The processor and/or the care provider may determine appropriate modifications to the degree at which the patient should be tilted based on the patient's response.

As an example, the inputs may indicate that the cerebral oxygenation of the patient is low, or that the intracranial pressure of the patient is undesirably high. In response, the processor may recommend a tilt adjustment to raise the head of the patient relative to the heart. As another example, if the inputs indicate that the coronary perfusion pressure is low, the processor may recommend a tilt adjustment to bring the head and the heart into closer vertical relation relative to one another. As another example, if patient support section is tilted such that the head of the patient is raised and it is determined that the patient has achieved a return of spontaneous circulation (ROSC), the processor may provide an indication to lower the patient support section at a relatively slow rate (e.g., slower than the rate at which the patient support section was raised). In some cases, a processor associated with the system 100 may determine how the head and the heart should be vertically positioned relative to one another. This determination may be made in real-time during treatment and previously determined positions may be updated. For example, the processor may recommend a first elevation and/or degree of tilt of the patient support section to suit the particular needs of the patient during a first time interval and a second and different elevation and/or degree of tilt of the patient support section to suit the particular needs of the patient during a second time interval. Such a technique may be beneficial to achieve a suitable balance between coronary and cerebral perfusion pressures.

Certain physiological signals may provide an indication of the determined physiological phase of the patient. The physiological phase of the patient may include detection of ROSC. The physiological phase of the patient may include a type of cardiac event and/or respiratory event experienced by the patient. The type of cardiac event experienced by the patient may be a cardiac arrest of arrhythmic etiology (stemming from an electrical disturbance in the normal cardiovascular conduction system), a cardiogenic shock etiology (stemming from a failure of the heart to pump enough blood and therefore the heart itself cannot get enough oxygen to its own muscle, e.g., acute myocardial infarction, severe hemorrhage), and/or a respiratory arrest of pulmonary etiology (stemming from a failure of the pulmonary system to oxygenate blood, e.g., due to effects of drugs or damage to the lungs). Other examples of physiological phases may include differentiation of patient's condition based on the lapsed time from the onset of the cardiac event (e.g., electrical phase, circulatory phase, metabolic phase).

To perform chest compression treatment, a care provider may manually apply chest compressions directly to the chest of the patient with his/her hands. Alternatively, the care provider may apply force manually (e.g., compressions and/or decompressions) to a patient using hands and/or a manual compression device. The manual compression device may include an adhesive pad, suction cup(s), or other mechanical coupling to the chest of the patient. The caregiver may appropriately align a manual device with the patient. As another example, the care provider may employ an automated chest compression device (e.g., a piston based compressor, belt based compressor, etc.). The caregiver may apply chest compressions by aligning the manual or the automated chest compression device with the patient.

Generally speaking, chest compressions are typically performed while the patient is in a supine or substantially horizontal position, resulting in an overall increase in venous and arterial pressures with each compression, which may limit the generation of an effective cerebral perfusion gradient. In some cases, the simultaneous increase in venous and arterial pressures may cause harm to the brain as each compression creates a high pressure concussion wave directed to the brain within the fixed structure of the skull. In accordance with aspects of the present disclosure, the care provider and/or the chest compression device may apply the chest compressions while at least a portion of the patient's upper body is elevated at a particular angle relative to a horizontal axis. In an implementation, the system according to the disclosure may enable delivery of CPR treatment at a preferred location of the patient's chest that remains substantially invariant with changes in a tilt angle. A chest compression device may enable applying chest compression pressure circumferentially about the chest. The patient support structure described herein is an elevation apparatus that is configured to elevate and tilt one or more portions of a patient's body during CPR treatment. Such elevation and tilting may improve resuscitative therapy by regulating intracranial pressure while increasing blood circulation during the administration of chest compressions. Elevation of the head or head and shoulders may be effective to allow for drainage of cerebrospinal fluid from the head, resulting in an overall reduction in intracranial pressure, which may then provide for enhanced cerebral perfusion.

Other capabilities may be provided and not every implementation according to the disclosure must provide any, let alone all, of the capabilities discussed. Further, it may be possible for an effect noted above to be achieved by means other than that noted and a noted item/technique may not necessarily yield the noted effect.

Referring to FIG. 1, a schematic illustration of an example of a system 100, including a patient support structure, for providing medical treatment to a patient is shown. FIG. 1 illustrates an overhead view of the patient 102 receiving CPR treatment from an automated chest compression (CC) device 104, a defibrillator 112, and a care provider 106. The patient 102 is positioned on a patient support structure 108 configured to assist CPR treatment. The care provider 106 may be an acute care provider. Additionally, the care provider 106 may include lay care providers, who were in the vicinity of the patient 102 when the patient 102 required care and/or trained medical personnel, such as emergency medical personnel (EMTs). Although one care provider 106 is shown in FIG. 1, additional care providers may also care for the patient 102. In an implementation, a plurality of care providers 106 may be included in a rotation of care providers providing particular components of care to the patient 102. The components of care may include, for example, chest compressions, ventilation, administration of drugs, and other provisions of care.

In general, the system 100 may include various portable devices for monitoring on-site care given to the patient 102. The various devices may be provided by emergency medical personnel who arrive at the scene and who provide care for the patient 102, such as the care provider 106. The devices used by the care provider may include the CC device 104 and the defibrillator 112. The CC device 104 may be attached to another device used by the medical personnel during CPR, such as the portable defibrillator 112. The attachment of the CC device 104 with other devices can enable synchronization of multiple CPR related procedures.

Figure 2A:
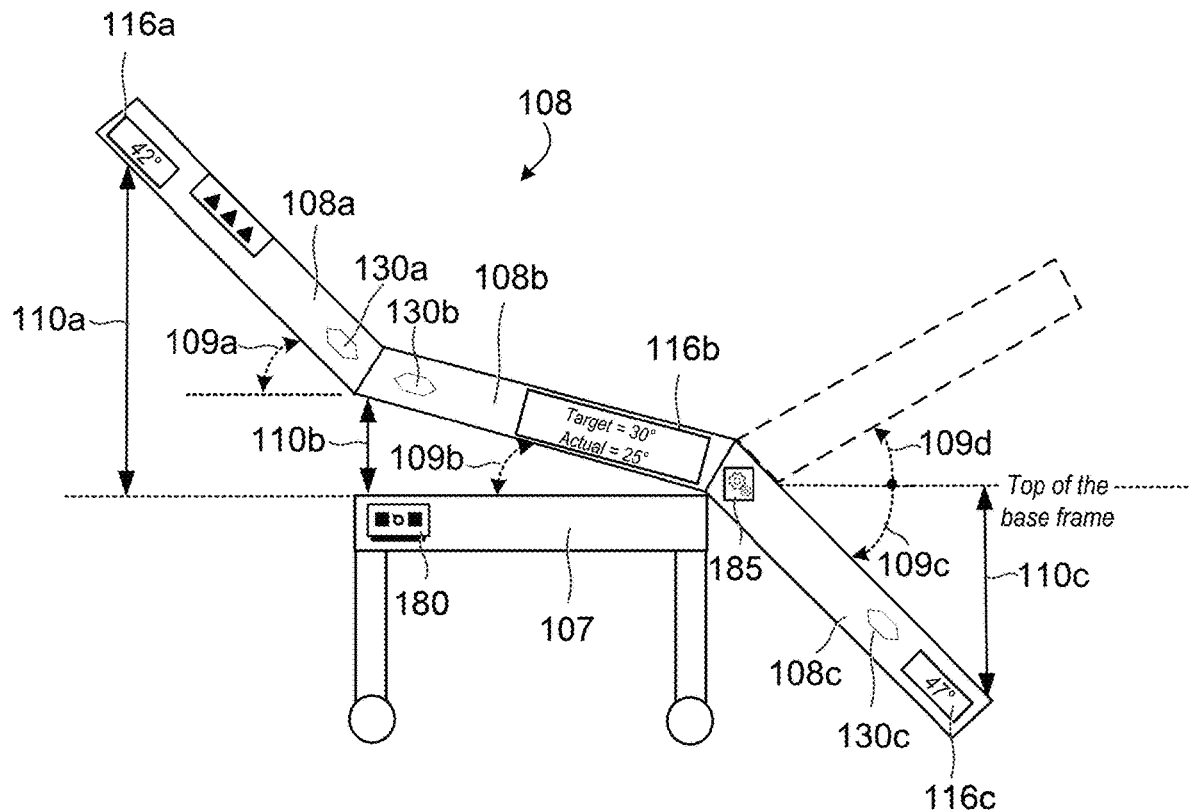
FIGS. 2A and 2B are schematic diagrams of the patient support structure shown in FIG. 1.
Figure 2B:
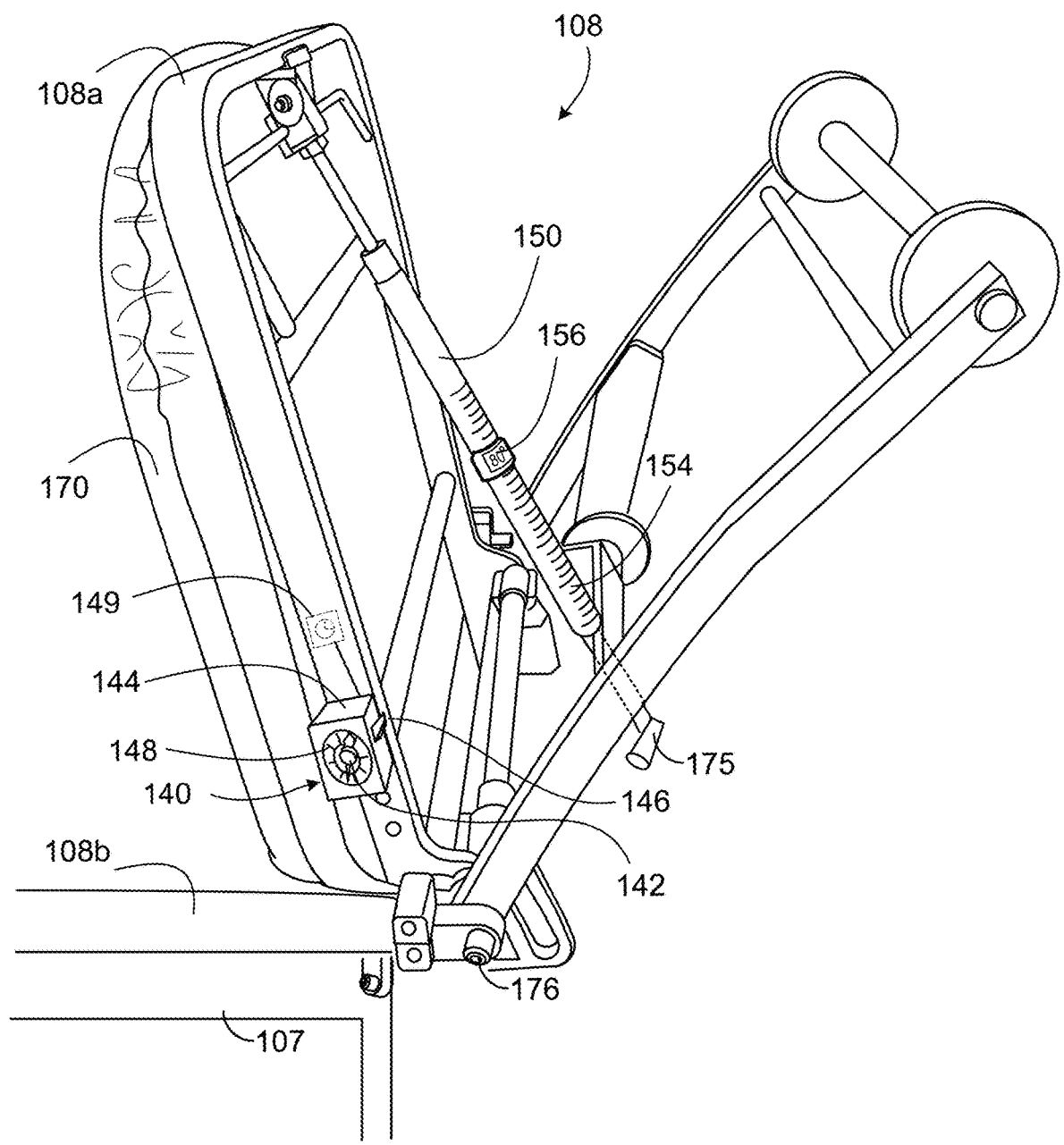

Referring to FIGS. 2A and 2B, the patient support structure 108 may be a patient support structure such as, for example, but not limited to, a bed, stretcher, litter, cot, gurney, or a pram. It can be appreciated that other patient support structures may be employed. The patient support structure 108 may be an articulated patient support structure and may include one or more patient support sections 108a, 108b, and 108c. Although three support sections are shown in FIG. 2A, this quantity of support sections is an example only as other quantities of support sections are possible. The patient support sections 108a, 108b, and 108c may be made from metal (e.g., angle iron) sections connected to form a frame. One or more of the patient support section 108a, 108b, and 108c may include a padded support 170 disposed on the frame. One or more of the patient support sections 108a, 108b, and 108c may be pivotally coupled to another patient support section and/or to a base frame 107 at, for example, one or more pivot sets 176. The base frame 107 may be made from different metals and or tubing, welded and/or bolted together, such as metal square tubing, metal angle iron and metal U channel track. Each of the sections 108a, 108b, and 108c may be configured to support a particular portion of a patient's body. For example, the support section 108a (e.g., a first patient support section) can be configured to support the patient's head, neck, and all or a portion of the patient's torso (i.e., shoulders and upper back or shoulders, upper back, and lower back). The support section 108b (e.g., a second patient support section) may be configured to support all or a portion of the patient's torso and all or a portion of the patient's legs (i.e., thighs, calves, and feet or thighs and calves, or thighs). The support section 108c (e.g., a third patient support section) may be configured to support all or a portion of the patient's legs (i.e., thighs, calves, and feet or thighs and calves, or thighs).

One or more of the patient support sections may be further configured to adjustably tilt about a transverse axis of the patient support structure (e.g., the X axis 126a) to raise or lower the supported particular portion of the patient's body. For example, one or more of the plurality of support sections 108a, 108b, and 108c may be tilted independently from each other of the plurality of support sections. The patient support sections 108a, 108b, and/or 108c may tilt relative to one another and/or relative to a base frame 107. In an implementation, the patient support structure 108 may encompass one patient support section configured to adjustably tilt relative to the base frame 107 about the transverse axis.

The plurality of support sections 108a, 108b, and 108c may be tilted independently from each other of the plurality of support sections at tilt angles 109a, 109b, 109c, and/or 109d. Each of the tilt angles 109a, 109b, 109c, and 109d may be measured relative to an axis (e.g., one of the horizontal axis 126a, horizontal axis 126b and vertical axis 126c) or relative to a horizontal plane defined by axes 126a and 126b. In an implementation, the X axis 126a and the Y axis 126b define the plane of the surface of the patient support structure 108 with the X axis 126a corresponding to the transverse axis of the patient support structure 108 and the Y axis 126b corresponding to the longitudinal axis of the patient support structure 108. The Z axis 126c is approximately perpendicular to a top surface of the patient support structure 108 (i.e., the outward facing surface of the patient support structure 108 facing away from the base frame 107). The tilting rotates the Y-Z plane around the X axis. In some implementations, the tilt angle 109a of the support section 108a is greater than the tilt angle 109b of the support section 108b, such that the head is higher than the thorax of the patient. In an implementation, the support section 108c is configured to support at least a portion of the legs of the patient. The support section 108c may tilt down relative to the top of the base frame 107 at the tilt angle 109c such that the legs of the patient 102 are lower than the thorax. Alternatively, the support section 108c may tilt up relative to the top of the base frame 107 at the tilt angle 109d such that the legs of the patient 102 are higher than the thorax. The tilted up configuration is shown in FIG. 2A with the support section 108c drawn with dotted lines at tilted at the angle 109d. The tilted configuration (e.g., tilted up or tilted down) of the support section 108c may enable control of peripheral vascularization for the patient 102.

The patient support structure 108 may include at least one tilt adjuster. Each tilt adjuster is configured to tilt at least one of the patient support sections 108a, 108b and 108c to a tilt angle 109a, 109b, 109c, or 109d. Further the at least one tilt adjuster may be configured to adjust a tilt angle from a first tilt angle to a second tilt angle during CPR treatment. The adjustment may increase or decrease the tilt angle. The at least one tilt adjuster may include one or more manual tilt adjusters 175 and/or one or more automated tilt adjusters 185. The manual tilt adjusters 175 are configured to tilt at least one of the patient support sections 108a, 108b and 108c to the tilt angle 109a, 109b, 109c, and/or 109d in response to manipulation of the manual tilt adjuster 175 by the care provider. The automated tilt adjusters 185 are configured to tilt at least one of the patient support sections 108a, 108b and 108c to the tilt angle 109a, 109b, 109c, and/or 109d in response to a control signal from one or more of the defibrillator 112, the CC device 104, the tilt controller 180, and the local computing devices 160.

The one or more sections of the patient support structure 108 may be automatically or manually set to a particular tilting configuration (defining the tilt angle of each surface of the patient support structure 108), based on one or more of a physiological parameter, a physiological signal, a physiological phase or a phase of the CPR treatment. For example, the care provider 106 may set the tilting configuration of the patient support structure 108 before and/or while CPR treatment is provided to the patient 102 by the CC device 104. Alternatively, based on a physiological parameter of the patient (e.g., measured from a sensor), a processor (e.g., the processor 3300 described below with regard to FIG. 3B) may provide an indication for how one or more patient support sections of the patient support structure 108 should be tilted for treating the patient. Such an indication may be provided to the care provider 106 as a recommendation, to support a decision on whether and/or how to adjust the tilt level of the one or more patient support sections of the patient support structure 108. Alternatively, the indication may be provided to an automated elevating component of the patient support structure 108 to tilt one or more of the patient support sections according to an appropriate treatment protocol and/or algorithm. Such automation may be performed independent of or may require input from the care provider 106.

The one or more manual tilt adjusters 175 may enable the care provider 106 to manually tilt the support sections 108*a*, 108*b*, and/or 108*c*. The manual tilt adjusters 175 may tilt the patient support sections 108*a*, 108*b*, and/or 108*c* and/or adjust the tilt of the patient support sections 108*a*, 108*b*, and/or 108*c* during CPR treatment. For example, the manual tilt adjuster may include one or more manually operable lever arms and tilt actuators. When the care provider 106 rotates the lever arm in a first direction, the patient support section 108*a* may tilt so as to raise the patient support section 108*a* relative to the patient support section 108*b*. Such a motion may increase the tilt angle 109*a* between the patient support sections 108*a* and 108*b*. Similarly, when the care provider 106 rotates the lever arm in a second direction, the patient support section 108*a* may tilt so as to lower the patient support section 108*a* relative to the patient support section 108*b*. Such a motion may decrease the tilt angle 109*a* between the patient support sections 108*a* and 108*b*. Other appropriate manual tilt adjusters are possible and the example of the manual tilt adjuster described above is not limiting of the disclosure.

The one or more automated tilt adjusters 185 may automatically tilt the support sections 108*a*, 108*b*, and/or 108*c* in response to a control signal from one or more of the defibrillator 112, the CC device 104, the tilt controller 180, and the local computing devices 160. The one or more automated tilt adjusters 185 may tilt the patient support sections 108*a*, 108*b*, and/or 108*c* and/or adjust the tilt of the patient support sections 108*a*, 108*b*, and/or 108*c* during CPR treatment. For example, each automated tilt adjuster 185 may include a reversible or bi-directional motor along with one or more gears, drive shafts, clutches, linkages, and/or other appropriate hardware to move a corresponding patient support section in response to the motor being energized. Each of the one or more automated tilt adjusters 185 may further include an appropriate electrical circuit including one or more switches configured to activate the circuit. In an implementation, a tilt controller 180 may be configured to selectively control the one or more automated tilt adjusters 185 to tilt one or more of the support sections 108*a*, 108*b*, and 108*c*. For example, the tilt controller 180 may provide a control signal indicative of a recommended tilt angle to the automated tilt adjuster 185. The tilt controller 180 may be connected to the automated tilt adjusters 185 by a wired and/or wireless connection. One or more pivot sets 176 of the patient support structure 108 may include potentiometers configured to detect tilting of a support section (e.g., 108*a*, 108*b*, and/or 108*c*) being moved by the automated tilt adjusters 185. Other appropriate automated tilt adjusters are possible and the example of the automated tilt adjuster described above is not limiting of the disclosure.

Figure 14:
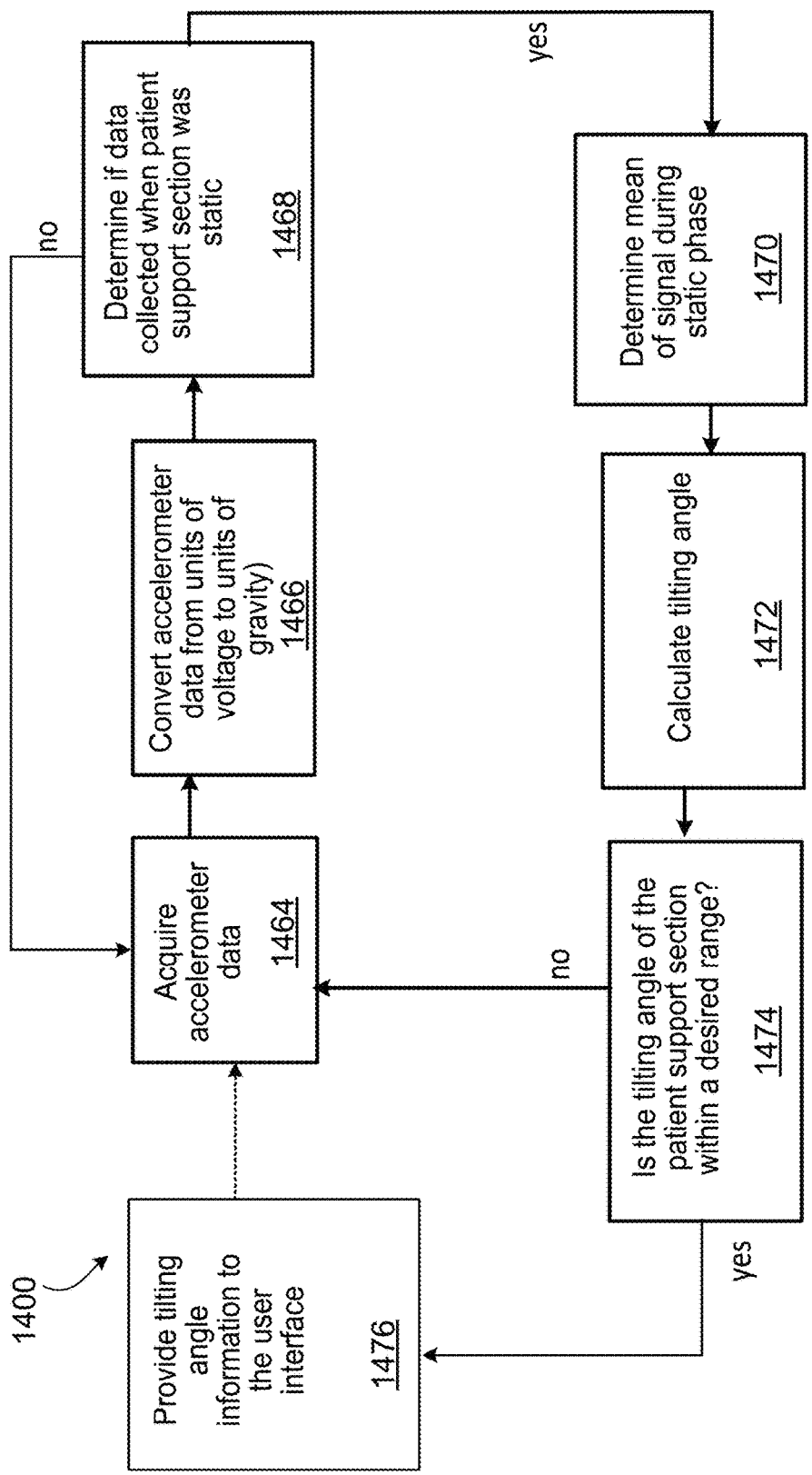
FIG. 14 shows a block diagram of an example of a method for determining a tilt angle adjustment for a patient's head based on signals from a 3-axis accelerometer.

Additionally, the tilt controller 180 and/or the one or more automated tilt adjusters 185 may be communicatively coupled to an external computing device (e.g., as described with regard to FIG. 14). The external computing device may provide a control signal and/or instructions to the tilt controller 180 and/or the one or more automated tilt adjusters to adjust one or more of the tilt angles 109*a*, 109*b*, 109*c*, and 109*d*. The control signal may be indicative of the recommended tilt angle. The tilt controller 180 may include an input device (e.g., a touch screen, a keyboard, a mouse, joystick, trackball, or other pointing device, a microphone, and/or a camera, etc.) and/or an output device (e.g., a display, a speaker, and/or a haptic device).

In an implementation, the pivot sets 176 may include rotational locks. The rotational lock may temporarily lock the pivot set 176 at a particular rotational angle. The rotational lock may be a mechanical lock actuated by the manual tilt adjuster and/or the automated tilt adjuster. The mechanical lock may include, for example, but not limited to, a pin and keyhole, a lock plate and lock gear, etc. configured to engage and disengage with a rotatable component of the pivot set.

The patient support structure 108 may include one or more angle indicators that indicate the angles 109*a*, 109*b*, 109*c*, and/or 109*d*. In an implementation, the one or more angle indicators may indicate an actual angle. Additionally, the one or more angle indicators may indicate a desired or target angle and/or angular range. In various implementations, the one or more angle indicators may include electronic angle indicators (e.g., displays 116*a*, 116*b*, 116*c* in FIG. 2A) and/or mechanical angle indicators (e.g., inclinometer 140 and/or support bar 150 in FIG. 2B). As an example, electronic angle indicator 116*b* includes a target angle. The mechanical angle indicators may include a marker that indicates a target angle and/or a target angular range. The marker may be adjustable. For example, the marker may include angular indicia of a different color than other angular indicia, an angular indicia of a different size than other angular indicia, and/or a sticker, groove, and/or light indicating a target angle and/or angular range. In various implementations, the one or more angle indicators may include a light, sound, or other output signal that indicates a target angle and/or target angular range. These angle indicators are examples only and not limiting of the disclosure. Further, although FIGS. 2A and 2B show multiple examples of types of angle indicators associated with the patient support structure 108, the patient support structure 108 may include none, one, or more than one of these illustrated types of angle indicators and/or another type of suitable angle indicator. Additionally, the position and quantity of the angle indicators in FIGS. 2A and 2B are examples only and other positions and quantities are possible.

The angle indicators may be configured to indicate accurate tilt angles for precisely controlling the manner in which parts of the patient's body are tilted or otherwise elevated.

For example, an angular range of 20 to 30 degrees may be appropriate for resuscitative success during one phase of CPR treatment, while an angular range of 10 to 20 degrees may be appropriate for resuscitative success for another phase of CPR treatment. The angle indicators may enable the care provider 106 to maintain elevations particular to a plurality of situations.

In an implementation, the patient support structure 108 may include one or more of accelerometers 130*a*, 130*b*, and 130*c*. The angle indicators 116*a*, 116*b*, and 116*c* may be configured to display or otherwise provide angles determined based on signals received from the one or more of accelerometers 130*a*, 130*b*, and 130*c*. For example, the defibrillator 112, the 180, and/or the local computing device 160 may receive the accelerometer signals and determine the tilt angle from the accelerometer signals as described in further detail below with regard to FIGS. 14 and 15. The accelerometer signals may be indicative of one or more tilt angles of the one or more patient support sections.

In some implementations, the patient support structure 108 may provide one or more of the angle indicators 116*a*, 116*b*, and 116*c* as a mechanical angle indicator such as a protractor and/or an inclinometer. Inclinometers measure and display angles of tilt, elevation or depression of the respective support surface with respect to gravity. The inclinometer may involve a component typically used in leveling instruments to determine the tilt or slope of the surface, such as a ball, bubble, pendulum, MEMs tilt sensor, or other component.

Referring to FIG. 2B, an example of an inclinometer 140 is shown. The inclinometer 140 is shown on support section 108*a* in FIG. 2B. However, this is an example only and not limiting of the disclosure. One or more of the support sections 108*a*, 108*b*, and 108*c* may include these components.

The inclinometer 140 is configured to display a degree of tilt (e.g., one of the angles 109*a*, 109*b*, 109*c*, and 109*d*) of a corresponding support section (e.g., support section 108*a*, 108*b*, or 108*c*). The degree of tilt may be relative to a horizontal plane such as the horizontal plane of the base frame 107 or relative to another plane of the patient support structure 108. For example, the mechanical indicator may include a protractor. In an implementation, an example of the inclinometer 140 includes a housing 144, a pointer 142, and angle indicia 148.

The housing 144 may include a mounting structure 146 configured to couple the inclinometer 140 to the corresponding support section. The mounting structure 146 may permanently or removably secure the mechanical angle indicator 140 to the corresponding support section. The mounting structure 146 may be integrally formed with the housing 144, or provided separately. The mounting structure 146 may include, as examples not limiting of the disclosure, adhesives, welds, bolts, rivets, permanent magnets, hook and loop fasteners (e.g., Velcro® brand hook and loop fasteners), screws, snap fit connectors, adhesive tapes, and combinations thereof. In an implementation, the mechanical angle indicator 140 may be integrally formed with or within the corresponding structure rather than being coupled to the corresponding structure.

The housing 144 may take on a variety of forms and is not limited to the examples provided herein. The housing 144 may be composed of a transparent material, such as plastic or glass, to facilitate observation the angle of inclination indicated by the pointer 142. The housing 144 may include a plurality of walls forming an enclosed housing with a semicircular cross-section. Other housing shapes are possible and within the scope of the disclosure. For example, housing 144 may have a fully circular cross section, or a rectangular, hexagonal, pentagonal or other cross sectional shape. Moreover, housing 144 may not be an enclosed structure. In some implementations, housing 144 may include only one wall configured to mount the housing 144 to the corresponding support section. The one wall may be a transparent wall with the pointer 142 attached thereto and transparent indicia 148 formed thereon.

The pointer 142 is movably disposed in the housing 144 and has an angular range of motion about an axis intersecting the plane of the base frame 107. Indicia 148 are provided on the housing 144 and proximate to the pointer 142. In an implementation, the indicia 148 indicate selectable tilt angles for the corresponding support section with respect to the plane of the base frame 107.

The pointer 142 may have a variety of forms. For example, the pointer 142 may include a pendulum having a first end mounted to a pivot point and a second end adapted and configured to visually contrast with the angle indicia 148. The second end of the pointer 142 may be generally ball-shaped or needle-shaped with a point. As another example, the pointer 142 may include a cylindrical roller adapted and configured to move along an arcuate path. The roller may be adapted and configured to roll along arcuate wall of the housing 144. Alternatively, the pointer may be ball-shaped and roll in a grooved track along the arcuate wall of the housing 144. As a further example, the pointer 142 may be a slidable component attached to a wire track coupled to the housing 144.

As a further example of the mechanical angle indicator, the patient support structure 108 may include a support bar 150 with angle indicia 154. A slidable pointer 156 may indicate the tilt angle of the corresponding support section.

The particular rotational angle effected by the manual tilt adjuster 175 and/or the automated tilt adjuster 185 may be based one or more of a physiological parameter for the patient, a physiological signal from the patient, a physiological phase of the patient, and a phase of the CPR treatment. The particular rotational angle may correspond to a recommended angle corresponding to the physiological parameter for the patient, the physiological signal from the patient, the physiological phase of the patient, and/or the phase of the CPR treatment. These preset tilt angles may be previously determined, for example, based on clinical studies, reviews of treatment outcomes, medical care protocols, personal experience of the care provider, etc.

The preset tilt angles may be between approximately 0 and 40 degrees, between approximately 0 and 30 degrees, between approximately 10 and 30 degrees, between approximately 10 and 20 degrees, between approximately 20 and 30 degrees, between approximately 25 and 30 degrees, or between approximately 20 and 25 degrees as determined relative to a horizontal axis 126*a* or 126*b*. These angular ranges are not limiting of the disclosure as the tilt angles 109*a*, 109*b*, 109*c*, and/or 109*d* may fall within other ranges. Tilting the support sections 108*a*, 108*b*, and/or 108*c* moves the tilted support section a distance 110*a*, 110*b*, and 110*c*, respectively, away from the base frame 107. In an implementation, the distances 110*a*, 110*b*, and 110*c* may be, for example, between approximately 0 and 50 cm, between approximately 2 and 50 cm, or between approximately 2 and 20 cm. These distances are not limiting of the disclosure as the distances 110*a*, 110*b*, and/or 110*c* may fall within other ranges. In some cases, the indication of the tilt angle of the support may include an indication of the approximate relative vertical distance of the various support sections from the base. These distances may be indicative of relative distances between certain parts of the patient's body and/or between the parts of the patient's body and sections of the patient support structure (e.g., approximate elevation of the brain relative to the heart or other part of the patient or the patient support structure).

In an implementation, the care provider may manually set one or more of the angles 109a, 109b, 109c, and/or 109d based on the care provider's knowledge of the recommended angles for various physiological indications and/or CPR treatment phases. Further, the care provider may manually adjust one or more of the angles 109a, 109b, 109c, and/or 109d according to changes in the various physiological indications and/or CPR treatment phases. The care provider may manually set the one or more of the angles 109a, 109b, 109c, and/or 109d via manual tilt adjusters 175 and/or via input to the tilt controller 180. In an implementation, the manual tilt adjuster hardware may allow the care provider to select and adjust these angles along a continuous angular range. In another implementation, the manual tilt adjuster hardware may limit the selectable angles to particular angles and/or angular ranges previously determined as the recommended angles. For example, the pivot sets 176 may be configured to rotationally lock at pre-selected angles or in pre-selected angular ranges as determined during manufacturing and/or a pre-treatment configuration of the patient support structure 108. In a further implementation, the patient support structure 108 may include indicia on the angle indicators (e.g., the support bar 150, the inclinometer 140, and/or the angle indicators 116a, 116b, and 116c) configured to indicate recommended angles and/or angular ranges. These indicia may include, for example, but not limited to, one or more graphic markings, text markings, lights, audible indicators, colored icons, engravings, divots, bumps, etc.

In some implementations, the inclinometer 140 may include or be coupled to an alarm 149 configured and adapted to emit an alarm signal when the pointer 142 and the indicia 148 are not in visual alignment (e.g., the current tilt angle does not correspond to the target tilt angle) and/or if the angle of elevation does not correspond to a desired elevation at the time. The alarm signal may be an auditory signal and/or a visual signal. Additionally, the alarm 149 may relay, via a wired and/or wireless connection, the alarm signal to the tilt controller 180 or an external monitoring system (e.g., the defibrillator 112). The alarm 149 may include and/or be coupled to a timing device configured to allow for temporary repositioning of one or more of the support sections 108a, 108b, and 108c before the alarm 149 emits the alarm signal. As such, one or more of the support sections may be in an incorrect position for a predetermined period of time (e.g., 2 minutes) prior to the alarm 149 emitting the alarm signal. The manual tilt adjuster 175 and/or the automated tilt adjuster 185 may be configured to set the tilting configuration of the patient support structure 108 prior to and/or during CPR treatment by the CC device 104.

In some implementations, the system 100 may include additional therapeutic delivery devices 158. The additional therapeutic delivery devices 158 may include, for example, a drug infusion device, an automatic ventilator and/or a device that includes multiple therapies such as defibrillation, chest compression, abdominal compression, ventilation, and drug infusion. The therapeutic delivery devices are physically separate from the defibrillator 112. In various implementations, the defibrillator 112 may control the therapeutic delivery devices 158 via a wired and/or wireless communications link between the defibrillator 112 and the therapeutic delivery devices 158.

The remote computing devices 119 may include a server and/or another computing device (e.g., a personal computer, a laptop computer, a mobile device, a hand-held device, a wireless device, a tablet, a medical device, a defibrillator, a patient monitor, a wearable device (e.g., a wrist-worn device, a head-worn device, etc.), or combinations thereof. The server may be a cloud server or central facility server. The one or more external computing devices may additionally and/or alternatively include a server and/or a computing device associated with a medical provider (e.g., a hospital, a physician's office, a medical records office, an emergency services office, an emergency services vehicle, a dispatch center, etc.). The network 118 may be, for example, but not limited to, a local area network, a cellular network, and/or a computer network (e.g., an Internet Protocol network).

One or more computing components of the system 100 (e.g., the defibrillator 112, the remote computing device 119, the local computing device(s) 160, and/or the CC device 104) may include one or more stored CPR protocols (e.g., as stored in a memory of the one or more computing components of the system 100). Further, the one or more computing components of the system 100 may be configured to select and implement a particular protocol based on one or more parameters, such as patient characteristics, patient's medical conditions and patient's response to treatment. Some parameters may be automatically measured and processed by one or more computing components of the system 100 and some parameters may be entered by the care providers. Protocols may be generally configured based on AHA guidelines. The protocols may include the duration of each phase of the CPR treatment, one or more force parameters that should be applied during each of the phases (e.g., the force variation, force amplitude, force thresholds, and angles for applying the force). In some implementations, the care provider, such as a medical director or an experienced care provider, may alter such guidelines to fit particular patient needs, according to professional judgment. For example, the defibrillator 112 and/or the CC device 104 may be programmed with the parameters for each of the protocols. An operator of the defibrillator 112 may select a protocol to be executed by the defibrillator 112 (or the protocol may have been selected by a medical director) and the protocol to be executed by the CC device 104. Such a selection may occur at the time of a rescue or prior to the time of the rescue. For example, the ability to select a protocol may be differentiated based on access privileges, such as a person who runs an EMT service (e.g., a medical director of appropriate training and certification to make such a determination). A user interacting with the defibrillator 112 and/or the CC device 104 may select the protocol to be followed on each of the machines operated by the service, and other users may be prevented from making particular changes, if lacking access privileges. In this manner, the defibrillator 112 and/or the CC device 104 may match its performance to whatever protocol its users have been trained to.

Figure 3A:
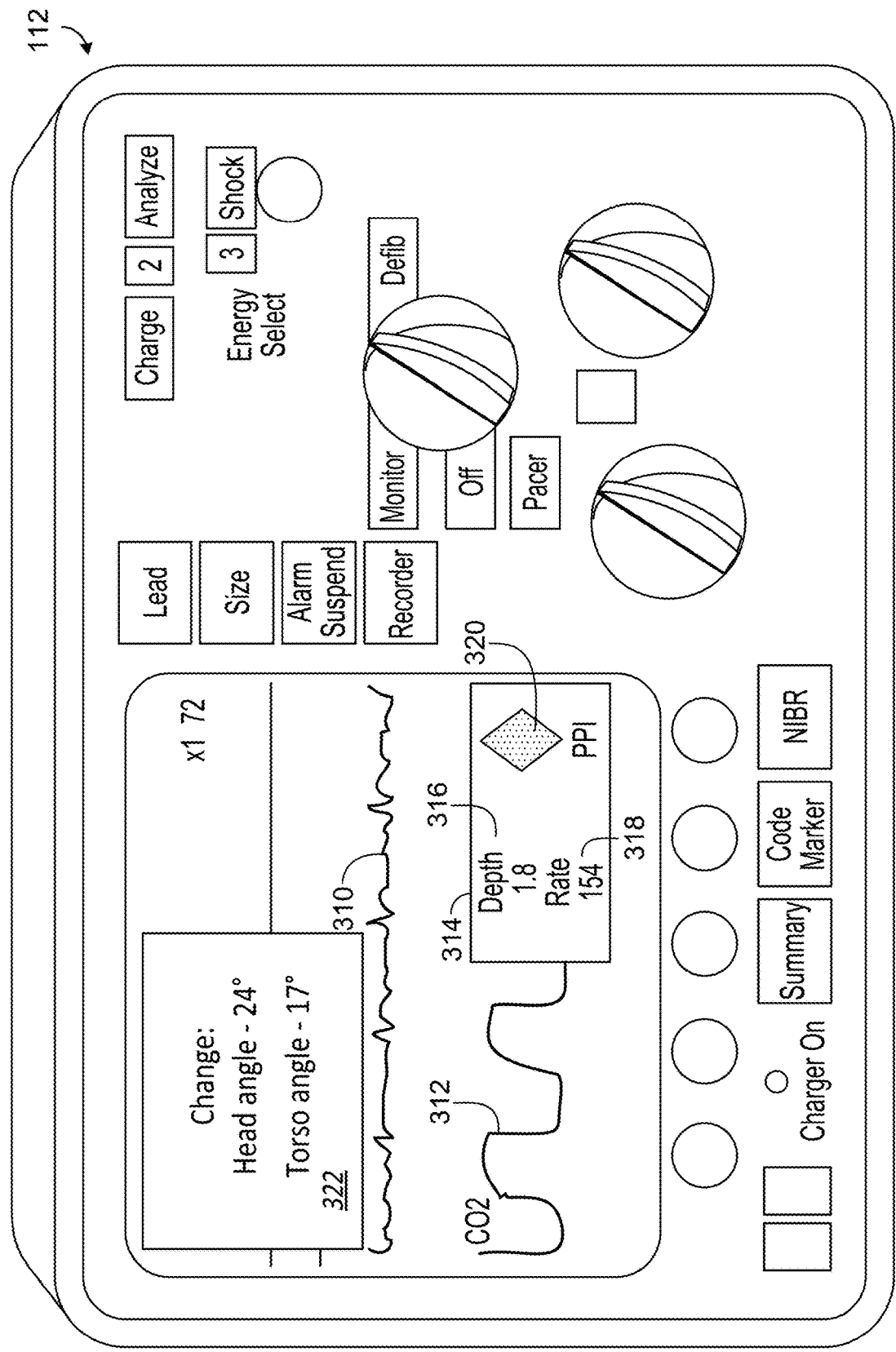
FIG. 3A is an example of the defibrillator of FIG. 1.

Referring to FIG. 3A with further reference to FIG. 1, an example of the defibrillator of FIG. 1 is shown. The defibrillator 112 is configured to physically connect with the patient 102 via a defibrillation electrode assembly 115. In the example of FIG. 1, the defibrillator 112 is shown in a deployed state connected to the patient 102 via the defibrillation electrode assembly 115. The electrode assembly 115 is illustrated in FIG. 1 as being attached to the patient 102 in a standard position. The electrode assembly 115, in this example, includes an electrode 115a positioned high on the right side of the patient's torso and an electrode 115b positioned low on the left side of the patient's torso. In the illustrated example, the electrodes 115a and 115b have been applied to the bare chest of the patient 102 and have been connected to the defibrillator 112, so that electrical shocking pulses may be provided to the patient via the electrodes 115a and 115b in an effort to defibrillate the patient 102. Additionally or alternatively, electrodes 115a and 115b may enable the defibrillator 112 to capture electrocardiogram (ECG) signals from the patient 102. The defibrillator 112 may provide feedback for the care provider 106 based at least in part on the ECG signals.

The electrode assembly 115 may include a chest compression sensor 115c. The chest compression sensor 115c may include a motion sensor and/or a force sensor configured to detect chest compressions. Additionally or alternatively, the CC device 104 may include the chest compression sensor 115c and/or the chest compression sensor 115c may be a device provided by the care provider 106 (e.g., a compression puck, a smart phone, a wearable device, and/or other device equipped with a motion sensor and/or a force sensor). During chest compressions, the chest compression sensor 115c is located over the patient's sternum. In various implementations, the chest compression sensor 115c may include an accelerometer, a force sensor, and/or other sensors that provide one or more signals to the defibrillator 112 indicative of chest compressions. For example, the chest compression sensor 115c may be placed on a patient's sternum and may deliver signals indicative of acceleration of the chest compression sensor 115c, and thus of up-down acceleration of the patient's sternum, which can be mathematically integrated so as to identify a depth of compression by the care provider 106. Additionally or alternatively, the chest compression sensor 115c may be used more simply to identify whether the patient 102 is currently receiving chest compressions or not. Based on these signals, the defibrillator 112 may determine an overall quality score for the chest compressions and decompressions. The quality score may indicate instantaneous quality and/or average quality across a time.

The defibrillator 112 may operate according to shock delivery protocol (e.g., to provide current to the electrode package 115 at voltages and/or time intervals indicated by the protocol). The defibrillator 112 may be a portable defibrillator. Further, the defibrillator 112 may be a professional defibrillator, such as, for example, but not limited to, the R SERIES®, M SERIES®, E SERIES®, or X SERIES® from ZOLL® Medical Corporation of Chelmsford, Mass. Alternatively, the defibrillator 112 may be an automated external defibrillator (AED), including, for example, but not limited to, the AED PLUS®, or AED PRO® from ZOLL® Medical Corporation. The defibrillator 112 is shown in FIG. 1 in one position relative to the care provider 106, but may be placed in other locations.

The defibrillator 112 may provide information and/or feedback for the care provider via lights, displays, vibrators, and/or audible sound generators that are components of the defibrillator 112. Alternatively or additionally, the defibrillator 112 may send this information and/or feedback to one or more local computing device(s) 160. The local computing device(s) 160 may be physically separate from the housing of the defibrillator 112. The defibrillator 112 may provide defibrillation shocks, physiologic signal analysis, etc. The defibrillator 112 may include a display 302 that provides information about patient status and CPR administration quality during the use of the defibrillator 112.

The local computing device(s) 160 may display and/or otherwise provide the received information and/or feedback and may include a graphical user interface. For example, the local computing device(s) 160 may include a display and/or a computing device. As another example, the local computing device(s) 160 may include a chest-mounted component such as a display or other output device disposed on the electrode assembly 115. As a further example, the local computing device(s) 160 may include a device 160a associated with the care provider 106 (e.g., an addressable earpiece, a display, glasses, a smartphone, a watch, a wearable device, etc.). The local computing device(s) 160 may communicate information about the patient 102 and/or performance of CPR to/from the defibrillator 112. The local computing device(s) 160 may receive feedback information from the defibrillator 112, through a wired and/or wireless coupling with the defibrillator 112 and/or indirectly through another device or devices. The local computing device(s) 160 may provide information and/or feedback to the care provider 106 from a location that is away from the defibrillator 112, and more immediately in the line of sight and focus of attention of the care provider 106. In an implementation, the local computing device(s) 160 include a CC assistance device configured to deliver instant audiovisual feedback of compression depth and rate, complete chest recoil, hands-off time, ventilation rate, etc.

The defibrillator 112 may include a processor 3300 configured to determine output including a tilt angle, a patient treatment indication, and/or feedback for a care provider. The determined output may include instructions, recommendations, and/or feedback for one of more of the tilt controller 180, a user interface 3324, and/or a treatment device controller 3326.

Figure 3B:
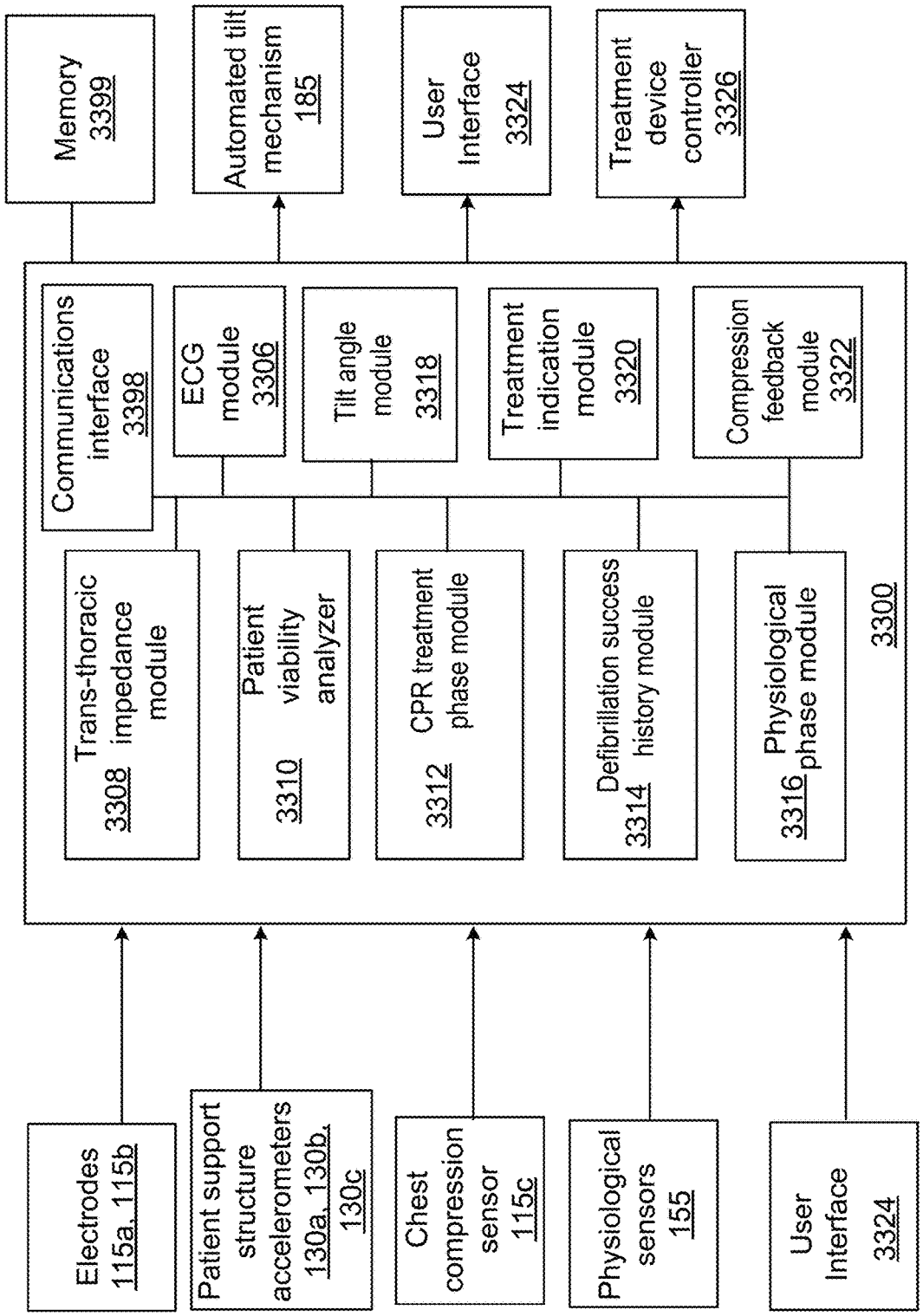
FIG. 3B is a schematic diagram of a processor for use with the system shown in FIG. 1.

Referring to FIG. 3B, a schematic diagram of an example of a processor for use with the system shown in FIG. 1 is shown. For example, the processor 3300 is a processor for use with the system 100. The processor 3300 is an example of a processor 1910 as described below with regard to FIG. 19. In an implementation, the electronic circuitry implementing the functions of the processor 3300 as described herein may be disposed only in the defibrillator 112. Alternatively, the electronic circuitry implementing the functions of the processor 3300 as described herein may be distributed over one or more processors included in one or more devices of the system 100. For example, the one or more devices may include the tilt controller 180, the defibrillator 112, the local computing device(s) 160, the remote computing device 119, the CC device 104, the electrode assembly 115, and the therapeutic delivery devices 158. One or more of these devices may be communicatively coupled via wired and/or wireless connections. Thus output from the processor 3300 may be the outcome of a decision process performed at a single device in the system 100 or in a combination of devices in the system 100. For example, in an implementation, the output from the processor 3300 may be the outcome of a decision process at the defibrillator 112 alone or in combination with decision processes performed at one or more pieces of ancillary equipment (e.g., the local computing device(s) 160, the remote computing device 119, the CC device 104, the electrode assembly 115, and the therapeutic delivery devices 158).

As an example, one or more of the defibrillator 112, the local computing device(s) 160, the remote computing device 119, the CC device 104, the electrode assembly 115, and the therapeutic delivery devices 158 devices may be coupled to and may communicate with one another via the network 118. Communications between these devices may include transmission and reception of CPR data. The CPR data may include data associated with the performance of the care provider 106 and/or data associated with the response of the patient 102 to CPR. The CPR data may include data from one or more of the electrode package 115 and/or the other suitable sensor(s) 155. The data may include CPR data associated with particular tilt angles 109a, 109b, 109c, and 109d. A communicative connection to the remote computing device 119 may enable remote medical personnel to provide feedback to, evaluate, review operations of, and/or control the personnel and/or equipment at the rescue scene.

The processor 3300 may receive sensor and/or user input from various input sources. For example, the various input source may include one or more of the electrodes 115a and 115b, the accelerometers 130a, 130b, and/or 130c and/or other accelerometers associated with the patient support structure 108, the chest compression sensor 115c, the physiological sensors 155, and a user interface 3324. The processor 3300 may receive the input via wired and/or wireless connections to the input sources.

The user interface 3324 may capture input from the care provider. The user interface 3324 may include input/output devices such as, for example, a display, a touchscreen, a keyboard, a mouse, a joystick, a microphone, a speaker, a haptic device, etc. The user interface 3324 may also provide feedback and/or other information for the care provider. For example, the user interface 3324 may provide visible, audible, and/or haptic information. The user interface 3324 may include a graphic user interface (GUI). The user interface 3324 may include one or more input/output devices disposed on and/or associated with one or more of the defibrillator 112, the local computing device(s) 160, the CC device 104, the electrode assembly 115, and therapeutic delivery devices 158.

In an implementation, the processor 3300 may receive one or more signals from one or more accelerometers 130a, 130b, and 130c associated with the patient support structure 108. Three-axis accelerometers affixed to one or more of sections 108a, 108b, and 108c may provide a signals indicative of a current amount of tilt of that particular patient support section relative to the direction of gravity.

In various implementations, the processor 3300 may include one or more of an ECG module 3306, a trans-thoracic impedance module 3308, a patient viability analyzer 3310, a CPR treatment phase module 3312, a defibrillation success history module 3314, a physiological phase module 3316, a tilt angle module 3318, a treatment indication module 3320, and a compression feedback module 3322. These modules are communicatively coupled (directly and/or indirectly) to each other for bi-directional communication. Although shown as separate entities in FIG. 3B, two or more of these modules may be combined. As used herein, the term module refers to appropriate electronic circuitry configured to implement instructions stored in a memory 3399 (e.g., the memory 1920 as described below with regard to FIG. 19) in order to perform the functions described herein.

The ECG module 3306 may combine data from different leads (e.g., 3 lead, 12 lead) to construct an ECG signal that is representative of the patient's ECG pattern. For example, the electrodes 115a and 115b may include leads for obtaining ECG data (e.g., via a 12-lead arrangement) and providing such data to the processor 3300. The ECG signal may also be represented mathematically as a vector value, such as including vector components in an XYZ representation. Such an ECG signal is often used to generate a visual representation of the patient's ECG pattern on a screen of the defibrillator 112 (e.g., the ECG waveform 310). The ECG-related data may also be analyzed in various ways to learn about the current condition of the patient, including in determining what sort of shock indication to provide to control the defibrillator 112 or to display to the care provider 106.

The trans-thoracic impedance module 3308 may determine trans-thoracic impedance information based on signals received from the electrodes 115a and 115b. The trans-thoracic impedance information indicates the impedance of the patient 102 between the locations of the electrodes 115a and 115b.

The patient viability analyzer 3310 may receive physiologic signals from physiologic sensors such as ECG, pulse oximetry, capnography, etc. If the physiologic signals are ECG, the ECG signals may be received from the electrodes 115a and 115b via the ECG module 3306. In an implementation, the patient viability analyzer 3310 may use ventricular waveform measures such as, for example, but not limited to, amplitude spectrum area (AMSA) and/or median slope. The patient viability analyzer 3310 may nearly continuously and repeatedly compute the patient viability estimate. The patient viability estimate is a score, such as, for example, an AMSA number or similar indicator, that represents ECG amplitude at particular different frequencies and/or frequency ranges in an aggregated form (e.g., a numeral that represents a value of the amplitude across the frequencies). In some implementations, power spectrum area may be measured and its value may be used as an input that is alternative to, or in addition to, an AMSA value for purposes of making a shock indication. The tilt angle module 3318 may use at least one of the current or past patient viability estimates to determine one or more of the tilt angles 109a, 109b, 109c, and 109d based on a cardiac phase.

Additionally or alternatively, the patient viability analyzer 3310 may use medical premonitory event estimation to calculate the patient viability estimate. A medical premonitory event is a future medical event. The patient viability analyzer 3310 may calculate the patient viability estimate based on a detection and/or estimation of medical premonitory events. For example, the analyzer 3310 may monitor physiological indicators from the patient (e.g., ECG signals and other cardiac parameters, respiratory parameters, etc.) and detect and/or estimate medical premonitory events (e.g., elevated risk of cardiac events) for the patient based on received physiological indicators. The physiological indicators are provided to the processor 3300 by one or more of the electrodes 115a, 115b, the physiological sensors 155, and the user interface 3324. As used herein, "premonitory" refers to an indication that something has a likelihood or probability of occurring, and a "medical premonitory event" refers to a medical event that has a likelihood or probability of occurring for the monitored patient. The detection and estimation of medical premonitory events may thus be used as an early warning system to provide the patient, a bystander, and/or a medical professional time to prepare for the predicted medical event. For example, the patient, a bystander, and/or a medical professional may prepare for a potentially adverse or fatal degradation in the medical condition of the patient, to potentially mitigate or avoid the adverse effects of the degradation, or even potentially completely avoid the degradation or event with timely, appropriate treatment. Example methods and systems for medical premonitory event estimation are disclosed in issued U.S. Patent Application Publication No. 2016/0135706, entitled "Medical Premonitory Event Estimation," the contents of which are incorporated by reference in their entirety herein.

Non-limiting examples of medical events include, for example, cardiac events such as a myocardial infarction or cardiac arrest, profound bradycardia due to acute decompensated heart failure, acute coronary syndrome, etc. Non-limiting examples of degradation in medical condition may include inception of a disease state, progression or worsening of a disease state, and/or an adverse medical event, such as arrhythmia, heart attack, a subject suffering from traumatic injury that undergoes a potentially fatal, rapid loss in blood pressure due to hard-to-detect internal bleeding. Other possible medical events or degradations in the medical condition of a subject may be due to physical injury, diabetes, septic shock, seizure or epilepsy, for example.

Non-limiting examples of medical premonitory events (e.g., as detected by the patient viability analyzer 3310) may include ectopic beats, runs of ectopic beats, ventricular tachycardia, bradycardias, and/or irregularities or abnormalities in P wave, QRS complex, T wave and U wave. Such events may be tangible events that are detectable by a trained clinician. Irregularities or abnormalities in electrical activity of the heart can include flattened T waves, inverted T waves, hyper-acute T waves or peaked T waves, beat-to-beat T wave variability, shortened QT interval, prolonged QT interval, wide QRS, prominent U waves, etc. Alternatively or additionally, medical premonitory events may include intermediate level events, such as the detection of clusters of events, accelerations of event rates, an increase in intensity or criticality of events, etc. Alternatively or additionally, medical premonitory events may include higher order events that may, for example, be defined in a multidimensional parameter space, e.g., the parameters comprising electrocardiogram ("ECG") data and/or other relevant physiologic parameters and/or patient demographics and other health history.

The CPR treatment phase module 3312 may receive and process signals from the chest compression sensor 115c and may provide an indication of a determined phase of CPR treatment. Additionally or alternatively, the CPR treatment phase module 3312 may receive and process signals from the physiological sensors 155 and/or the electrodes 115a and 115b (e.g., via the ECG module 3306) to provide the indication of the determined phase of CPR treatment. The phase of CPR treatment may correspond to one or more of an elapsed time of CPR treatment, a number of delivered CPR compressions, a number of delivered CPR ventilations, a number of delivered defibrillation shocks, an interval within a compression cycle (e.g., compression, decompression, hold time, release, etc.), or another portion of CPR treatment identifiable based on chest compression data from input to the CPR treatment phase module 3312.

For example, a first phase of CPR treatment may include a first compression therapy including at least 30 seconds of chest compressions and a second phase of CPR treatment may include a second compression therapy including at least 30 seconds of subsequent chest compressions. The CPR treatment phases may be delineated by the occurrence of one or more of a series of stacked defibrillation shocks, e.g.: the first CPR treatment phase with a duration of approximately 30 seconds to 5 minutes, followed by a first defibrillation shock, followed by the second CPR treatment phase with a duration of approximately 30 seconds to 5 minutes, followed by a second defibrillation shock, and so on. These phase durations are examples only and the first phase of CPR treatment may be longer than or shorter than the second phase of CPR treatment.

A defibrillation success history module 3314 may track the application of defibrillation shocks to the patient, the success of the defibrillation shocks in defibrillating the patient, and/or the level to which the defibrillation shock was successful. For example, the module 3314 may monitor the ECG waveform, as provided by electrodes 115a and 115b via the ECG module 3306. The module 3314 may analyze the ECG waveform in time windows of various sizes for a rhythm that matches a profile of a normal heart rhythm. The normal heart rhythm is a heart rhythm that a heart rhythm analysis algorithm and/or medical practitioner would evaluate as counter-indicative of defibrillation and/or other cardiac resuscitative treatment or intervention. If the normal rhythm is determined to be established for a predetermined time period after the application of a defibrillation shock, the module 3314 may register the existence of a successful shock. If a defibrillation shock is applied and a normal rhythm is not established within a time window after the delivery of the shock, the module 3314 may register a failed shock.

In addition to registering a binary value of success/fail, the module 3314 may further analyze the ECG signals from the ECG module 3306 to determine the level of the success or failure of each shock. The module 3314 may, for example, assign a shock success score indicative of the chance of success of each shock. In an implementation, the shock success score may be a normalized score between 0 (no chance of success) and 100 (absolute certainty of success). For example, the defibrillation shock may not have resulted in an organized rhythm, such as normal sinus, and the ECG rhythm may still indicate ventricular fibrillation. However, the patient viability estimate may show an improved state of the patient following the defibrillation shock. In another example, the defibrillation shock may have converted the patient's ECG to an organized, perfusing rhythm, but medical premonitory event estimation scores may show that the organized rhythm may not be stable and may have a high risk of degenerating into a life threatening rhythm. Thus, these scores may be used to determine the level of success or failure of the shock.

A physiological phase module 3316 may measure a physiological signal from one or more of the electrodes 115a and 115b (e.g., via the ECG module 3306) and/or the physiological sensors 155. The physiological phase module 3316 may determine a physiological phase of the patient 102 based on the measured physiological signal.

The physiologic phases may be the general phases of cardiac arrest or VF and may be identified, in one representation, as three separate phases (though there may be some overlap at the edges of the phases): electrical, circulatory, and metabolic. The electrical phase is the first several minutes of an event, and marks a period during which electric shock may be particularly effective in defibrillating the victim's heart and returning the victim to a relative satisfactory condition. Given the greater viability of the patient and the generally better vascular tone, the tilt angle may be set to a higher value, e.g. 10 degrees higher, than for the circulatory or metabolic phases.

The circulatory phase appears to mark a decrease in effectiveness for electric shock in defibrillating the victim, and particularly in the absence of chest compressions performed on the victim. As a result, a device such as a portable defibrillator may be programmed to stop advising shocks during such a phase (or may advise a shock only when other determinations indicate that a shock would be particularly likely to be effective) and may instead advise forceful CPR chest compressions, such as with both active decompression and an increased tilt angle. Such forceful compressions may maximize blood flow through the heart tissue and other parts of the body so as to extend the time that the victim may survive without lasting or substantial damage, while at the same time minimizing intracranial pressures (ICP).

In the metabolic phase, chest compressions may be relatively ineffective as compared to the circulatory phase. For example, where tissue has become ischemic, such as in circulatory phase, the tissue may react favorably to the circulation of blood containing some oxygen, but where tissue has become severely ischemic, such as in metabolic phase, the introduction of too much oxygen may be harmful to the tissue. As a result, more gentle compressions with a lower tilt angles, e.g. 10 degrees, for the first period, such as 30 seconds, may need to be advised in the metabolic phase before the rescuer (or a mechanical chest compressor controlled to provide appropriate levels of compression following the points addressed here) uses a full force. Other treatments that may be useful in the metabolic phase include extracorporeal circulation and cooling, either alone, in combination with each other, or in combination with other pharmacological treatments. In any event, observation of elapsed time since an event has begun and/or observation of the phase in which a victim is in, may be used to control a device or instruct a rescuer to switch from a first mode of providing care to a second mode of providing care in which the parameters of the provided care differ (e.g., speed or depth of chest compressions may change, temperature-based therapy may be provided or stopped, or pharmaceuticals may be administered).

The measured physiological signal may include one or more of ECG, invasive blood pressure, non-invasive blood pressure, such as using oscillometric methods, non-invasive using tonometric methods, pulse oximetry, capnography, near infrared spectroscopy (NIRS), impedance cardiography, impedance pneumography, heart sounds, lung sounds, cerebral oxygenation to name a few examples. The determined physiological phase of the patient 102 may include a type of cardiac event experienced by the patient. The determined type of cardiac event experienced by the patient may include one or more of a cardiac arrest, an arrhythmic etiology, a cardiogenic shock etiology, and a respiratory arrest of pulmonary etiology. The determined physiologic phase in some examples, may be the detection of a change of a particular physiologic parameter as determined by one or more of the physiologic signals, e.g. blood pressure, blood flow, heart rate, respiration rate, ECG QRS width. For instance, if the amplitude of a physiologic parameter changes by more than a specified threshold in a specified period of time, then the physiologic phase may be determined to have changed. For example, a specified threshold for a blood pressure change may be in a range of 0-20% so a blood pressure increase of 22% may indicate a change in a physiologic phase.

Figure 18:
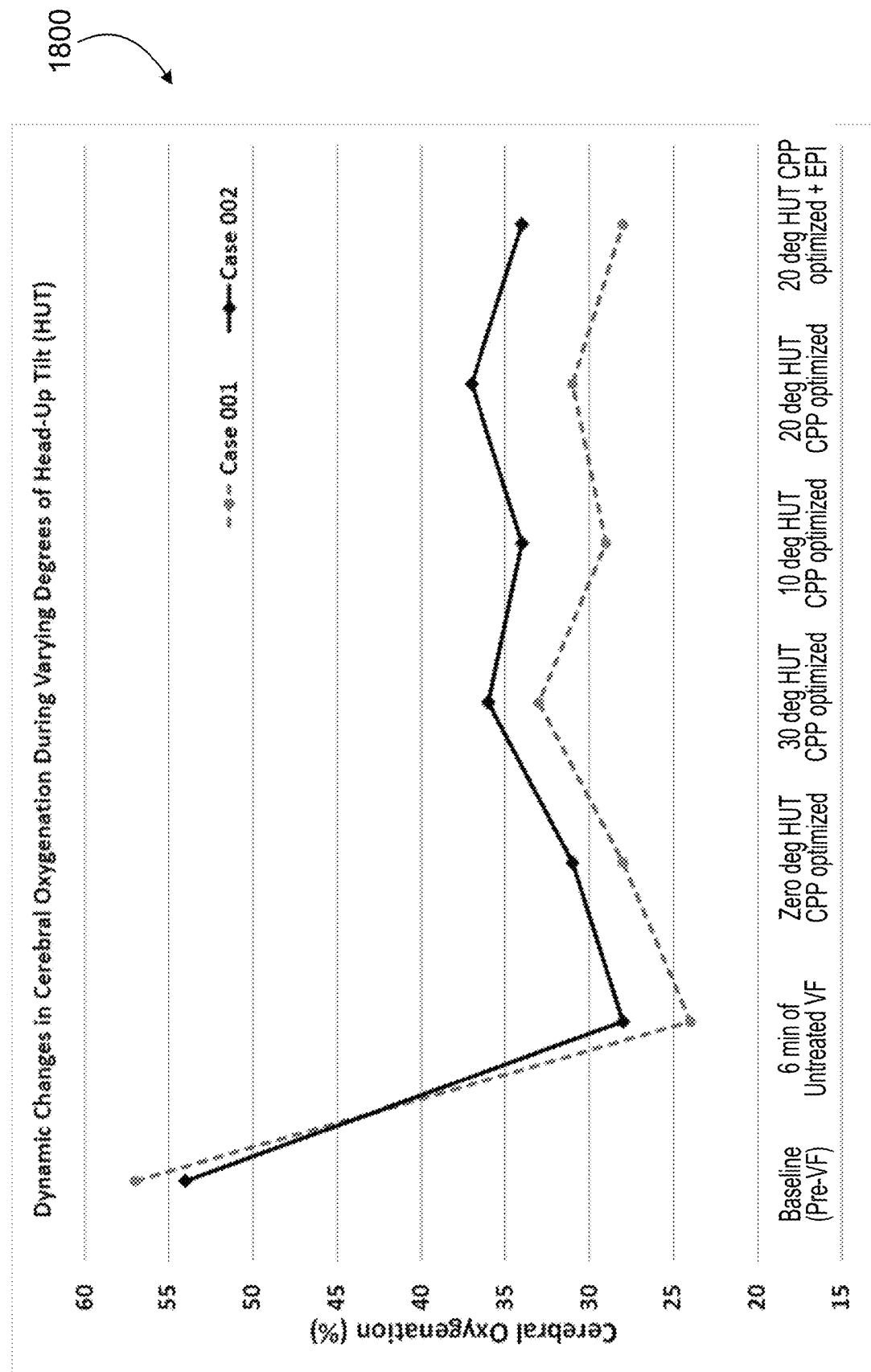
FIG. 18 shows a plot of experimental data obtained from swine administered CPR treatment at various degrees of tilt angles.

For instance, the tilt angle module 3318 might set the angle arbitrarily to 30 degrees, measure the cerebral oxygenation, then adjust to only 10 degrees and measure the cerebral oxygenation again to see if there was a change in physiologic phase (i.e. decrease or increase in cerebral oxygenation). If there is a change in physiologic phase, e.g. a decrease in cerebral oxygenation, as shown in FIG. 18, then the tilt angle module 3318 may increase the tilt angle, e.g., to 20 degrees.

The tilt angle module 3318 may determine a recommended tilt angle (e.g., one or more of the tilt angles 109a, 109b, 109c, and/or 109d) based on input to the processor 3300. The input to the processor 3300 may include sensor input and/or user input. The tilt angle module 3318 may determine the tilt angles by analyzing the three-axis accelerometer input signals using a trigonometric calculation. For example, for the first phase of the CPR treatment, the tilt angle module 3318 may determine one or more first recommended tilt angles (e.g., the one or more first tilt angles may correspond to one or more of the support sections 108a, 108b, and 108c). For the second phase of the CPR treatment, the tilt angle module 3318 may determine one or more second recommended tilt angles (e.g., the one or more second tilt angles may correspond to one or more of the support sections 108a, 108b, and 108c). In various implementations, one or more of the one or more first tilt angles may be less than, equal to, or greater than one or more of the one or more second tilt angles. The one or more first tilt angles may be between 10 and 20 degrees or may be between 20 and 30 degrees. The one or more second tilt angles may be between 10 and 20 degrees or may be between 20 and 30 degrees. The determined tilt angle may be less than, equal to, or greater than an existing tilt angle. In an implementation, the tilt angle module 3318 may determine a rate of angle adjustment. For example, the rate of angle adjustment may be between approximately 1-5 degrees per second, between approximately 5-10 degrees per second, or between 1-10 degrees per second.

In an implementation, the physiological sensors 155 may provide physiological signal input to the processor 3300. For example, as discussed herein, physiological signals such as, for example, but not limited to, cerebral oxygenation, blood pressure, and blood flow may provide an indication that the head and/or the heart should be elevated or lowered relative to another part of the body. Accordingly, the tilt angle module 3318 may process input from the physiological sensors 155 and output one or more of the tilt angles 109a, 109b, 109c, and 109d.

In some implementations, the tilt angle module 3318 may use one type of data used, or may combine multiple types of data (e.g., by giving a score to each type and a weight, and combining them all to generate a weighted composite score) to determine the suggested tilt angle. The input data may include multiple factors, such as a physiological signal, a physiological phase, a phase of CPR treatment, or another input that provides insight for patient treatment.

One or more of the particular factors discussed here may be fed to the tilt angle module 3318, which may combine them each according to an appropriate formula so as to generate a binary or analog shock indication. For example, any of the following appropriate steps can be taken: a score can be generated for each of the factors, the scores may normalized, a weighting can be applied to each of the scores to represent a determined relevance of that factor to the predictability of a shock outcome, the scores can be totaled or otherwise combined, and a defibrillation shock indication can be determined such as a go/no go indication, a percentage of probability of treatment's success at a particular tilting configuration, and other such indications.

In this manner then, the tilt angle module 3318 may take into account one or a plurality of factors in determining suggested tilt angle. The factors may take data measured form a plurality of different inputs (e.g., ECG, trans-thoracic impedance, delivered agents, etc.), and can be combined to create a likelihood indication, such as a numerical score that is to be measured against a predetermined range (e.g., 0 to 45 degrees). Such determination may then be used to control an automatically-operated patient support structure, to limit operation of a manually-operated patient support structure, or by simply providing information to patient support structure whose tilt angle is determined solely by a care provider.

In an implementation, the tilt angle module 3318 may determine the recommended tilt angle for one or more CPR treatment phases as determined by the CPR treatment phase module 3312. Additionally or alternatively, the tilt angle module 3318 may determine the recommended tilt angle based on input from one or more of the modules 3306, 3308, 3310, 3314, 3316, 3320, and 3322.

The treatment indication module 3320 may use the score and/or the success or failure of each shock to generate a treatment indication. The treatment indication may be a type of CPR treatment during a phase. Some examples of the various types of CPR treatments occurring in the phases include, but are not limited to, standard compressions, supine chest compressions, heads up chest compressions, heads up chest compressions at various angles, and chest compressions with active decompression. For example, for an organized rhythm that has a low score (e.g. less than 50), the treatment selection might be chest compressions, or chest compressions synchronized to the intrinsic activity of the heart. For synchronized chest compressions, the start of a chest compression and the duration of the chest compression may be adjusted to improve patient outcomes and improve the efficacy of the chest compressions or other phasic therapy. The adjustments may be, based on sensor signals indicative of a patient condition or physiologic parameter during one or more prior chest compressions. The sensor signals may, for example, indicate a rate or amount of cardiac ejection or filling, cardiac output or other indicator of mechanical activity of the heart or arterial blood flow. The treatment indication module 3320 may generate a treatment indication configured to vary the synchronized phasic therapies, e.g., chest compressions, and vary the application of the therapies. By varying the therapies and their application and subsequently re-measuring the sensor signals, the treatment indication module 3320 may determine which synchronized therapy, or therapies, and pattern of synchronized therapy is most effective to improve cardiac ejection, cardiac output or otherwise improve the condition of the patient. For example, the treatment indication module 3320 may vary each of the synchronized therapies and combinations of therapies to determine which pattern of therapy or therapies when synchronized with residual myocardial synchronization results in the greatest measured cardiac output or results in some other measurable condition that indicates acceptable efficacy of the applied phasic therapy(ies).

In an implementation, the treatment indication may be a particular tilt angle for one or more patient support sections (e.g., 108a, 108b, 108c, 1002a) and/or may be a recommended change in one or more tilt angles. The recommended change in the tilt angle may be a recommendation to increase or decrease one or more tilt angles by a certain number of degrees or a recommendation to increase or decrease the one or more tilt angles to reach a target angle. The treatment indication may include an identification of the particular patient support sections for which the tilt angle needs to change.

Additionally or alternatively, the treatment indication module 3320 may use a current AMSA value to determine a treatment selection. Some additional examples of treatment selections include, but are not limited to, drug infusion, ventilation, defibrillation, electrotherapy, pacing, chest compression (manual or automated) or other treatments provided by the therapeutic devices 158. In some implementations, the treatment indication module 3320 may use one type of data used, or may combine multiple types of data (e.g., by giving a score to each type and a weight, and combining them all to generate a weighted composite score) to determine the suggested treatment. The input data may include multiple factors, such as a physiological signal, a physiological phase, a phase of CPR treatment, or another input that provides insight for patient treatment.

The compression feedback module 3322 may analyze chest compression information (e.g., signals received from the chest compression sensor 115c) to determine the efficacy of the CPR treatment. The compression feedback module 3322 may compare the chest compression information to protocols to determine feedback for the care provider 106 and/or for the CC device 104. In an implementation, the compression feedback module 3322 may evaluate the chest compression information in conjunction with information determined by one or more of the modules 3306, 3308, 3310, 3312, 3314, 3316, 3318, and 3320 to determine the feedback. Additionally or alternatively, the compression feedback module 3322 may analyze signals from one or more of the electrodes 115a, 115b, the user interface 3324, and/or the physiological sensors 155 to determine the feedback.

The compression feedback module 3322 may provide real-time feedback for the care provider 106. For example, the processor 3300 may provide prompts to the user interface 3324 to guide the care provider 106 in performing each phase of the CPR treatment. The prompt may include at least one of an audio prompt, a verbal prompt, a non-verbal prompt, a visual prompt, a graphical prompt and a haptic prompt. The prompts may further include an audible, visible and/or haptic metronome. The metronome may guide the care provider 106 to perform each phase of CPR treatment at the appropriate rate. The process of observing a component of the CPR, such as the response of the patient at particular tilt angles, may continue recursively as long as care is being provided to the patient 102.

The processor 3300 may output the determined tilt angles and this output may be an input to one or more of the automated tilt adjuster 185, the user interface 3324 (e.g., a user interface associated with one or more of the defibrillator 112, the CC device 104, the electrode assembly 115, the therapeutic delivery devices 158, and the local computing device(s) 160), and the treatment device controller 3326. The treatment device controller 3326 includes one or more control systems associated with one or more of the CC device 104, the defibrillator 112, and the therapeutic delivery devices 158. The treatment device controller 3326 may control one or more operations of the respective treatment device for providing treatment to the patient, receiving data from the patient, and/or receiving/transmitting data to/from other devices in the system 100. In response to this output, for example, the tilt controller 180 may automatically adjust a position of one or more of the support sections of the patient support structures 108, 1000, 1100, 1200, and/or 1300 based on the determined tilt angles. As another example, the user interface 3324 may display, or otherwise make available to the care provider 106, the determined tilt angles. The care provider 106 may then manually adjust the positions of support sections for the patient support structures 108, 108, 1000, 1100, 1200, and/or 1300 based on the determined tilt angles.

As another example of output, the processor 3300 may generate an output for the care provider that the head of the patient should be raised from 10 degrees to 20 degrees relative to the horizontal axis. The care provider 106 may provide an input (e.g., pressing a button, adjusting a dial, providing a voice command, etc.) to confirm acceptance of the recommendation, to adjust the degree of elevation (e.g., to 15 degrees or 30 degrees, or 5 degrees), to refuse the recommendation, or may ignore the suggestion altogether. In an implementation, if the suggestion is ignored by the care provider 106 within a present time interval, the processor 3300 may instruct the tilt controller 180 to proceed with adjusting the tilting configuration of the patient support structure 108 according to the recommended elevation/tilt adjustment, or conversely, the processor 3300 may halt execution of the recommended elevation/tilt adjustment. The processor 3300 and/or the tilt controller 180 may perform automated tilt control independent of or may require input from the care provider 106.

In an implementation, the control software and/or firmware for the tilt controller 180 and/or the processor 3300 may include pre-programmed recommended angles and/or angular ranges. These pre-programmed angles may be adjustable by the care provider via input to the tilt controller 180 and/or the processor 3300 and/or via software updates to these devices with regard to patient care protocols.

The processor 3300 may include a communications interface 3398. The communications interface 3398 may transmit and/or receive information from and/or at the computing device that includes the processor 3300. The communications interface 3398 may transmit and/or receive the information via wired and/or wireless communicative interconnections between two or more of the remote computing device 119, the therapeutic delivery device(s) 158, the sensors 155, the defibrillator 112, the local computing device(s) 160, and the CC device 104. Further, the communications interface 3398 may transmit and/or receive the information via wired and/or wireless communicative connections between the network 118 and one or more of the remote computing device 119, the therapeutic delivery device(s) 158, the sensors 155, the defibrillator 112, the local computing device(s) 160, and the CC device 104. The communications interface 3398 may provide Wi-Fi, Bluetooth®, satellite, and/or cellular communications capabilities. The information transmitted and/or received may include information stored in the memory 3399. The information may include, for example, but not limited to, resuscitative treatment information (e.g., impedance information, AMSA information, CPR treatment phase information, defibrillation success information, physiological phase information, compression feedback, ECG information, etc.), tilt angle information, treatment indication information, patient information, rescuer information, location information, rescue and/or medical treatment center information, etc.

As an example, referring again to FIG. 3A, a box 322 on a display of the defibrillator 112 may include an indication of a change in the suggested tilt angle of different portions of the patient's body (e.g., head, torso, and/or lower body). Adjustment of the patient's tilting configuration to recommended angles may improve vascularization and cerebral oxygenation during CPR treatment.

As shown on display 302, during the administration of chest compressions, the defibrillator 112 may display information about the chest compressions along with a filtered ECG waveform 310 and a CO2 waveform 312 (or alternatively an SpO2 waveform). As shown in display 302, the filtered ECG waveform 310 is a full-length waveform that fills the entire span of the display device, while the second waveform (e.g., the CO2 waveform 312) is a partial-length waveform and fills only a portion of the display. A portion of the display beside the second waveform provides the CPR information in box 314. For example, the display splits the horizontal area for the second waveform in half, displaying the waveform 312 on the left, and CPR information on the right in box 314.

During chest compressions, the defibrillator 112 may generate the filtered ECG waveform 310 by gathering ECG data points (e.g., from EEG electrodes 1YY) and chest compression data (e.g., from chest compression sensor 1GG) and filtering the motion-induced (e.g., CPR-induced) noise out of the ECG data. The defibrillator 112 may further determine chest displacement, velocity and/or acceleration of chest compression during chest compressions based on the chest compression data. Displaying the filtered ECG waveform 310 may help the care provider 106 to reduce interruptions in CPR because the displayed waveform is easier for the care provider to decipher than an unfiltered ECG waveform. If the ECG waveform is not filtered, artifacts from chest compressions may make it difficult to discern the presence of an organized heart rhythm unless compressions are halted. Filtering out these artifacts may allow care providers to view the underlying rhythm without stopping chest compressions.

The defibrillator 112 may automatically display the CPR information in box 314 when the defibrillator detects compressions based on signals from the chest compression sensor 1GG. The CPR information in box 314 may include rate 318 (e.g., number of compressions per minute) and/or depth 316 (e.g., depth of compressions in inches or millimeters). Displaying the tilt angle of a patient support section, as well as the actual rate and depth data (in addition to, or instead of, an indication of whether the values are within or outside of an acceptable range) may provide useful feedback to the care provider. For example, if an acceptable range for chest compression depth is 2.0 to 2.4 inches (in accordance with guidelines provided by the American Heart Association), providing the care provider with an indication that his/her compressions are only 0.5 inches may allow the care provider to determine how to correctly modify his/her administration of the chest compressions (e.g., he or she may know how much to increase effort, and not merely that effort should be increased some unknown amount).

The CPR information in box 314 may also include a perfusion performance indicator (PPI) 320. The PPI 320 is a shape (e.g., a diamond) with the amount of fill that is in the shape differing over time to provide feedback about both the rate and depth of the compressions. When CPR is being performed adequately, for example, at a rate of about 101 compressions per minute (CPM) with the depth of each compression greater than 1.5 inches, the entire indicator will be filled. As the rate and/or depth decreases below acceptable limits, the amount of fill lessens. The PPI 320 provides a visual indication of the quality of the CPR such that the care provider 106 can aim to keep the PPI 320 completely filled.

Also shown on the display is a reminder 321 regarding "release" in performing chest compression. Specifically, a fatigued care provider 106 may lean forward on the chest of the patient 102 victim and not release pressure on the sternum at the top of each compression. This may reduce the perfusion and circulation accomplished by the chest compressions. The defibrillator 112 may display the reminder 321 when the defibrillator 112 recognizes that release is not being achieved (e.g., signals from the chest compression sensor 1GG show an "end" to the compression cycle that is flat and thus indicates that the care provider 106 is leaning on the sternum to an unnecessary degree). The defibrillator 112 may coordinate such a reminder with other feedback. Further the defibrillator 112 may provide this reminder as one or more of visual indication on the defibrillator 112, additional visual feedback on a display near the care provider's hands, and spoken and/or tonal audible feedback. The audible feedback may include a sound that differs sufficiently from other audible feedback so that the care provider will understand that release (or more specifically, lack of release) is the target of the feedback.

The defibrillator 112 may modify the displayed CPR information based on the actions of the care provider 106. For example, the data displayed may change based on whether the care provider is currently administering CPR chest compressions to the patient. Additionally, the ECG data displayed to the user may change based on the detection of CPR chest compressions. For example, an adaptive filter may automatically turn ON or OFF based on detection of whether CPR is currently being performed. When the filter is on (during chest compressions), the filtered ECG data is displayed and when the filter is off (during periods when chest compressions are not being administered), unfiltered ECG data is displayed. An indication of whether the filtered or unfiltered ECG data is displayed can be included with the waveform.

In an implementation, the defibrillator 112 may use particular data analysis techniques to improve the quality of CPR treatment. For instance, the defibrillator 112 may determine the feedback discussed above by selecting an appropriate ECG window size for calculating amplitude spectrum area (AMSA) on vectorized values (e.g., one second or slightly longer, such as 1.5 seconds or 2 seconds), a window type (e.g., Tukey), and particular coefficients for the window. Such factors may also be changed over the time of a VF event, as discussed above, so as to maintain a most accurate determination of suggested tilt angles.

While at least some of the embodiments described above describe techniques and displays used during manual human-delivered chest compressions, similar techniques and displays may be used with automated chest compression devices such as the AUTOPULSE® device manufactured by ZOLL® Medical Corporation of Chelmsford, Mass.

In addition to providing defibrillation, the defibrillator 112 may serve as a patient monitor via a variety of patient sensors and/or patient chest compression sensors. For example, the defibrillator 112 may detect and process a physiological parameter that may be used to determine the tilting configuration of the patient support structure 108. The physiological parameter may include at least one of a measured physiological signal and a determined physiological phase of the patient. For example, the physiological signal may be measured by one or more patient sensors coupled to a portion of the body of the patient 102. The one or more patient sensors may include the defibrillation electrode assembly 115 and/or other sensor(s) 155 configured to provide information for assisting in providing resuscitative treatment to the patient 102. For clarity, these physiological sensors 155 are represented by a box in FIG. 1 and shown as optionally coupled to one or more of the defibrillator 112 and the patient 102. These physiological sensors 155 may include, for example electroencephalogram (EEG) electrodes, a motion sensor, a force sensor, an airflow sensor, a pressure sensor, an ultrasound transducer, an ophthalmoscope, an optical sensor, and a carbon dioxide gas sensor.

As an example, an airflow sensor may be coupled to a ventilation bag 114. The care provider 106 may assist patient's ventilation using the ventilation bag 114 and/or performing abdominal compressions, for example, synchronized with chest compressions. Abdominal compressions and/or ventilations may also be applied as an intervention in conjunction with elevation of the patient's upper body. That is, it may be beneficial to the patient to apply abdominal compressions, or to bind the abdomen of the patient, during certain phases of elevation. For example, when the patient's head is elevated to a substantial degree (e.g., approximately 30 degrees), there may be a tendency for portions of the torso to become distended, or blood may collect in an undesirable manner below the heart. Accordingly, it may be preferable to provide a suitable amount of pressure on the abdomen so that blood is less likely to accumulate away from other parts of the body (e.g., vital organs, heart, and brain). In some implementations, the configuration and geometry of the patient support structure 108 enables the care provider to use the same body position and compression technique as in standard CPR.

Figure 4A:
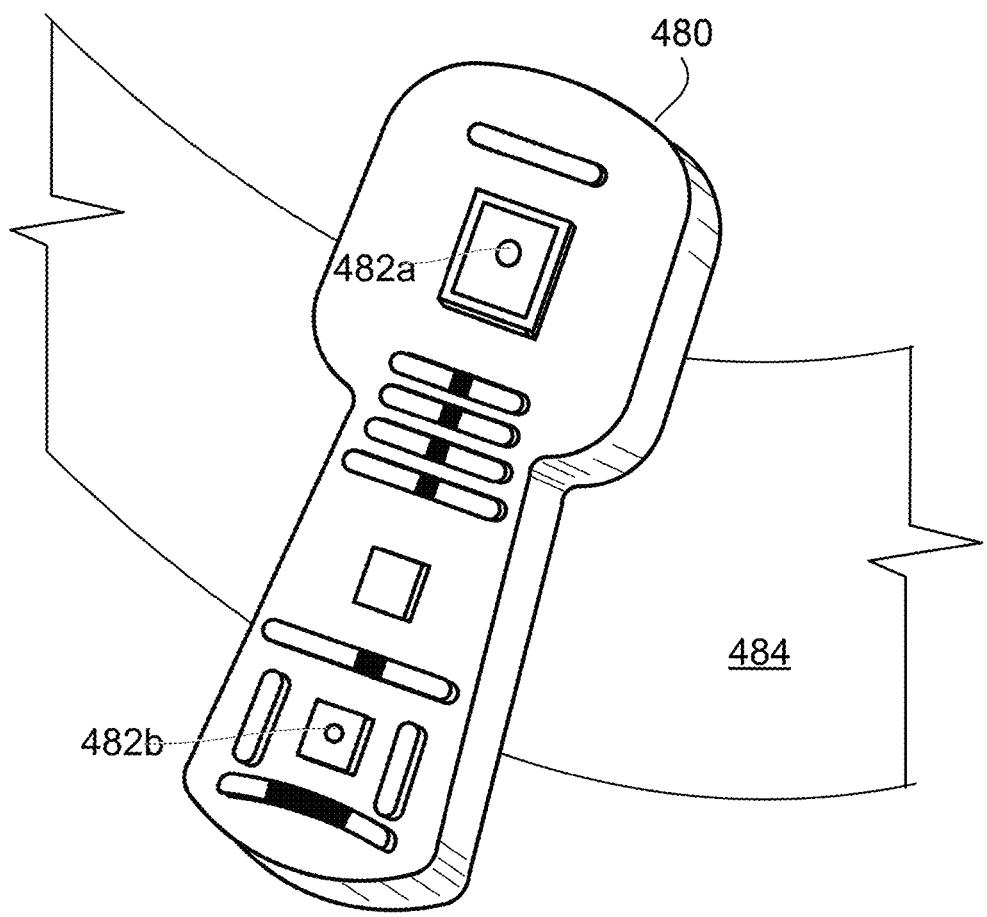
FIGS. 4A and 4B are schematic diagrams of an example of an oximetry sensor.
Figure 4B:
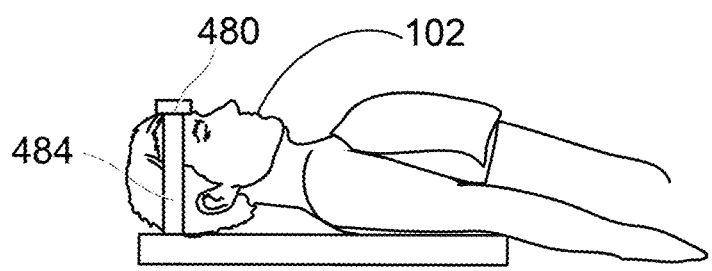

As another example, the optical sensor may be an oximetry sensor. Referring to FIGS. 4A and 4B, a schematic diagram of an example of an oximetry sensor is shown. The oximetry sensor may be configured as an oximeter probe, to measure oxygenation and/or blood pH for the patient 102. For example, the oximeter may be disposed on the patient's head (e.g., as shown in FIG. 4B to measure cerebral oxygenation) or other body part. In an implementation, the oximetry sensor 480 may be a near infrared spectroscopy (NIRS) sensor. To provide additional context, NIRS data may provide a substantially continuous non-invasive measure of hemoglobin saturation and systemic oxygenation. NIRS may further be used in transcranial cerebral oximetry to measure regional cerebral oxygen saturation.

NIRS is based on the principle of transmission and absorption of near infrared light (approximately 700-1000 nm) as it passes through tissue. The absorption of near infrared light is proportional to the concentration of iron in hemoglobin and copper in cytochrome aa4. Because oxygenated and deoxygenated hemoglobin have different absorption spectra, the oxygenation status may be determined. Oximeter probes typically include a fiber optic light source and light detector(s), where the fiber optic strands release light amplification by stimulated emission of radiation or light emitting diodes light. The emitted light wavelengths are sent from the light source penetrating the skull and cerebrum, and the light detector(s) receives the light not absorbed during the light pathway through the skull and cerebrum. The amount of oxygen present in the brain is the difference between the amount of light sent and received by the probe, which is often suggested by a percentage of oxygen provided to a user. A suitable oximetry sensor may be employed to detect and provide values of cerebral oxygenation, for example, spectral sensors manufactured by Nonin Medical Inc. in Plymouth, Minn., and CAS Medical Systems, Inc. (CASMED®) in Branford, Conn.

The oximetry sensor 480 includes a light source 482a (i.e., an emitter) and a light detector 482b. The care provider 106 may place the oximetry sensor 480 on the head of the patient 102. Typically, the oximetry sensor 480 is placed on regions where there is the least amount of interference. For example, the oximetry sensor 480 may be placed on a forehead or shaved area to eliminate or reduce interference from hair. Specifically, the oximetry sensor 480 may be placed on the lower forehead region, above the eyebrow with the sensor optics (e.g., the emitter 482a and the detector 482b) placed lateral of the iris and proximal the temple. In some implementations, the oximetry sensor 480 may include a headband 484. The headband 484 may be placed over the oximetry sensor 480 and is configured to secure the oximetry sensor 480 to the head of the patient 102, as illustrated in FIG. 4B. The care provider 106 and/or the defibrillator 112 may control the oximetry sensor 480 to obtain physiological parameters including, for example, a cerebral oxygenation percentage or a blood oxygen concentration.

Figure 5:
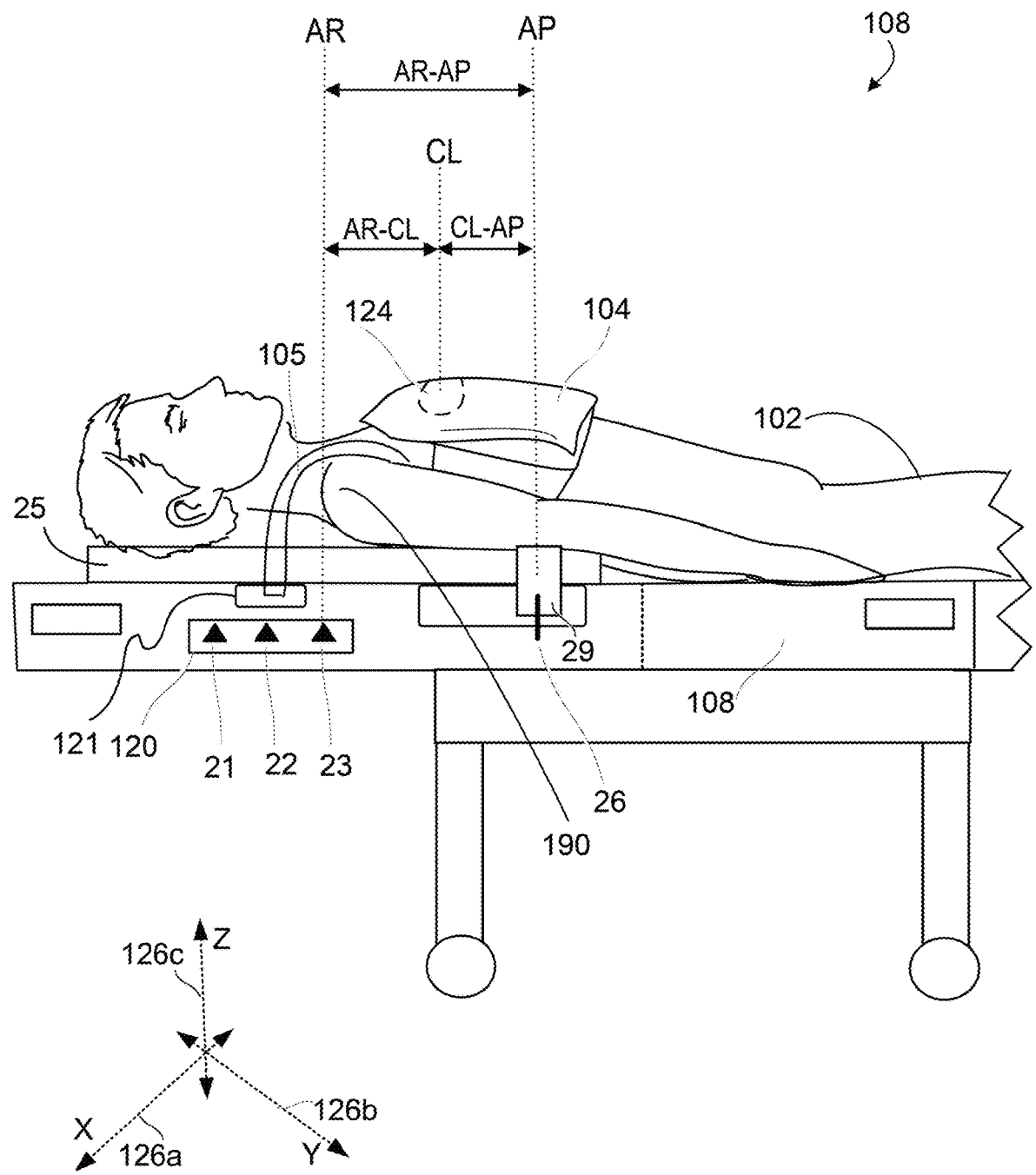
FIG. 5 is an illustration of examples of alignment features of the patient support structure shown in FIG. 1.

Referring to FIG. 5, with further reference to FIG. 1, an illustration of examples of alignment features of the patient support structure 108 are shown. In an implementation, the patient support structure 108 may include one or more alignment features 120. The alignment feature includes one or more indicators (e.g., the reference points 21, 22, 23) of a position of an anatomical reference point of the patient that will align the patient with the CC device 104 when the CC device 104 is coupled to the patient support structure 108. The care provider 106 may position the patient 102 on the patient support structure 108 relative to the alignment feature 120. The alignment feature 120 may be part of or attached to the patient support structure 108. For example, the indicators 21, 22, and 23 may be bumps, protrusions, markings, divots, a lighted indicator, or other indicia. In the example of FIG. 5, the anatomical reference point is a shoulder 190 of the patient 102 and the shoulder 190 is aligned with the indicator 23. However, this is an example only and the anatomical reference point may include at least one of an axilla, a sternal notch, a nipple line, or other anatomical feature of the patient. Using the alignment feature 120, the care provider may visually align the anatomical reference point and properly position the patient 102 on the patient support structure 108. The one or more indicators 21, 22, 23 show the position of the anatomical reference point of the patient such that when the CC device 104 is mounted on the patient support structure 108 the CC device 104 will provide chest compressions at a desired compression location 124 on the chest of the patient.

In an implementation, the patient support structure 108 may include an alignment strap 105. The alignment strap 105 is configured to extend from an axilla of the patient around the shoulder and attach to the patient support structure at an attachment point 121. The alignment strap 105 may help to hold the patient 102 in a position on the patient support structure 108.

Alignment of the anatomical feature with the alignment feature 120 and/or the alignment strap 105 may ensure that the patient is appropriately positioned on the patient support structure 108 so that the CC device 104 provides chest compressions at the desired compression location (CL) 124 on the patient 102 when the CC device 104 is coupled to the patient support structure 108. The desired compression location 124, on which to perform chest compressions may be the sternum. In various implementations, it may be desirable for compressions to occur at locations other than the sternum. If the patient 102 is improperly aligned relative to the CC device 104, the CC device 104 may perform compressions at an undesirable location (e.g., neck, abdomen) of the patient 102. The CC device 104 may adjustably couple to the patient support structure 108 via a mechanical coupling, as described in further detail below with regard to FIGS. 8, 9A, and 9B.

The point at which the CC device 104 is coupled is referred to as the affixation point (AP) 26. By aligning the anatomical reference (AR) of the patient 102 with the alignment feature 120, the CC device 104, coupled to the patient support structure 108 at AP 26, is positioned to apply chest compressions at CL 124. The alignment feature 120, the CC device 104, and the AP 26 are configured such that (AR-AP)=(AR-CL)+(CL-AP). In this relationship, (AR-AP) represents the distance between the anatomical reference for the patient and the AP 26, (AR-CL) represents the distance between the anatomical reference for the patient and the desired compression location 124 on the patient, and (CL-AP) represents the distance between the desired compression location 124 on the patient 102 and the AP 26. The alignment feature 120 may enable proper alignment of the patient relative to the patient support structure 108, the CC device 104, and/or the AP 26 such that the mounted CC device 104 applies resuscitative compressions at the desired compression location 124 on the patient 102.

The alignment feature 120 may enable proper alignment of the patient such that the mounted CC device 104 applies resuscitative compressions at the desired compression location 124 on the patient 102 for various tilt angles 109a, 109b, and/or 109c of the plurality of support sections. In an implementation, the alignment feature 120 provides one or more reference points, for example reference points 21, 22, and 23, that correspond, respectively, to various tilt angles. Because the position of the CC device 104 with respect to the desired compression location 124 may vary with tilt angle, multiple reference points 21, 22, 23 may correspond to different degrees of tilt. For example, a first reference point 21 may correspond to a first tilt angle (e.g., the tilt angle 109a at 0-10 degrees) of the support section 108a, a second reference point 22 may correspond to a second tilt angle (e.g., the tilt angle 109a at 10-20 degrees) of the support section 108a, and a third reference point 23 may correspond to a third tilt angle (e.g., the tilt angle 109a at 20-30 degrees) of the support section 108a. Accordingly, as an example, if the support section 108a is already angled at approximately 15 degrees before the patient 102 arrives, the care provider 106 may align the patient 102 with the reference point 22 corresponding to 15 degrees to ensure that the CC device 104, mounted on the patient support structure 108, applies compressions at the desired compression location 124 on the patient 102. Alternatively, if the support portion 108a is angled at approximately 30 degrees before the patient 102 arrives, the care provider 106 may align the patient with the reference point 23 corresponding to 30 degrees to ensure that the CC device 104, mounted on the patient support structure 108, applies compressions at the desired compression location 124 on the patient 102.

The chest compression device 104 may be a standalone device that is placed on the patient's chest (e.g., as illustrated in FIG. 1) and maintained in a position relative to the patient to apply chest compressions at a desired location (e.g., the position 124 in FIG. 5) independent of the tilt of the support sections 108a, 108b, and/or 108c. In an implementation, the care provider 106 manually maintains the CC device 104 at the position relative to the patient to apply chest compressions at the desired location (e.g., the position 124 in FIG. 5). Alternatively, the CC device 104 is secured to the patient support structure 108 to maintain the CC device 104 at the position relative to the patient to apply chest compressions at the desired location (e.g., the position 124 in FIG. 5).

The CC device 104 may be coupled, via a wired and/or a wireless connection, to another device used by the medical personnel during CPR. For example, the CC device 104 may be coupled to the defibrillator 112 and/or the therapeutic delivery devices 158. The attachment of the CC device 104 to these other devices may enable synchronization of multiple CPR related procedures. The CC device 104 may be an automated chest compressor that does not require effort in pushing or pulling from the care provider 106 in order to administer chest compressions. The automated chest compressor may include a compression device, a base mount, a band, fastener, control cables, power cables, and/or other suitable components. The care provider 106 may fasten the CC device 104 to the patient's torso using the band. Further, the care provider 106 may place the base mount, which may be a backboard or may include a backboard, underneath the patient's back and wrap the band across the side of the chest and around the patient's chest. The care provider may secure the band in place via a fastener. Control and power cables may be coupled to a driver via cable connects.

The CC device 104 employed in conjunction with the present disclosure may include a belt-based device such as, for example, the AutoPulse® Resuscitation System provided by ZOLL® Medical Corporation, or a suitable variant thereof. The AutoPulse® Resuscitation System may include an AutoPulse® Platform and a LifeBand®. Other examples of the CC device 104 include piston-based devices and/or other appropriate resuscitative devices.

Figure 6:
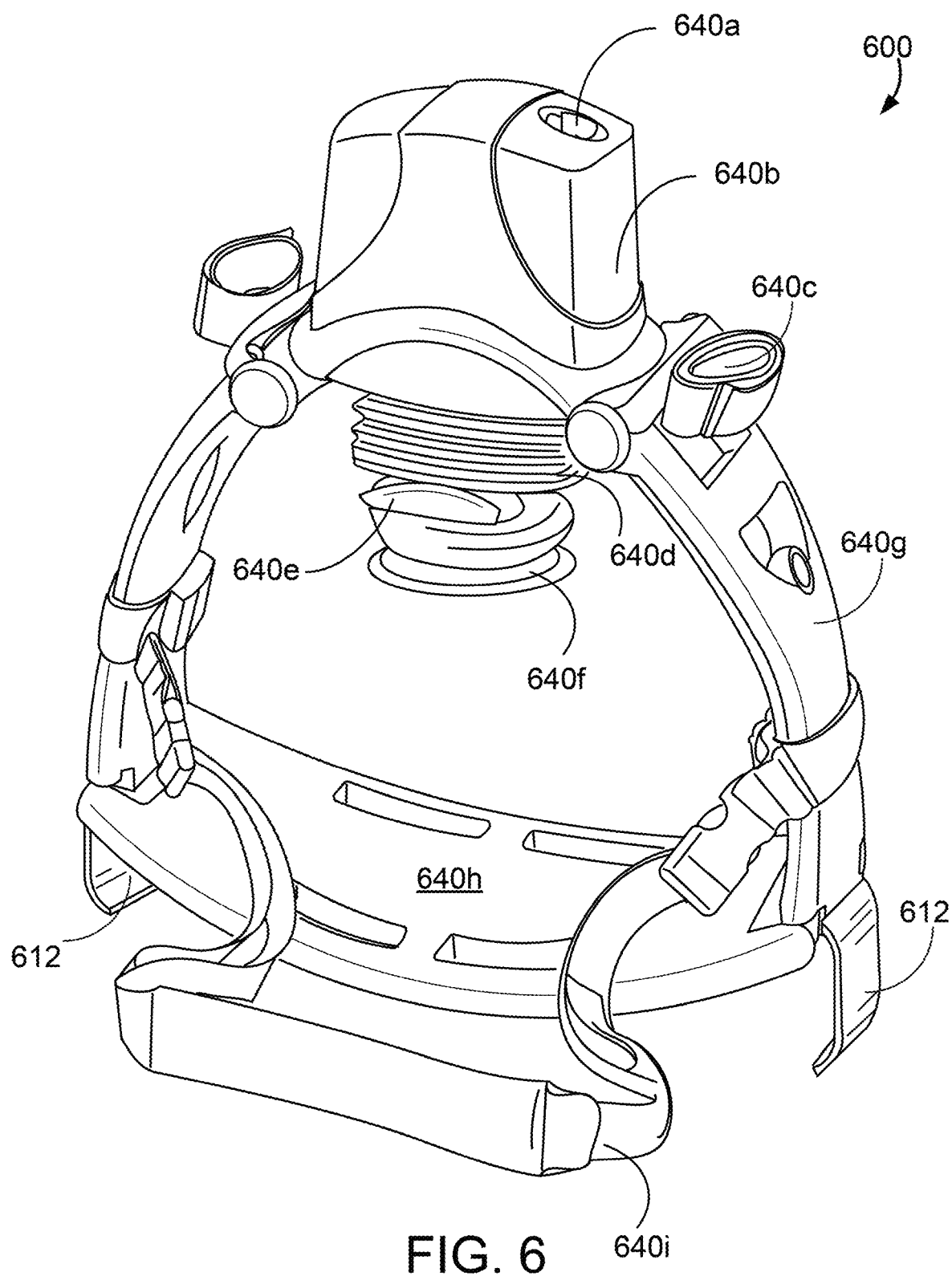
FIG. 6 is a schematic diagram of an example of a piston-based chest compression device.

Referring to FIG. 6, a schematic diagram of an example of the piston-based chest compression (CC) device 600 is shown. In this example, the piston-based CC device 600 includes an operation knob 640*a*, a hood 640*b*, a patient strap 640*c*, bellows 640*d*, height adjustment handle 640*e*, suction cup with compression pad 640*f*, a support leg 640*g*, a backboard 640*h*, and a stabilization strap 640*i*.

Figure 7:
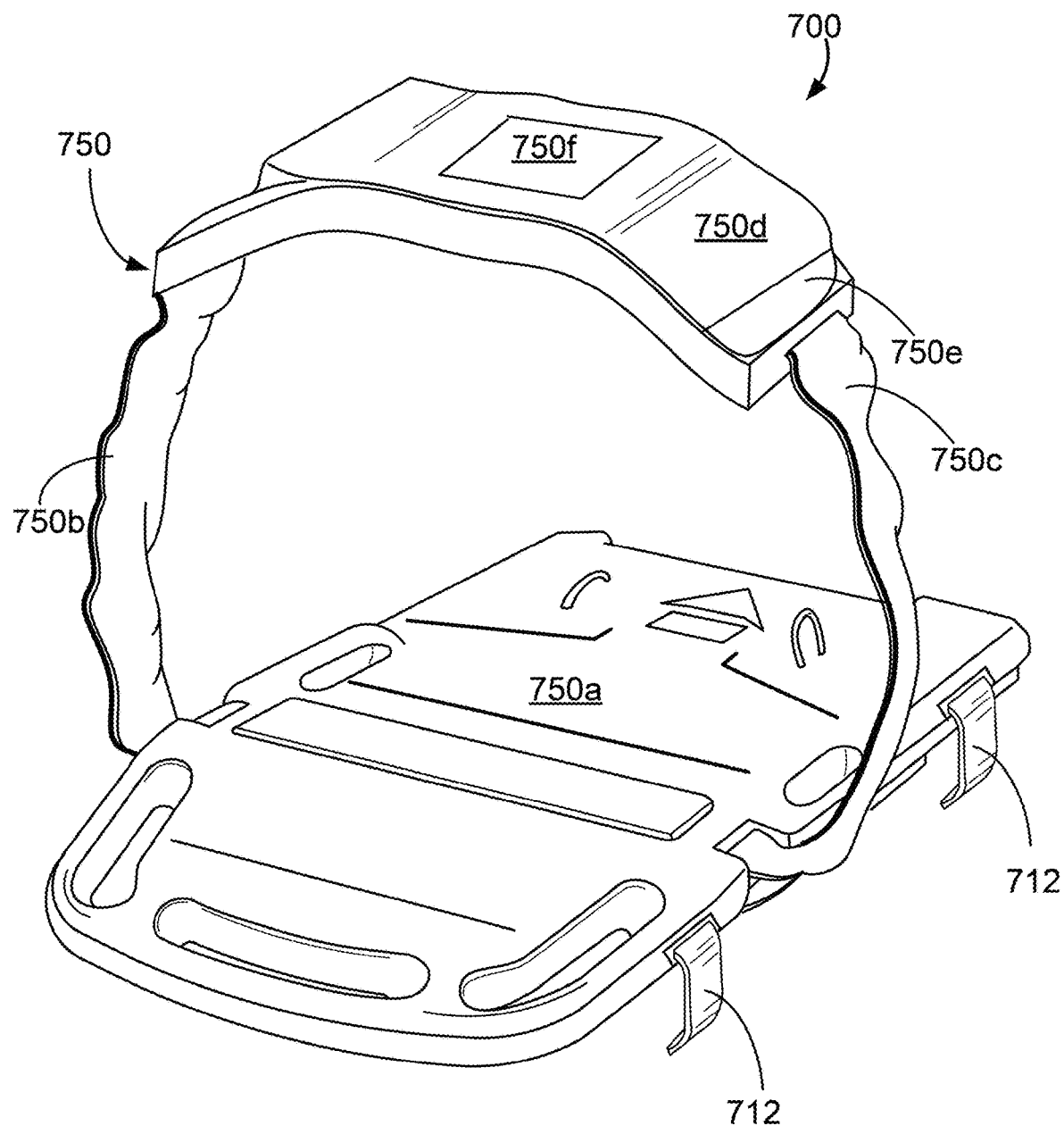
FIG. 7 is a schematic diagram of an example of a belt-based chest compression device.

Referring to FIG. 7, a schematic diagram of an example of the belt-based chest compression (CC) device 700 is shown. In this example, the belt-based CC device 700 includes a load-distributing band (LDB) 750. The LDB 750 may include a backboard 750*a* and two band sections 750*b* and 750*c*, integrated with a compression pad 750*d* and a fastener 750*e*. The CC device 104 may include a display 750*f* configured to provide a graphical user interface (GUI). The GUI may include information about a plurality of parameters related to CPR treatment and/or measured tilt angles. The band may be a single-use component that is attached to the compression platform before each use of the CC device 700.

As provided herein, the CC device 104 may be an automated chest compressor that does not require effort in pushing or pulling from the care provider. The automated chest compressor may include a compression device, a base mount, a band, fastener, control cables, power cables, and/or other suitable components. Compression device may be fastened to the patient's torso using the band. The backboard 25 (e.g., backboard 750*a* or 640*h*) may be placed underneath the recipient's back and the band is wrapped across the side of the chest and around the recipient's chest. The band may be fastened via a fastener. Control and power cables may be coupled to a driver via cable connects. The care provider 106 may assist patient's ventilation using a ventilation bag 114 and/or performing abdominal compressions, for example, synchronized with chest compressions. Abdominal compressions and/or ventilations may also be applied as an intervention in conjunction with elevation of the patient's upper body. That is, it may be beneficial to the patient to apply abdominal compressions, or to bind the abdomen of the patient, during certain phases of elevation. For example, when the patient's head is elevated to a substantial degree (e.g., approximately 30 degrees), there may be a tendency for portions of the torso to become distended, or blood may collect in an undesirable manner below the heart. Accordingly, it may be preferable to provide a suitable amount of pressure on the abdomen so that blood is less likely to accumulate away from other parts of the body (e.g., vital organs, heart, and brain). In some implementations, the configuration and geometry of the patient support structure 108 enables the care provider to use the same body position and compression technique as in standard CPR.

Figure 8:
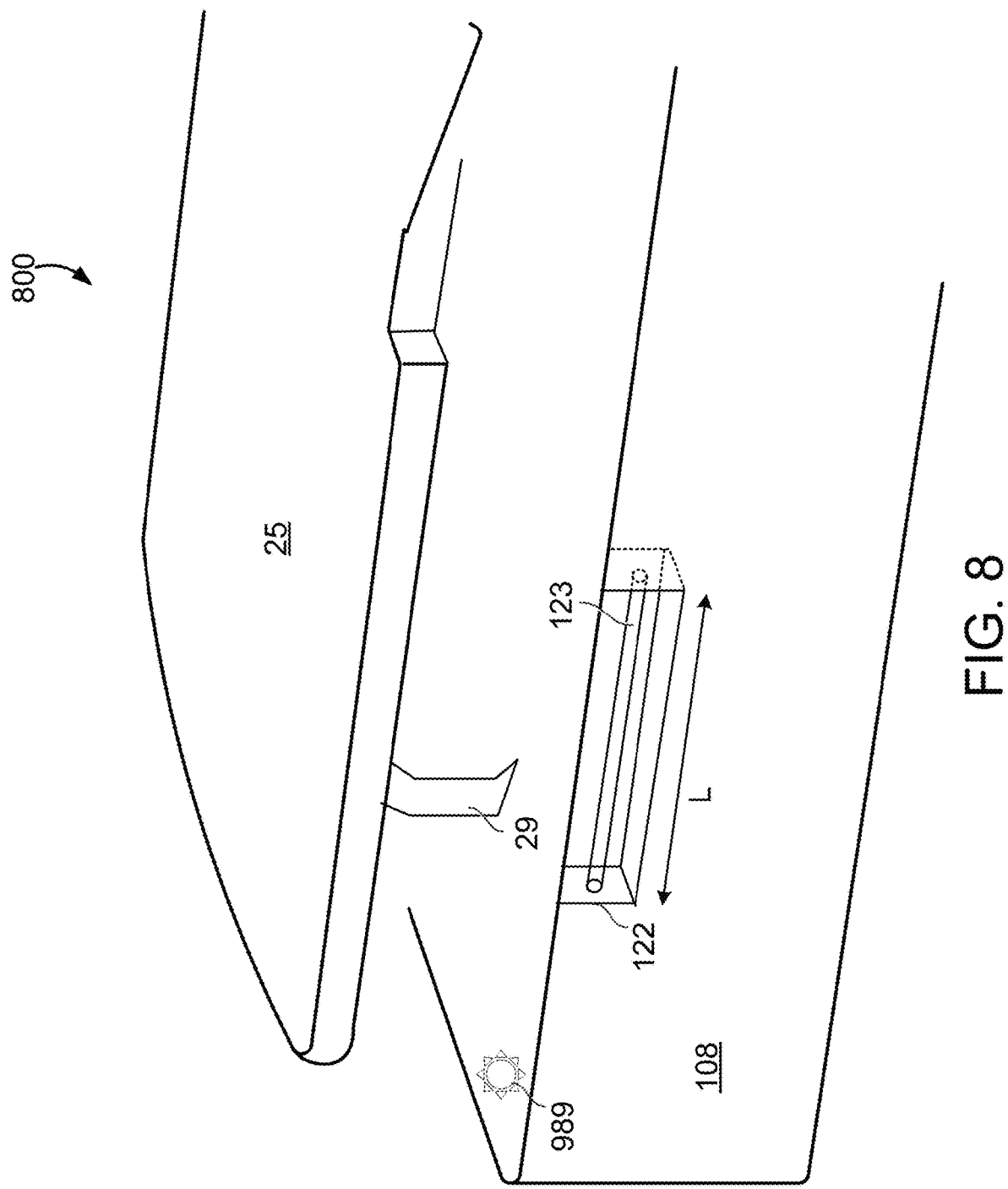
FIG. 8 is a schematic diagram of an example of a coupling for a CC device and patient support structure.

Referring again to FIG. 5 with further reference to FIGS. 6, 7, and 8, the patient support structure 108 is configured to couple to a backboard 25 of the CC device 104 (e.g., the backboard 640*h* or the backboard 750*a*). The backboard 25 of the CC device 104 may couple to the patient support structure 108 via a mechanical coupling that provides adjustment of the position of the CC device 104. The mechanical coupling includes a CC device mount disposed on the patient support structure 108 and one or more complementary mounting structures disposed on the CC device 104. Examples of a device mounts are discussed below with regard to FIGS. 8 and 9. The CC device mount may allow adjustment of the CC device 104 relative to the patient support structure 108 along one or more of the longitudinal axis 126*a*, the transverse axis 126*b* and/or the vertical axis 126*c*. The adjustment may enable the CC device 104 to deliver compressions at the desired compression location 124 for any values of the tilt angles 109*a*, 109*b*, 109*c*, and 109*d*. As such, the CC device 104 may maintain a position relative to the patient 102 even as the tilt angles 109*a*, 109*b*, 109*c*, and/or 109*d* are adjusted based on one or more of a physiological parameter, measured signal(s), physiological phase and/or phase of resuscitative treatment.

Referring to FIG. 8, a schematic diagram of an example of a coupling 800 for a CC device is shown. The backboard 25 may include the one or more fasteners 29 (e.g., complementary mounting structures) that latch onto one or more CC device mounts 122 of the patient support structure 108. The one or more fasteners 29 may include one or more types of fasteners including brackets, thumb screws, snap-on clamps, spring loaded clamps, magnetic clamps, straps, hook-and-eye fasteners, etc. As another example, the one or more fasteners 29 may comprise a gantry. For example, each CC device mount 122 may include a bar 123 and the one or more fasteners 29 may removably and adjustably couple to the bar 123. The bar 123 is shown in FIG. 8 with a circular cross-section as an example only and other geometries are with the scope of the disclosure. The one or more fasteners 29 may couple anywhere along the length of the bar 123 or the bar 123 may include discrete attachment points. In an implementation, the CC device mount 122 may include multiple discrete bars, rather than a continuous bar, that each serve as attachment points for the one or more fasteners 29. Although one fastener 29 and one CC device mount 122 are shown in FIG. 8 for simplicity, the system 800 may include multiple fasteners 29 and CC device mounts 122 at various locations along the backboard 25 and the patient support structure 108. For example, the fasteners 29 may include the brackets 612 in FIG. 6 or the brackets 712 in FIG. 7. The fasteners 29 may latch along a length of the CC device mount 122 so that the affixation point (AP) 26 is adjustable along the length, L, of the CC device mount. In this manner, the location of the CC device 104 is adjustable relative to the patient support structure 108. As another example, the CC device mount 122 may include a male coupling component configured to removably attach to a female coupling component on the CC device 104. Additionally or alternatively, the CC device mount 122 may include a female coupling component configured to removably attach to a male coupling component on the CC device 104.

Figure 9A:
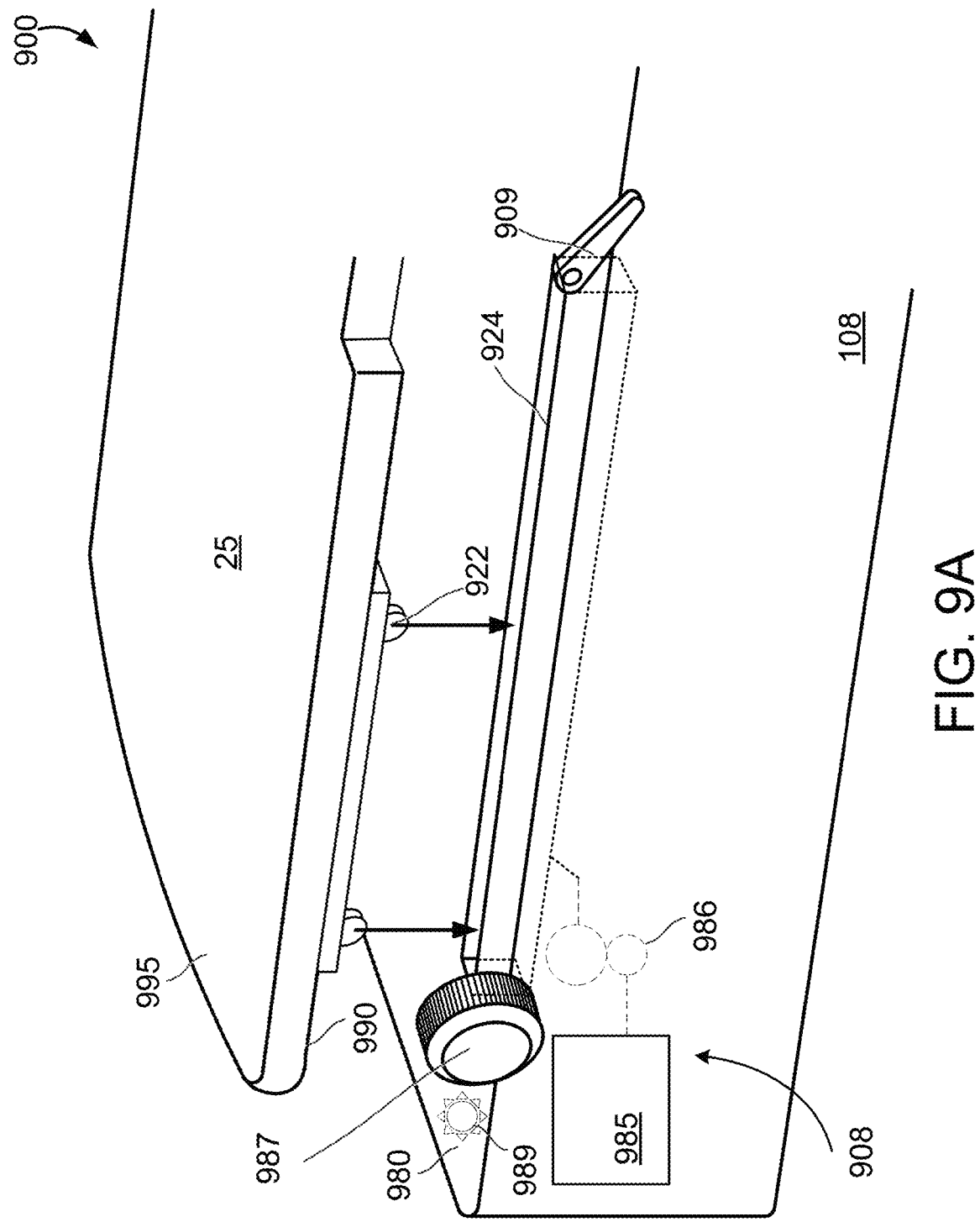
FIGS. 9A and 9B are schematic diagrams of another type of coupling for a CC device and patient support structure.
Figure 9B:
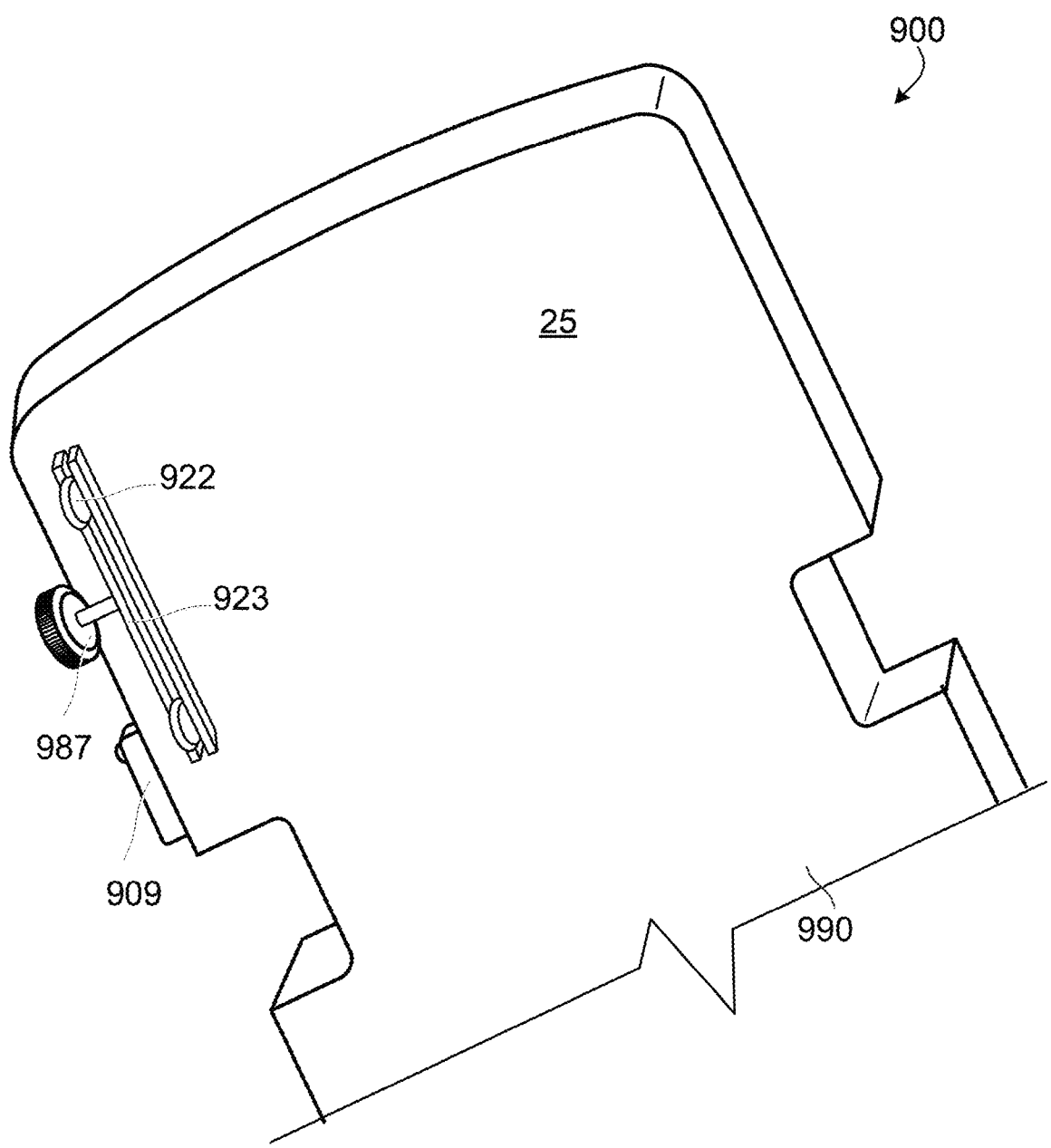

Referring to FIGS. 9A and 9B, an example of another type of coupling 900 for a CC device and patient support structure is shown. In this example, the CC device mount 924 includes a rail that extends along a longitudinal direction of the top side 980 of the patient support structure 108. The complementary mounting structure includes wheels 922 disposed on a bottom side 990 of the backboard 25. The top side 995 of the backboard 25 is proximate to the patient during use. The wheels 922 may be oriented in pairs via a wheel bracket 923. The wheel bracket 923 may be disposed along a longitudinal direction on the bottom side 990 of the backboard 25. The geometries (e.g., cross-sectional geometries and/or surface geometries) and sizes of the rail and the wheels 922 may enable the rail to mechanically engage the wheels 922 with and roll along the rail. In various embodiments, the rail may be a recess into the top surface 980 of the patient support structure 108. This recess may be composed of and/or lined with a hard foam, metal or plastic material, so that it possesses sufficient stability to retain the wheels 922. In this manner, the rail may obviate the need to couple the backboard 25 to the patient support structure 108 with adhesive tapes, hook-and-loop straps, or the like. However, in various implementations, adhesive tapes, hook-and-loop straps, male-female connectors, and/or other couplings may replace or supplement the rail/wheel structure. For example, another coupling may supplement the rail/wheel structure to provide additional patient security and safety.

The bracket coupling 800 and the roller coupling 900 are examples only and not limiting of the disclosure. Other mechanical couplings are possible. The mechanical coupling adjustably and removably couples the CC device 104 to the patient support structure 108. Further, the mechanical coupling enables the backboard 25 to remain parallel to at least a section of the patient support structure 108. In general, the chest of the patient 102 will be proximate to an end section (e.g., section 108*a* in FIG. 2A) of the patient support structure 108. Therefore, in general, the backboard 25 remains parallel to this end section proximate to the chest of the patient. In this manner, the CC device 104 is positioned for compression of the chest at a suitable location on the patient, regardless of the current tilt angle of the section of the patient support structure to which the CC device 104 is coupled.

It can be appreciated that the CC device mount 122 may be able to mechanically couple with the CC device 104, without requiring that the CC device 104 have a complementary mounting structure. For example, the CC device mount 122 may include clamps, grips, straps or other fixation structure(s) configured to secure the CC device 104 to the patient support structure 108 without coupling to a complementary mounting structure on the CC device 104. These fixations structures may secure one or more portions of the CC device (e.g., the backboard, the compression belts, the piston mechanism, etc.). The CC device mount 122 may secure that CC device 104 to the patient support structure 108 in a manner such that the CC device 104 can provide chest compressions to a patient disposed on the patient support structure 108 with one or more of the patient support sections in tilted or non-tilted positions.

The positions of components of the bracket coupling 800 and the roller coupling 900 are examples only and alternative or additional positions are within the scope of the disclosure. For example, CC device mounts in the body of the patient support structure, rather than the edge as shown, may enable transverse adjustment of the position of the CC device 104. Similarly, multiple rails and wheels may enable transverse adjustment of the position of the CC device 104. The CC device mounts and/or the rails may provide attachment points at various heights to enable vertical adjustment of the position of the CC device 104. Further, the components described may be used in combination to provide additional flexibility in the positioning of the CC device 104.

In an implementation, the patient support structure 108 may include a position adjuster 908 configured to enable motion of the backboard 25 parallel to the surface of the patient support structure 108. In an implementation, the backboard 25 may include the position adjuster 908. Such motion adjusts the position of the CC device 104 relative to the patient 102. The position adjuster 908 is configured to allow adjustment of the position of the CC device 104 relative to the patient support structure 108 and/or relative to the patient 102. The position adjuster 908 may be a manual position adjuster or an automated position adjuster. For example, the position adjuster 908 may include a knob 987 or lever (not shown). The care provider may manually adjust the position of the CC device 104 by manipulating the knob or the lever, or by otherwise manually sliding the backboard 25 along the patient support structure 108. However, these are examples only and not limiting of the disclosure. As another example, the position adjuster 908 may include a motor 985 and may receive a control signal (e.g., via a wired and/or wireless connection) from the defibrillator 112, the CC device 104, the tilt controller 180, and/or the local computing devices 160. In response to the control signal, the motor 985 may activate appropriate mechanical and/or electronic linkages 986 within the position adjuster 908 to automatically adjust the position of the CC device 104. In an implementation, the position adjuster 908 may be mechanically and/or electronically linked to the defibrillator 112, the tilt controller 180 and/or the one or more automated tilt adjusters 185. In this manner, the position adjuster 908 may be controlled to adjust the position of the CC device 104 based on (e.g., during, in response to, or otherwise in conjunction with) tilt angle adjustment and/or other patient care activities.

Automatic adjustment of the position of the CC device 104 may include a shift in the position of the CC device 104 to a predetermined position corresponding to the particular tilt angle 109*a*, 109*b*, 109*c*, and/or 109*d*. Additionally or alternatively, the CC device 104 and/or the patient support structure may include sensors configured to detect a position of an anatomical feature of the patient. The shift in the position of the CC device 104 may occur in response to a detected change in the position of the anatomical feature of the patient. For example, the patient support structure 108 may include an optical alignment aid configured and arranged for projecting, at least temporarily, a light signal on the patient's torso and detecting a reflected signal that may provide alignment information for the CC device 104.

The automatic adjustment of the position of the CC device 104 may be based on the adjustable tilting and/or on anatomical landmarks of the patient's torso. For example, the automated position adjuster may shift the position of the CC device 104 to a preset position for each tilt angle 109*b*. The automatic adjustment of the position of the CC device 104 based on anatomical landmarks may include configuring the automated position adjuster to shift to a new position in response to a signal associated to an anatomical landmark detected by a sensor. For example, the CC device mount 122 and/or 924 may include an optical alignment aid 989 configured and arranged for projecting, at least temporarily, a light signal on the patient's torso and detecting a reflected signal that may provide information useful in aligning the CC device 104 with the desired compression location 124. In an implementation, the backboard 25 or other component of the CC device 104 or patient support structure 108 may include the optical alignment aid 989.

The patient support structure 108 and/or the backboard 25 may further include a lock 909. The lock 909 may be, for example, an adjustable lever. The lock 909 may restrict and/or prohibit motion of the CC device 104 along the surface of the patient support structure 108. For example, the lock 909 may prevent the CC device 104 from moving in response to an inadvertent bump. In an implementation, the lock 909 may restrict and/or prohibit decoupling of CC device 104 from the patient support structure 108. When it is desirable for the CC device 104 to be moved to a different location along the patient support structure 108 to properly align with the patient, the lock 909 may subsequently be unlocked so that the CC device may be moved in a suitable manner.

Figure 10A:
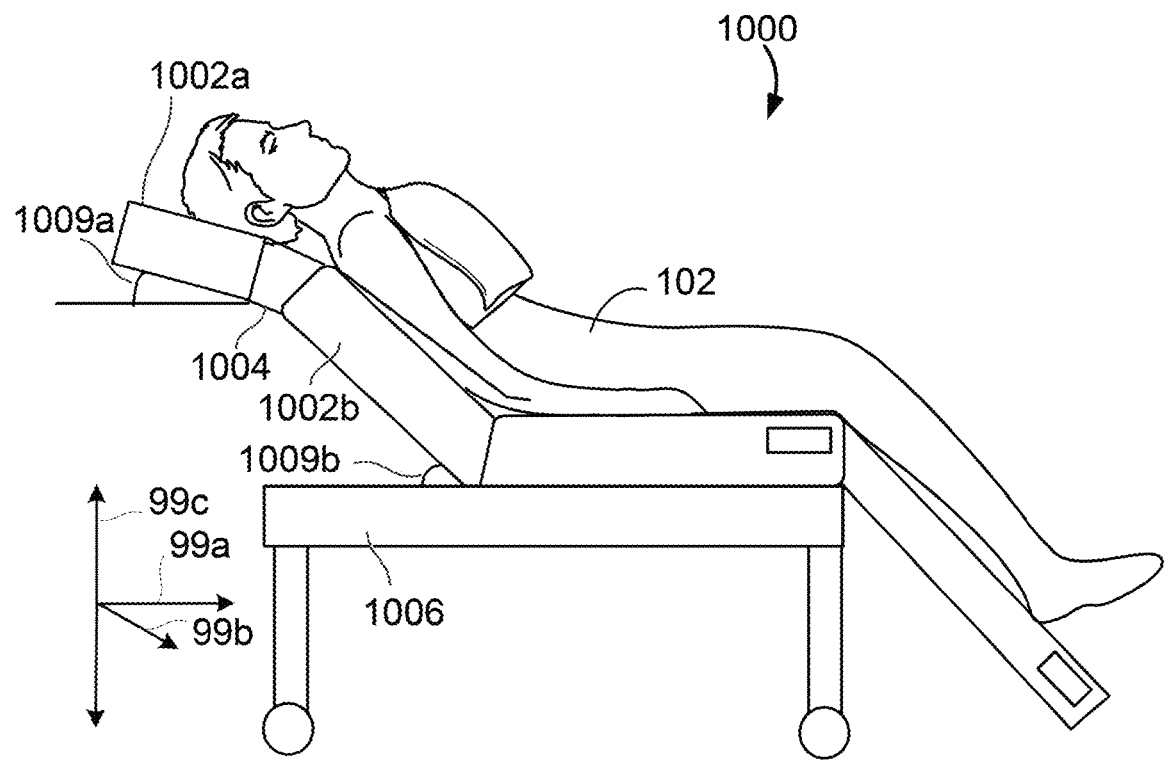
Figure 10B:
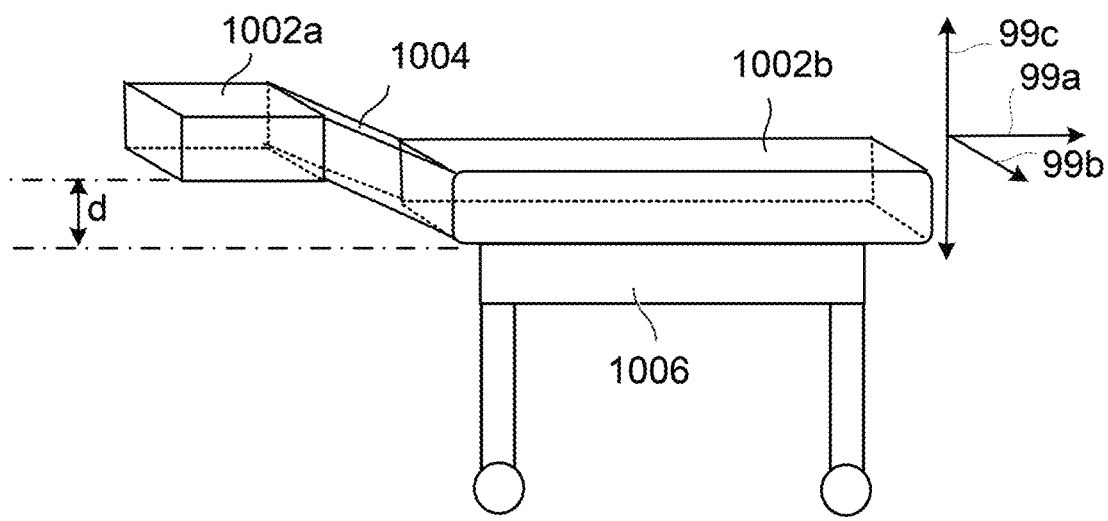

Referring to FIGS. 10A and 10B, another example of a patient support structure is shown. The patient support structure 1000 is configured to support a patient 102. The patient 102 is shown in FIG. 10A for clarity and is separate from the patient support structure 1000. The patient support structure 1000 may include some or all of the components and functionality of the patient support structure 108 as described above. In addition, the patient support structure 1000 includes two or more patient support sections. The two or more patient support sections include at least a patient support section 1002a (e.g., a first patient support section) configured to support the patient's head and a patient support section 1002b (e.g., a second patient support section) configured to support the patient's torso, and a spacer 1004.

The spacer 1004 is disposed between and pivotally coupled to the patient support section 1002a and the patient support section 1002b. The space is configured to elevate the patient support section 1002a relative to the patient support section 1002b. Further, the spacer 1004 allows the patient support section 1002a to tilt at an angle 1009a that is different than the angle 1009b. The angle 1009b is a tilt angle of the patient support section 1002b relative to a horizontal axis 99a or 99b. The patient support section 1102b may support at least a portion of the patient's back. As shown schematically in FIG. 10B, the spacer 1004 is configured to adjust the distance between the patient support section 1002a and the patient support section 1002b along the direction 99c (i.e., perpendicular to a reference plane defined by patient support section 1002b that includes the axes 99a and 99b). An adjustable distance, d, between the patient support section 1002a and the patient support section 1002b may provide for a substantially clear airway while the patient's upper body is tilted. For example, when the patient support section 1002a and the patient support section 1002b are both tilted an appreciable amount, the head of the patient may be elevated, however, such a configuration may lead to obstruction of the patient's airway. By allowing adjustment of the patient support section 1002a independently from the patient support section 1002b, the patient support structure 1000 may enable elevation of the patient's head and placement of the patient's head in a position that allows the airway to remain relatively unobstructed. The distance, d, between the patient support section 1002a and the base 1006 may be, for example, between approximately 0 to 50 cm, between approximately 2 to 50 cm, or between approximately 2 to 20 cm. The spacer 1004 may enable the airway of the patient 102 to remain substantially unobstructed by tilting the head of the patient relative to the chest when the patient is supported by the patient support structure 1000. This configuration may also provide the physiological benefits of elevating the head and the heart, while also maintaining a clear patient airway.

The patient support section 1002a is configured to tilt to an adjustable tilt angle 1009a relative to a horizontal axis 99a or 99b. The angle 1009a may be the recommended angle based on one or more of a physiological parameter for the patient, a physiological signal from the patient, a physiological phase of the patient, and a phase of the CPR treatment, as discussed above with regard to FIG. 1. For example, the angle 1009a may be between approximately 0 and 40 degrees, between approximately 0 and 30 degrees, between approximately 10 and 30 degrees, between approximately 10 and 20 degrees, between approximately 20 and 30 degrees, between approximately 25 and 30 degrees, or between approximately 20 and 25 degrees.

Figure 11A:
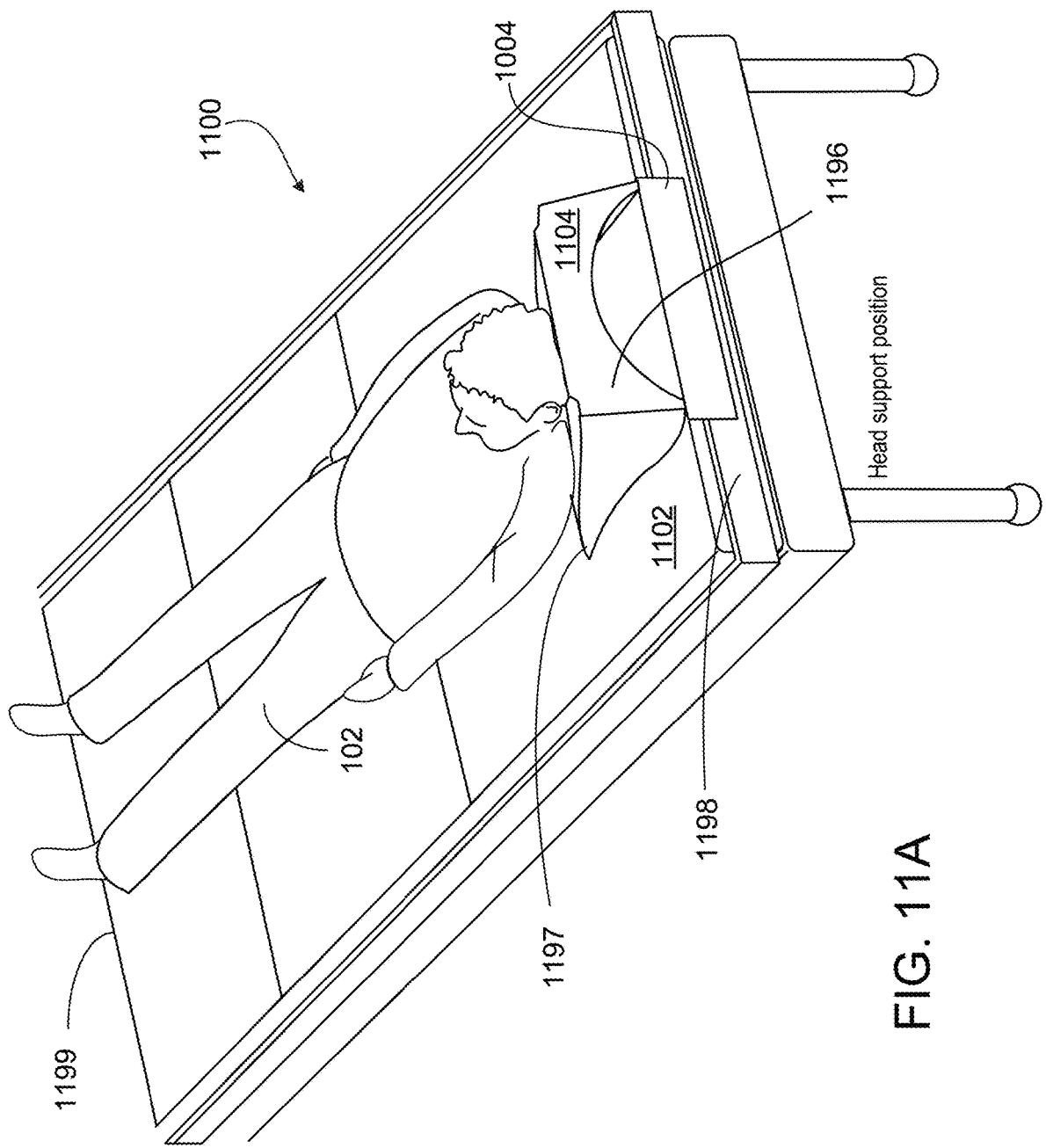
FIGS. 11A-11E are schematic diagrams of an example of a patient support structure.

Referring to FIGS. 11A-11E, another example of patient support structure is shown. The patient support structure 1100 is configured to support a patient 102. The patient 102 is shown in FIG. 11A for clarity but is not a component of the patient support structure 1100. The patient support structure 1100 may include some or all of the components and functionality of the patient support structure 108 as described above. In addition, the patient support structure 1100 includes an adjustable head support 1104.

Figure 11B:
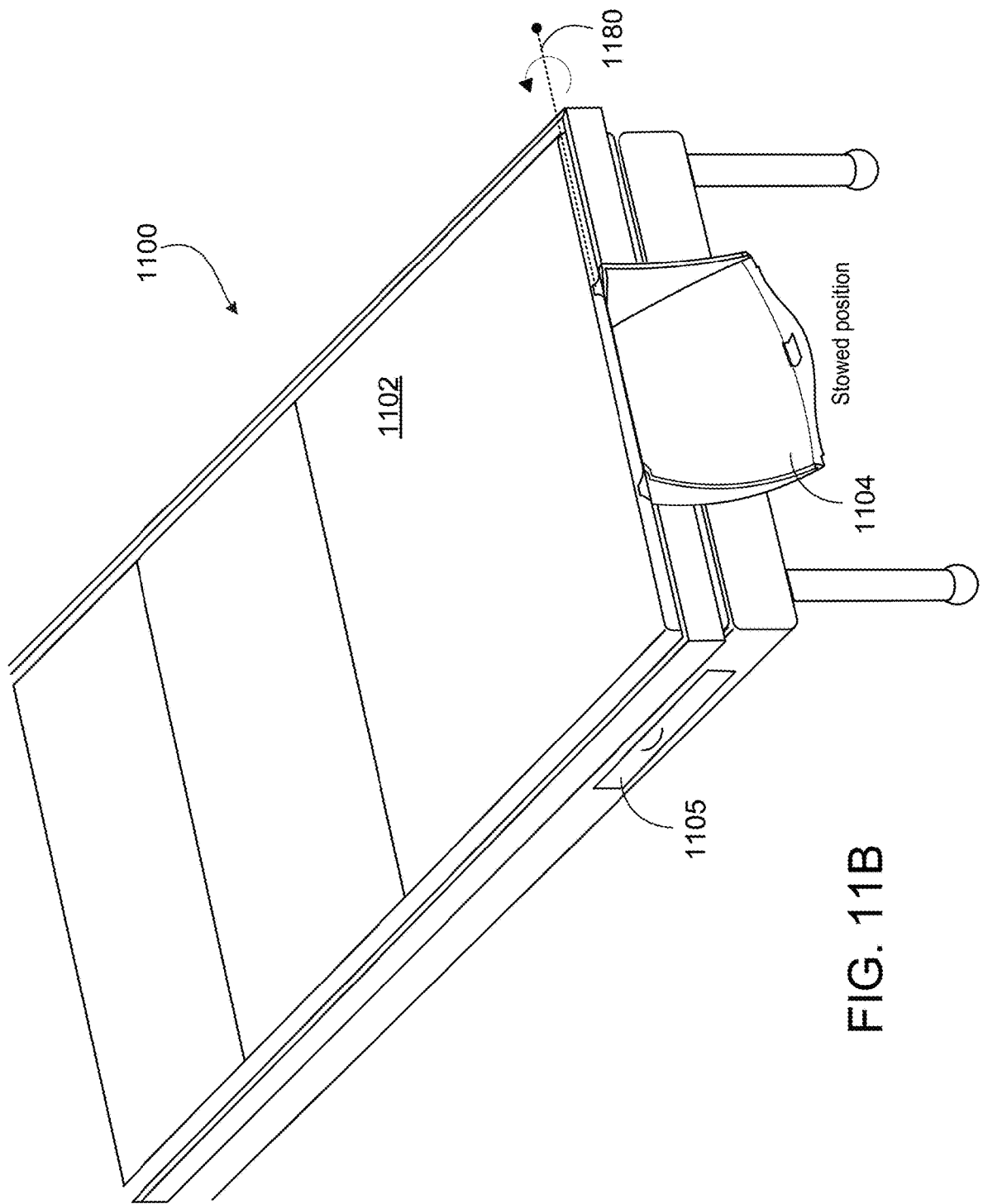
Figure 11C:
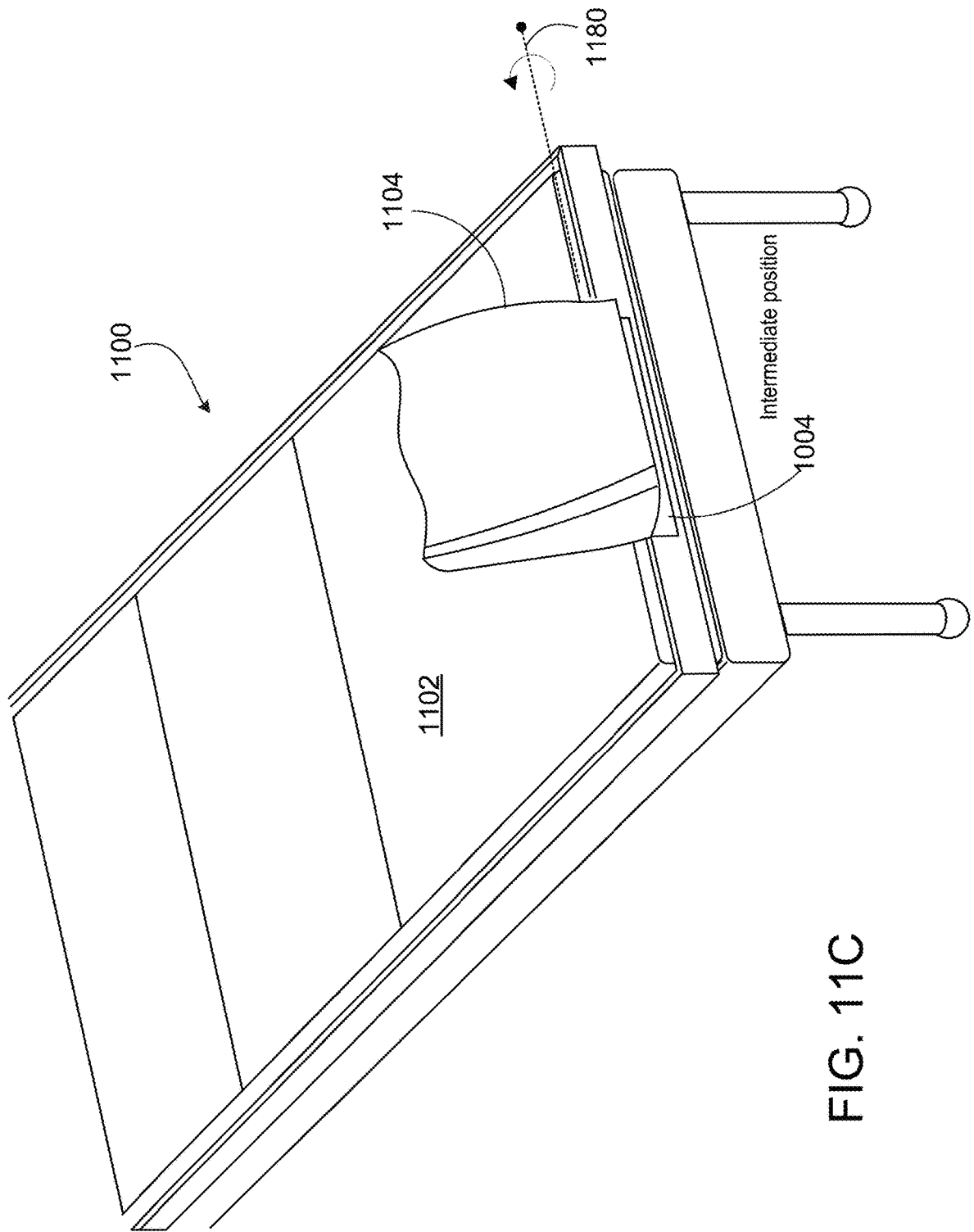
Figure 11D:
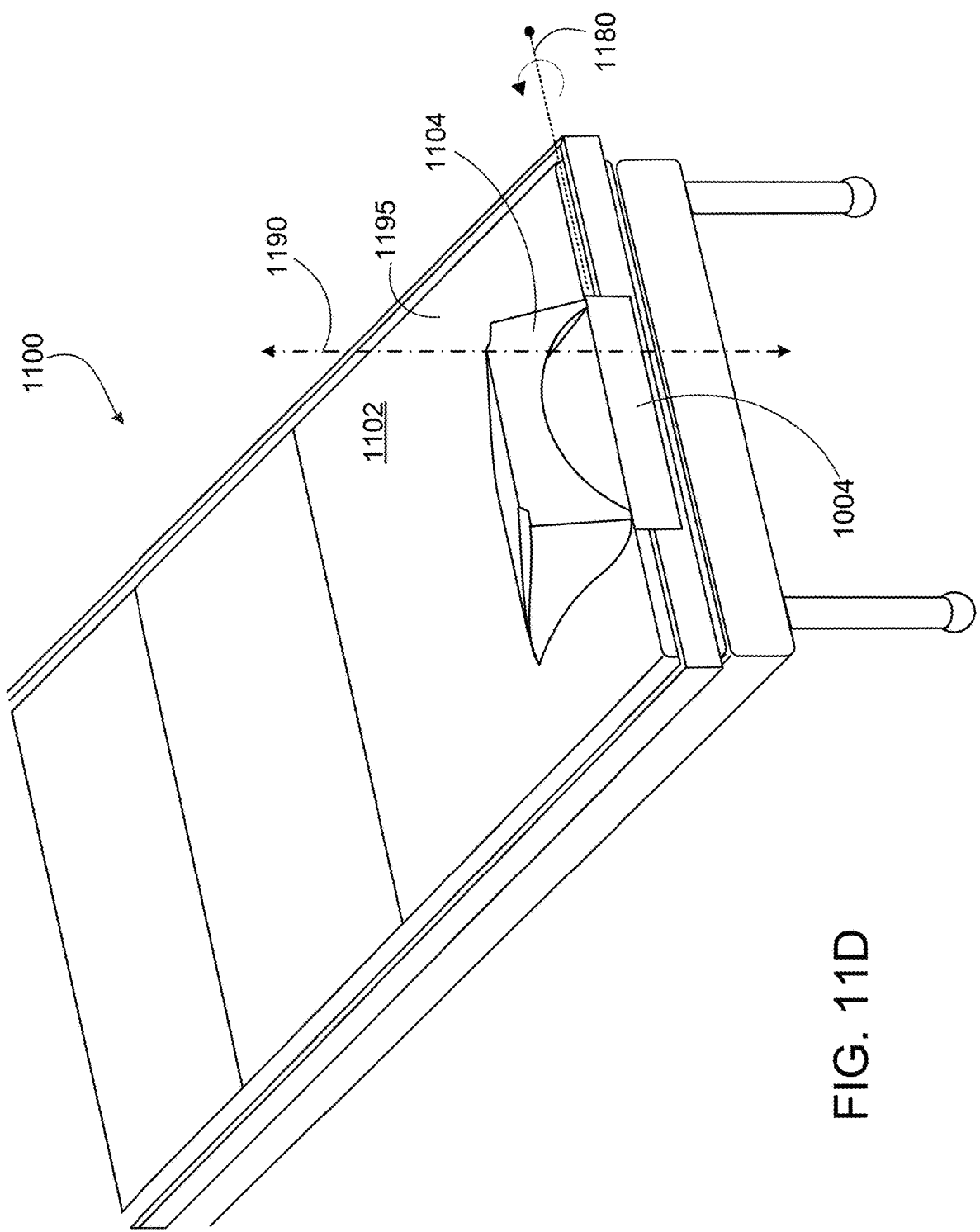

The head support 1104 is mechanically coupled to the patient support section 1102 at an end of the patient support section 1102. The mechanical coupling may include a hinge and may further include a tether. The mechanical coupling between head support 1104 is configured to enable movement of the head support 1104 from the stowed position to a head support position. Further, the mechanical coupling is configured to maintain the head support 1104 in various positions and to enable adjustment of the head support 1104 between the various positions. These positions may include, for example, a stowed position (e.g., as illustrated in FIG. 11B), an intermediate position (e.g., as illustrated in FIG. 11C) and a support position (e.g., as illustrated in FIG. 11D). The head support position is a position on a top side of the patient support structure and at an end along a longitudinal direction of the patient support structure. As described below, in an implementation, the head support 1104 may have a wedge shape. In the support position, a thin edge 1197 of the wedge faces a distal end 1199 of the patient support structure 1100 along the longitudinal direction. The thick end 1196 of the wedge faces a proximal end 1198 of the patient support structure 1100 along the longitudinal direction. The head support position is configured to support the head of the patient. The head support 1104 may rotate around an axis 1180, as shown schematically in FIG. 11B, to change position, or move between the stowed position and the support position by another appropriate method. In the support position the head support 1104 is configured to be placed underneath a head or other part of the upper body of a patient to elevate the head or the other part of the upper body relative to the patient support section 1102. In an implementation, the head support 1104 may be removable (e.g., the head support 1104 may be configured to decouple from the patient support section 1102) and the patient support structure 1100 may include a head support storage compartment 1105 for storing the head support 1104.

In an implementation, the head support 1104 may include the spacer 1004 (e.g., as described with reference to FIGS. 10A and 10B). The spacer 1108 may be configured to raise and lower the head support 1104 relative to the patient support section 1102 (e.g., along a direction 1190 perpendicular to a patient support surface 1195 of the patient support section 1102, as shown schematically in FIG. 11D).

The head support 1104 may be made of an inelastic material (e.g., polyurethane, PVC or polypropylene) to maintain the head at a particular angle, as imposed by the geometrical characteristics of the head support 1104. The head support 1104 may be formed by bonding along seams of appropriate patterns to form the shaped wedge. The seams of the head support 1104 may be formed by adhesive, chemical bonding, heat welding, RF welding or ultrasonic welding. During use with a patient, the head support 1104 may include a head support cover. The head support cover may be a cloth material or bed sheet and may provide a more comfortable surface for the patient's head than the head support 1104 without the cover. An example of such a cloth material is a blend of 65% cotton and 35% polyester. Alternatively, the head support cover may be a durable paper or other inexpensive material to provide the option of a disposable head support cover.

Figure 11E:
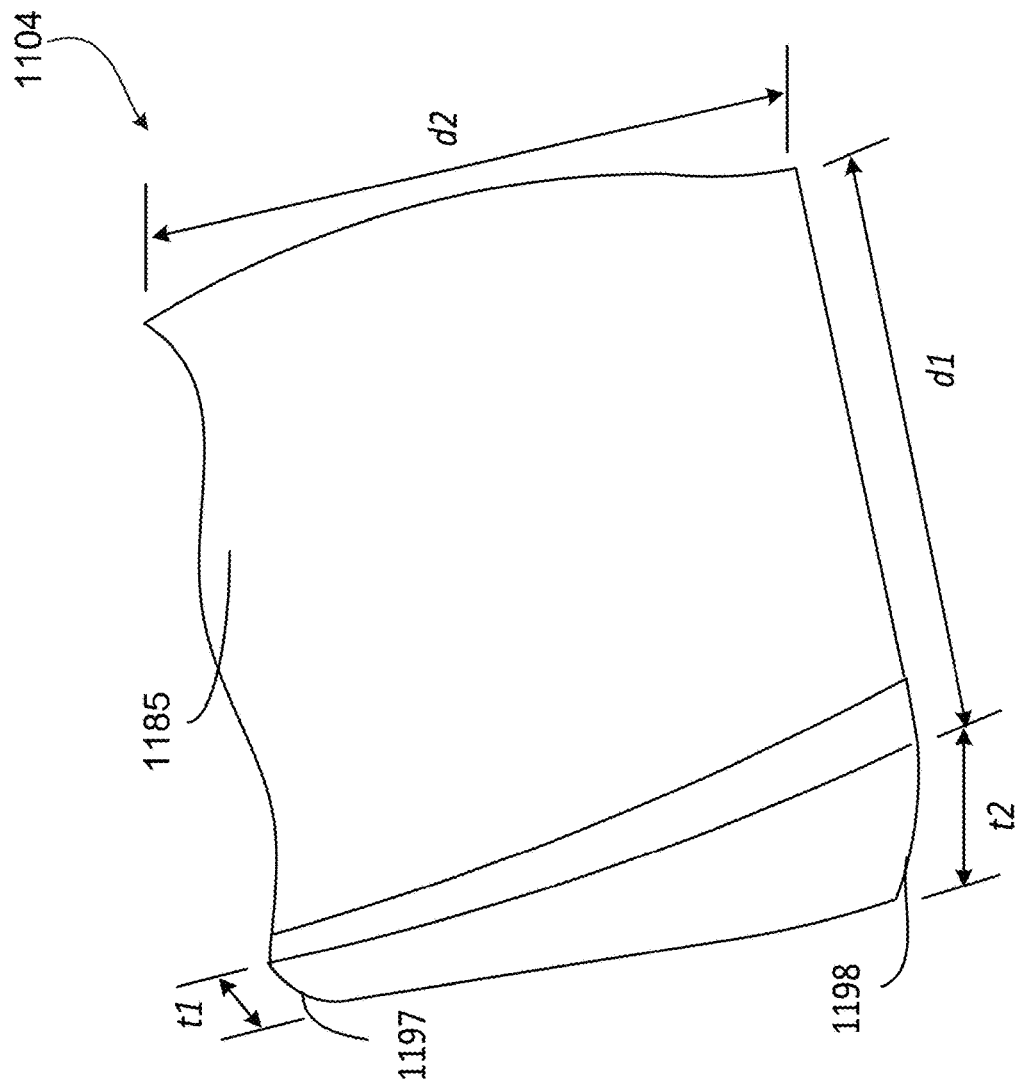

Referring to FIG. 11E, the geometrical characteristics of the head support 1104 may include a thickness, t1, of approximately 0.01 to 3 cm at the thin edge 1197 and a thickness, t2 of approximately 2 to 10 cm at the thick end 1196. In an implementation the cross-section of the head support 1104 is approximately a wedge shape. The support surface 1185 of the head support 1104 may have an approximately rectangular or square shape with side lengths d1, of about 7 to about 20 cm and d2, of about 6 to about 15 cm. However, this shape is an example only as other shapes (e.g., an arch, a circle, an oval, a semicircle, or combinations thereof) are consistent with the disclosure.

Figure 12:
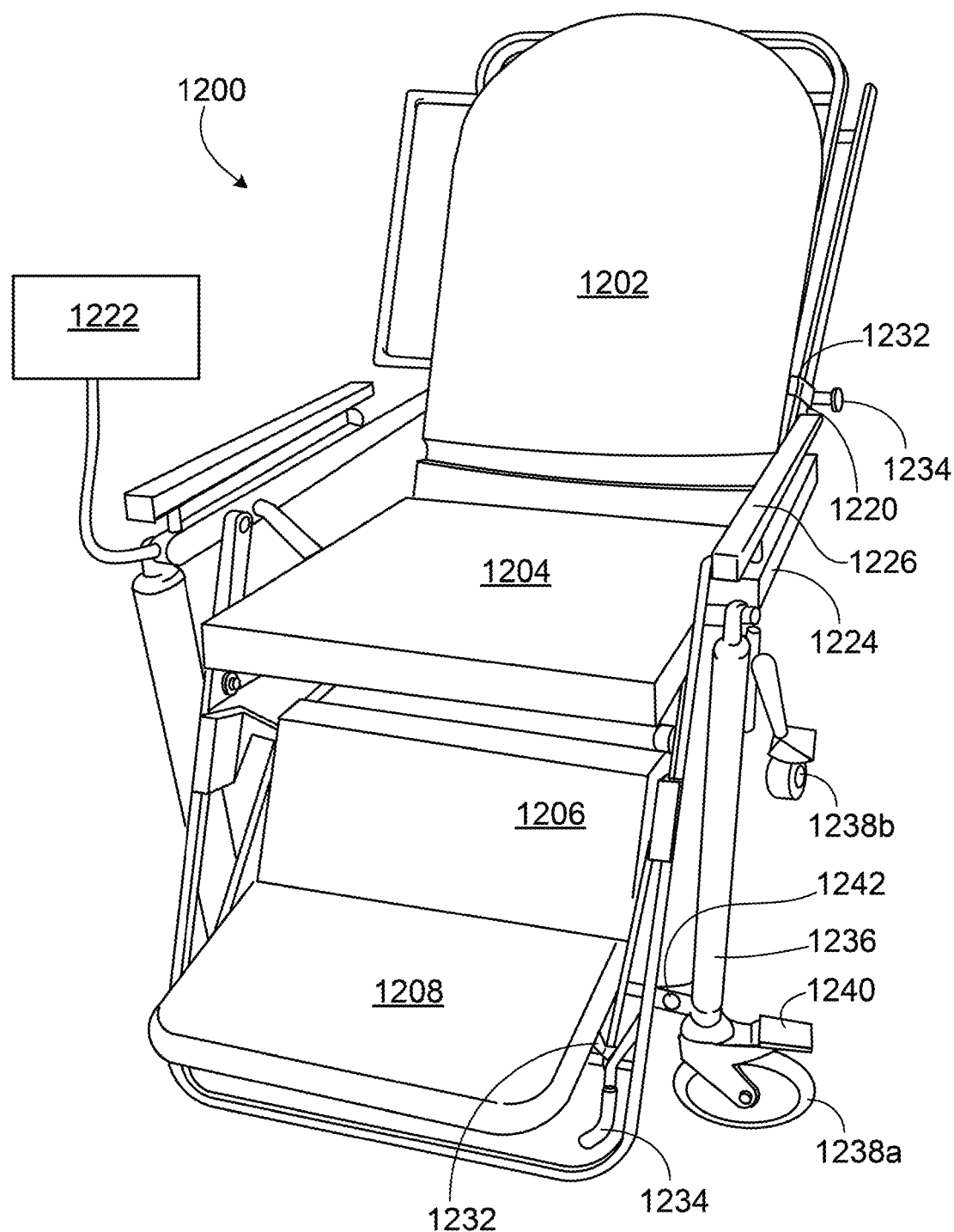
FIG. 12 is a schematic diagram of an example of a patient support structure.

Referring to FIG. 12, another example of a patient support structure is shown. The patient support structure 1200 may include some or all of the components and functionality of the patient support structure 108 as described above. In addition, the patient support structure 1200 includes components that support a configuration of the patient support structure 1200 as a powered ambulatory stretcher chair.

The patient support structure 1200 includes a patient support sections 1202, 1204, 1206, and 1208. Each of the plurality of patient support sections 1202, 1204, 1206, and 1208 is configured to support a particular portion of a patient's body and configured to raise or lower the supported portion of the patient's body to an adjustable tilt angle, substantially as described above with regard to the patient support structure 108. The back section 1202 is hingedly connected to the seat section 1204. In turn, the seat section 1204 is hingedly connected to a first end of the leg support section 1206, with footrest section 1208 hingedly secured to an opposite and second end of the leg support section 1206. In an implementation, the patient support sections 1202, 1204, 1206, and 1208 are in a chair configuration to support an upright patient. In an implementation, the patient support sections 1202, 1204, 1206, and 1208 are in a stretcher configuration to support a supine patient. In various implementations, the patient support sections 1202, 1204, 1206, and/or 1208 may rotate relative to one another such that the patient support structure 1200 may change from a chair configuration to a stretcher configuration or from stretcher configuration to a chair configuration.

In some implementations, the back section 1202, the seat section 1204, and the leg support section 1206 are cushioned with an appropriate cloth covered foam pad or the like, such pads covering a rigid underlayment maintained by an appropriate frame structure. A bar 1220 is hingedly interconnected between the frames of the back section 1202 and the seat section 1204. An operator control system 1222 is mounted upon a free end of the bar 1220. The hinged interconnection of the bar 1220 between the frames of the back section 1202 and the seat section 1204 is configured to maintain the operator control system 1222 at a particular height relative to a patient in the patient support structure 1200. In some implementations, the operator control system 1222 may move over a range of about 30 cm between the upright chair position and the supine stretcher position.

The patient support structure 1200 may include a pair of side rails 1224, one on each side of the patient support structure 1200, and each being provided with an arm rest 1226 thereon. As shown in FIG. 12, the side rails 1224 may be in an up position. Upon manual or automatic activation, the side rails 1224 may pivot downwardly. In some implementations, the patient support structure 1200 may include a second set of side rails that extend from the sides of the back 1202.

The patient support structure may include one or more indicators 1232 and a tilt switch 1234 integrated into or attached to the patient support structure 1200. The one or more indicators 1232 and/or the tilt switch 1234 may be configured to communicate with the operator control system 1222. In some implementations, the patient support structure 1200 may include a safety switches at the extreme longitudinal ends of the patient support structure 1200. The safety switches may disable the powered chair, and particularly operation of the tilting thereof. For example, a safety switch 1242 on a base assembly 1236 of the patient support structure 1200 is configured so that the care provider can depress the safety switch 1242 with his/her foot to disable one or more tilting operations of the patient support structure 1200.

The patient support structure 1200 may include caster wheels 1238, typically freewheeling and pivotal about a substantially vertical axis. The caster wheels 1238a and 1238b are provided at each of the four corners of the base assembly 1236. The patient support structure 1200 may include a lock pedal 1240 to lock operation of the associated rear caster assemblies 1238b as by operator actuation. In some implementations, the patient support structure 1200 may include an actuating push-pull cable that locks the forward casters 1238a in response to locking the rear caster assemblies 1238b.

Figure 13B:
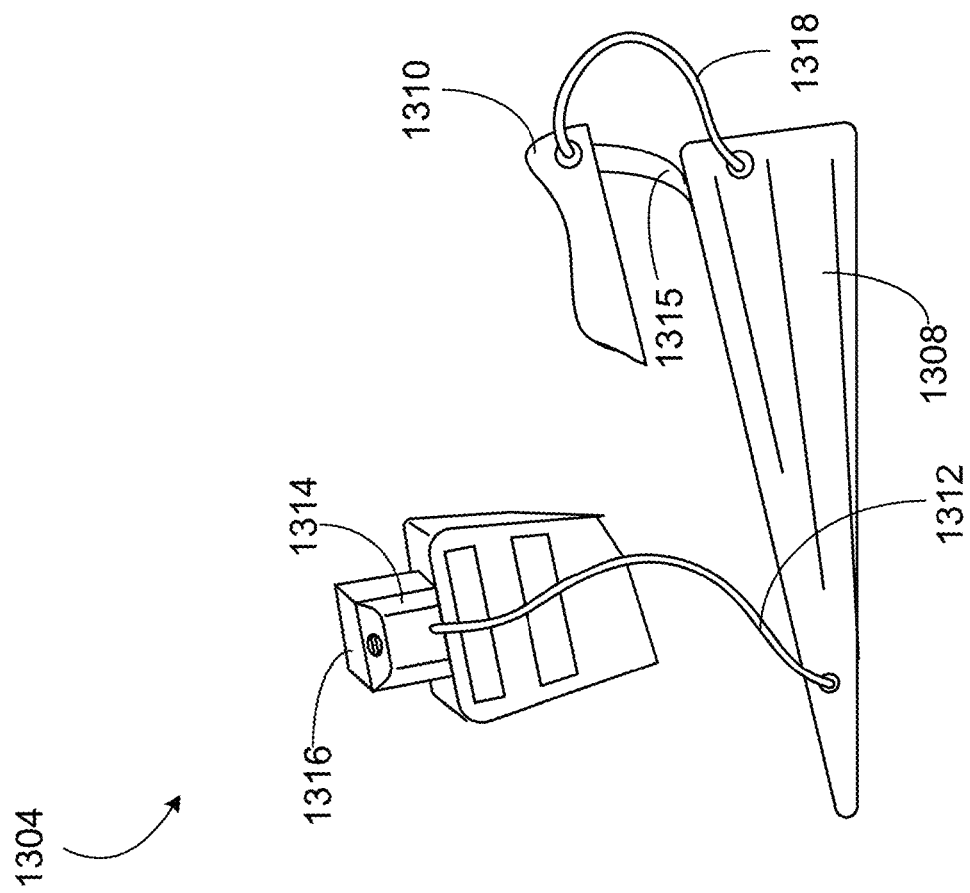

Referring to FIGS. 13A and 13B, another example of a patient support structure is shown. The patient support structure 1300 is configured to support a patient 102. The patient 102 is shown in FIG. 13A for clarity but is not a component of the patient support structure 1300. The patient support structure 1300 may include some or all of the components and functionality of the patient support structure 108 as described above.

A tilt adjuster 1304 of the patient support structure 1300 may include inflation and hydraulic adjustment capabilities. The tilt adjuster 1304 may be coupled to the patient support section 1302. For example, the tilt adjuster 1304 may be removably coupled with hook and loop fasteners, straps, clips, brackets, etc. As shown in FIG. 13B, the tilt adjuster 1304 may include one or more inflation devices (e.g., a bellows 1308 and/or a head support bladder 1310), a pressurized air source 1314, a control unit 1316, and fluid conduits 1312 and 1318. The pressurized air source 1314 may be the CC device 104 or another device configured to enable inflation and/or deflation of the one or more inflation devices.

In an implementation, the tilt adjuster 1304 includes one or more inflation devices configured to elevate and tilt a patient support section of the patient support structure 1300 relative to the base frame 1306. In a further implementation, the one or more inflation devices are configured to elevate and tilt a first portion of the patient's body relative to a second portion of the patient's body. The bellows 1308 is configured to be disposed under the patient support section 1302 (i.e., between the patient support section 1302 and the base frame 1306). When inflated, the bellows 1308 is configured to elevate and tilt the patient support section 1302 relative to the base frame 1306. The head support bladder 1310 is configured to be disposed on top of the patient support section 1302 (i.e., between the patient support section 1302 and the head of the patient 102). When inflated, the head support bladder 1310 is configured to elevate and tilt the head of the patient relative to the torso of the patient. The bellows unit may include one or more air chambers that generate a wedge-shape structure when inflated. The bellows 1308 and the head support bladder 1310 may comprise reinforced PVC, reinforced rubber or other suitable material(s) capable of retaining pressurized air within. In addition, the tilt adjuster 1304 may include connective members 1315 that couple the top and bottom surfaces, respectively, of the bellows 1308 and the head support bladder 1310. The connective members 1315 may be internal webs, beams, and/or a series of cylindrical or otherwise shaped columns that couple the top and bottom surfaces of the bellows 1308 and the head support bladder 1310, can be used. The bellows 1308 and/or the head support bladder 1310 may be coated or covered with various types of materials such as flocking, cotton, flannel, polyester, rayon, etc.

The head support bladder 1310 may be fluidly connected to the bellows 1308 to allow for simultaneous or conditioned pressurization of the bellows 1308 and the head support bladder 1310 via fluid conduit 1312 from the pressurized air source 1314. The patient support structure 1300 may include an automated position adjuster 1380. The automated position adjuster 1380 may be coupled to the CC device mount 1320 and may automatically adjust the position of the CC device relative to the patient support structure 1300. In an implementation, the control unit 1316 may provide a control signal to an automated position adjuster 1380 to automatically adjust the position of the CC device relative to the patient support structure 1300 in response to and based on a change in the tilt angle 1398 and/or 1399.

In various implementations, the pressurized air source 1314 may be the CC device 104 used for CPR treatment or may be an independent pump unit. For instance, the CC device 104 may generate an elevated level of pressure as it compresses the chest. This pressure may be used to effectively inflate, raise, or otherwise adjust the position of the tilt adjuster 1304. As an example, when the CC device 104 compresses the chest, air may be transferred from the CC device 104 to the head support bladder 1310 via the fluid conduit 1312 extending there between. This transfer of air may raise the tilt adjuster 1304 and thereby bring the patient's head and/or other part of the patient's body to an elevated position. The CC device 104 may couple to the patient support structure 1300 at a CC device mount 1320.

The bellows 1308 and the head support bladder 1310 may be fluidly coupled to one another via one or more fluid conduits 1318. The fluid conduits 1318 may include hoses, tubes, valved connectors, non-valved connectors and/or other suitable components The bellows 1308 and the head support bladder 1310 may receive pressurized air from the pressurized air source 1314 via fluid conduit 1312. The fluid conduit 1312 may include hoses, tubes, valved connectors, non-valved connectors and/or other suitable components. The fluid conduit 1312 may be detachably connected to the port of the pressurized air source 1314 and may couple the pressurized air source 1314 to the bellows 1308 and/or the head support bladder 1310. The fluid conduit 1318 may couple the bellows to the head support bladder 1310. In an implementation, the bellows 1308 and the head support bladder 1310 may be inflated at substantially the same pressure. In this case, the one or more fluid conduits 1318 may be non-valved flow paths. Alternatively, if desired, the bellows 1308 and the head support bladder 1310 may be inflated to different pressures. In this case, the one or more fluid conduits 1318 may be valved flow paths. The pressurized air source 1314 may include a pump structure capable of providing pressurized air at independently controllable pressures to the bellows 1308 and the head support bladder 1310 via the respective fluid conduits and flow paths.

When inflated or hydraulically lifted, the bellows 1308 may incline the patient support section 1302 to a first tilt angle 1398 relative to the base frame 1306. For example, the first tilt angle 1398 may be the recommended angle based on one or more of a physiological parameter for the patient, a physiological signal from the patient, a physiological phase of the patient, and a phase of the CPR treatment, as discussed above with regard to FIG. 1. The first tilt angle 1398 may be from zero degrees up to 30 degrees, and possibly from zero degrees up to 20 degrees. When inflated or hydraulically lifted, the head support bladder 1310 tilt the head of a patient laying on the patient support structure 1300 at a second tilt angle 1399 relative to the patient support section 1302. For example, the second tilt angle 1399 may be the recommended angle based on one or more of a physiological parameter for the patient, a physiological signal from the patient, a physiological phase of the patient, and a phase of the CPR treatment, as discussed above with regard to FIG. 1.

The extent of elevation induced by the tilt adjuster 1304 can be controlled by a processor or a user (e.g., the care provider). The control unit 1316 may include a processor communicatively coupled to the pressurized air source and configured to control the inflation of the bellows 1308 and/or the head support bladder 1310. The inflation determines the first tilt angle 1398 and the second tilt angle 1399 which, in turn, determine the tilt associated with body parts of the patient. In an implementation, the control unit 1316 may be the defibrillator 112, as described in reference to FIG. 1. The control unit 1316 may be operably coupled to the pressurized air source 1314, for example by a wired or wireless connection. The care provider may interact with the control unit 1316 to control the operation of the pressurized air source 1314 in supplying pressures to the bellows 1308 and/or the head support bladder 1310.

Referring to FIG. 14, an example of a method 1400 for determining a tilt angle adjustment for a patient's head based on signals from a 3-axis accelerometer is shown. The method 1400 is, however, an example only and not limiting. The method 1400 can be altered, e.g., by having stages added, removed, rearranged, combined, and/or performed concurrently. Although the example of the method 1400 refers to elevation of the patient's head and the patient support section supporting the patient's head, the processor may implement a similar method for other parts of the body and the corresponding supporting sections and tilt angles. For example, the method 1400 may be applied to elevation of the head independently of the chest, of the chest, of the upper legs, and/or of the legs.

Delivery of chest compressions during CPR may increase both arterial and venous pressures simultaneously. Elevating the head of the patient or the head and torso of the patient during CPR may counteract these pressure increases and improve blood flow during CPR. As a result, intracranial pressure may be reduced and cerebral perfusion may be improved. For example, the head of the patient may be elevated by tilting a patient support section supporting the head of the patient to the tilt angle 14.

Figure 15:
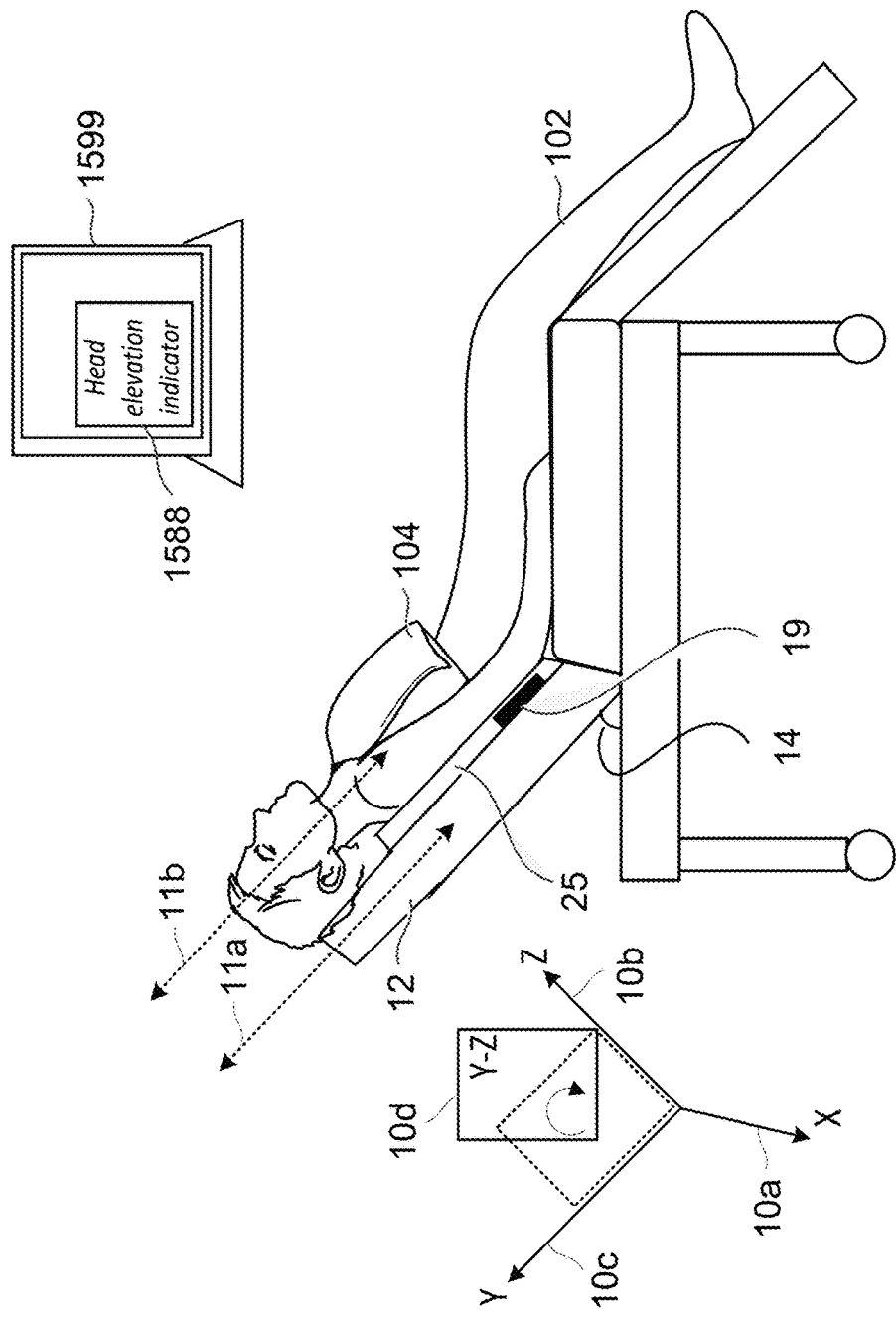
FIG. 15 shows the orientation of the patient and the patient support structure with regard to tilting the patient support section.

In an implementation, the CC device 104 may include an accelerometer assembly 19 configured to detect an angle of tilt of the CC device 104. The accelerometer assembly 19 may be coupled to the backboard 25 or otherwise integrated into the CC device 104. In an implementation, the accelerometer assembly 19 may be disposed in the patient support section 12. Referring to FIG. 15, the orientation of the patient and the patient support structure with regard to tilting the patient support section is shown. As shown in FIG. 15, the CC device 104 is installed on a patient 102 and the patient 102 is supported by the patient support section 12. The craniocaudal axis 11b of the patient is approximately parallel to the longitudinal axis 11a of the patient support section 12. The Y-axis 10c is approximately parallel to the craniocaudal axis 11b and to the longitudinal axis 11a. In order to elevate the head of the patient 102, the patient support section 12 is rotated to a tilt angle 14. This rotation is a rotation of the Y-Z plane 10d (e.g., in the frame of reference indicated by the axes 10a, 10b, and 10c) about the X-axis 10a. When the patient support section 12 is tilted to the tilt angle 14, the accelerometer assembly 19 may detect this angle. The processor 3300 may receive one or more signals from the accelerometer assembly 19 via a wired and/or wireless connection. The processor 3300 may determine the tilt angle 14 based on these signals. For example, the tilt angle module 3318 of the processor 3300 determine the tilt angle 14 and may perform the method 1400. In an implementation, the processor 3300 may perform the method 1400 in cooperation with the system 100 and one or more of the patient support structures 108, 1000, 1100, 1200, and/or 1300. The processor 3300 may provide the determined tilt angle 14 to a user interface 1599 via a wired and/or wireless communicative connection.

The user interface 1599 may display a head elevation indicator 1588. In various implementations, the user interface 1599 may be a component of the defibrillator 112, the local computing device(s) 160, and/or the patient support structure 108. In various implementations, the user interface 1599 may provide the head elevation indicator as a numerical display, a graphic display, a textual display, a color coded display and/or as audible and/or haptic information. The head elevation indicator 1588 may display one or more of the tilt angle 14, an indication that the head of the patient is elevated, and an indication that the tilt angle 14 is within a desired angular range and/or at a target angle. In an implementation, the head elevation indicator 1588 may include a measurement of the tilt angle 14 and a desired range for the tilt angle 14 and/or a desired target for the tilt angle 14.

In an implementation, the accelerometer assembly 19 is affixed to the backboard 25 or the patient support section 12 within the XY plane (e.g., a plane approximately parallel to a top surface of the patient support section 12 with the Y-axis oriented coaxially with a patient's craniocaudal axis 11b, as shown in FIG. 15).

Signals from a 3-axis accelerometer may provide a measure of the angle of a patient support section tilt. That is, the processor 3300 may use signals arising from a 3-axis accelerometer, e.g., the accelerometer assembly 19, affixed to the backboard 25 and/or the patient support section 12, where the patient support section 12 is being tilted, to determine the tilt angle 14 at which the patient support section 12 is tilted, relative to the direction of gravity. In order to determine the angle of tilt, the processor 3300 may sample the values detected by the accelerometer assembly 19. The acceleration is compared to a zero offset to determine if it is a positive or negative acceleration (e.g., if value is greater than the offset then the acceleration is determined as being a positive acceleration). For a positive acceleration, the offset is subtracted from the value and the resulting value is then extracted from a lookup table to determine the corresponding degree of tilt, or the value is determined by a tilt algorithm. If the acceleration is negative, then the value is subtracted from the offset to determine the amount of negative acceleration and then determined using the lookup table or the algorithm. The tilt can be determined within 0° to 90° range for each axis. The tilt may be determined within 0° to 360° range for a two axis configuration (XY, X and Z), or a single axis configuration (e.g. X or Z). The values corresponding to two directions may be converted to degrees and compared to determine the quadrant that they are in. A tilt solution may be solved by either implementing an arccosine function, and arcsine function, or a look-up table depending on the setting of the processor. The angle of the tilt may be used to identify the amount of elevation of one part of the body relative to other parts of the body, for example, the elevation of the head relative to the heart.

At stage 1464, the method 1400 includes acquiring accelerometer data (e.g., raw 3-axis accelerometer data). At stage 1466, the method 1400 includes converting the accelerometer data from units of voltage to units of gravity. At stage 1468, the method 1400 includes determining whether data was collected when the patient support section 12 was static (i.e., a no-motion phase in which the tilt angle 14 remains constant). In some implementations, the algorithm may require the 3-axis accelerometer data to be approximately constant for at least 200 milliseconds. If the static phase did not occur, the method returns to the stage 1464. At stage 1470, in response to determining that the data was collected during a static phase, the method 1400 includes determining a mean of the accelerometer data during the static phase. At stage 1472, the method 1400 includes calculating the tilt angle 14 (e.g., an angle of rotation the Y-Z plane 10d about the X axis 10a) based on the determined mean of the accelerometer data. The method 1400 may be repeated one or more times (e.g., after one or more modifications of a tilt angle of a patient support section). At stage 1474, the method 1400 includes determining whether the tilt angle 14 of the patient support section 12 supporting the patient's head is within a desired range. For example, the range may be between 25 degrees and 35 degrees. As other examples, the range may be between approximately 0 and 40 degrees, between approximately 0 and 30 degrees, between approximately 10 and 30 degrees, between approximately 10 and 20 degrees, between approximately 20 and 30 degrees, between approximately 25 and 30 degrees, or between approximately 20 and 25 degrees. If yes, the method 1400 includes providing tilt angle information to the user interface 1599 at stage 1476. If no, the method 1400 returns to the stage 1464 to determine an adjustment of the tilt angle.

Figure 16:
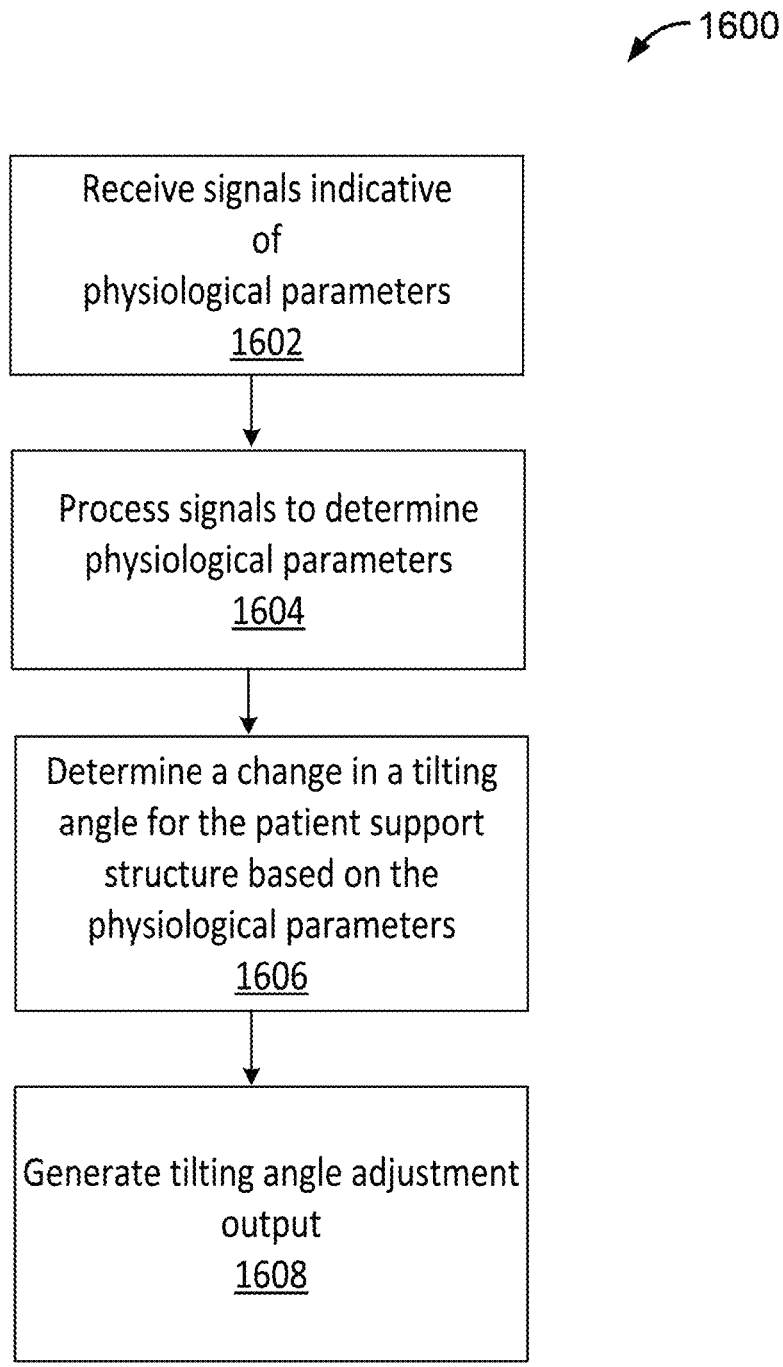
FIG. 16 shows a block diagram of an example of a method for assisting with CPR treatment by adjusting a tilt angle based on a physiological parameter.

FIG. 16 shows an example of a method 1600 for assisting with CPR treatment by adjusting a tilt angle based on a physiological parameter. For example, the processor 3300 may perform the method 1600. In an implementation, the processor 3300 may perform the method 1600 in cooperation with the system 100 and one or more of the patient support structures 108, 1000, 1100, 1200, and/or 1300. However, other implementations are possible. The method 1600 is, however, an example only and not limiting. The method 1600 can be altered, e.g., by having stages added, removed, rearranged, combined, and/or performed concurrently.

At stage 1602, the method 1600 includes receiving one or more signals indicative of one or more physiological parameters. The one or more signals may be received from physiological sensors configured to monitor the patient. For example, the one or more signals may be received by the processor 3300 from an ultrasound transducer, a tonometer, photoplethysmographic sensor, a laser Doppler blood flow sensor, a blood pressure sensor, a motion sensor, a force sensor, an airflow sensor, a pressure sensor, electrocardiogram (ECG) electrodes, electroencephalogram (EEG) electrodes, an ophthalmoscope, an oximetry sensor, an optical sensor and/or a carbon dioxide gas sensor. The signals may be received substantially in real-time. The signals, and physiological parameters associated with the signals, may be associated with a plurality of sites on or near surfaces of the patient's body, such as inferior vena cava, carotid artery, renal artery, brachial artery, femoral artery, abdominal aorta and/or another preferred location. In some implementations, cerebral oxygenation, blood flow, pulse wave velocity, and/or blood pressure may be derived based on signals retrieved with the sensors.

In some implementations, the processor 3300 may provide information about the source of the physiological parameters to a patient monitoring device (e.g., defibrillator 112 shown in FIG. 1). For example, the patient monitoring device may adapt the configuration of a display and/or of analysis tools based on the source of the physiological parameter, such that the axis labels and ranges enable a desirable level of visualization. In some implementations, the physiological parameter is received together with additional patient data, including the depth and rate of chest compressions exerted by the user on the patient, other physiological data recordings, medical history, physical exam findings, and other medical information that might be requested by a user. Patient data may be used in conjunction with patient-specific physiological parameter for data processing and display, or it may be used to correlate information extracted from the physiological parameter.

At stage 1604, the method 1600 includes processing the signal received from the sensor to determine a physiological parameter based on the signal. The physiological parameter provides a time-dependent indication of a physiological state of the patient. Multiple physiological parameter sites may provide different time-dependent physiological parameters that each reflect a particular state (e.g., cardiac oxygenation, cerebral oxygenation, physiological phase of the patient). Additionally, at stage 1604, the patient monitoring device may perform signal pre-processing substantially in real time. Real time signal pre-processing may include removing the DC component with a high-pass filter, amplifying the physiological parameter, limiting the signal bandwidth with a low-pass filter and digitally sampling the physiological parameter. It will be appreciated that the processing may provide an indication of response to CPR treatment substantially in real-time, including within a meaningful time to allow the care provider 106 and/or the tilt controller 180 to modify tilt angles and/or levels of elevation and chest compression rates, if needed.

Processing the signal and determining the physiological parameter may include determining the occurrence of a feature in a portion of the physiological parameter, for example a feature in an arterial or venous waveform. In some implementations, the determined feature is indicative of a change (e.g., reduction) in oxygenation, arterial flow, blood pressure, and/or backward flow. The portion of an arterial or venous waveform can correspond to the systolic and/or diastolic phase. For example, where the arterial (or venous) waveform is monitored, identifying a portion of the waveform may include determining an onset of a chest compression and an end of the compression (i.e. the onset of compression downstroke and end of upstroke). Other fiducial points may also be used to determine a portion of the waveform to be analyzed. In some implementations, each waveform portion to be analyzed is determined based on a simultaneously recorded ECG.

In some implementations, the information about a plurality of waveform portions is used to calculate a reference portion and store the reference portion in a memory (e.g., the memory 1920). In some implementations, statistical shape analysis may be used to characterize the waveform or groups of waveforms. For example, a reference portion may be generated automatically at the beginning of the CPR treatment session or it may be obtained based on a database of waveforms. There may be a user input on the patient monitoring device to allow the user to manually initiate a new acquisition of the reference portion and/or the monitored portion. The reference portion may be determined for two or more waveforms corresponding to different arterial or venous targets (e.g., inferior vena cava, carotid artery, jugular vein, renal artery, brachial artery, femoral artery, abdominal aorta, etc.). In some implementations, the reference portion will be determined as described above, or it may correspond to 100 seconds up to 10 minutes. The time period may be configured in the non-volatile storage memory of the patient monitoring device.

In certain implementations, statistical shape analysis may be employed. Such shape analysis includes methods for studying the geometrical properties of objects, such as a waveform. The constraints may be determined from historical data (e.g. by machine learning) giving the model flexibility, robustness and specificity as the model synthesizes plausible instances with respect to the observations. In order to determine whether an object, e.g. a waveform portion, or feature of the waveform, has changed shape, the shape of the object is first determined. In addition to using the shape analysis of a waveform portion, other parameters may be used in the analysis, for example, a landmark, an anatomical landmark, mathematical landmarks, etc.

Analysis of the baseline and/or reference portion (or value) of one or more physiological parameters in comparison to the monitored portion (or value) of the one or more physiological parameters may be determined substantially in real-time. Such analysis may be used to determine whether there may be a decrease of cerebral oxygenation, cardiac output or blood flow. The occurrence of a decrease of cardiac output and/or blood flow may be calculated or estimated by a variety of methods. In some examples, the decrease of cerebral oxygenation, cardiac output and/or blood flow may be determined based on a mathematical model, such as one based on logistic regression. Examples of logistic regression models that may be used include univariate analysis or multivariate non-linear regression.

In an implementation, the identification of the decrease of cerebral oxygenation, cardiac output and/or blood flow may be determined at regular intervals such as 10 seconds, 100 seconds, or 1 minute. The logistic model may take into account the first, second and higher order derivatives of the shape distance between the first and second portions of physiological parameters (e.g. an arterial or venous waveform). In other words, if the distance is diverging more rapidly, that may be a sign of the patient's condition degenerating more rapidly and this in itself may indicate the decrease in cerebral oxygenation, cardiac output and/or blood flow. An analysis, such as a statistical one, is performed on physiological parameter trajectories for the different compression cycles. Such analysis may be used to determine or estimate whether cerebral oxygenation, cardiac output and/or blood flow is decreasing or increasing, and may be used as a basis for determining to what degree at least a portion of the patient's upper body should be tilted and/or elevated.

In some implementations, the characterization may be based on an average or median of a value of a physiological parameter corresponding to a plurality of compression cycles. In some implementations, the average or median of a value of a physiological parameter obtained from within the previous 5 seconds up to 10 minutes from present time may be used. The time period from which the average or median of the value of the physiological parameter is determined may be separated by at least 5 seconds from the time period corresponding to a reference period (e.g. obtained at the beginning of CPR or from a patient physiological database).

The analysis of a new set of test physiological parameters may be based on a time threshold (e.g., a new set of physiological parameters is analyzed every 10 minutes or every 100 minutes) or may be based on a physiological trigger such as the start of a new compression cycle (e.g. corresponding to multiple compressions). A physiological parameter value and/or feature may be determined for a particular compression that may be included in the set of test physiological parameters. The processor 3300 may monitor the length of time for which the one or more physiological parameters are measured based on predetermined criteria. For example, the size of the test set may be based on a threshold number of physiological parameters and/or on a time based threshold. If the size of the test set has not been reached, the processor 3300 may continue to determine physiological parameter values and/or features to add to the test set. If the size of the test set has been reached, the processor 3300 may characterize the test set of physiological parameters.

In some implementations, the occurrence of a feature of interest in the physiological parameter may be identified by comparing the test physiological parameter trajectory to a control physiological parameter trajectory. The feature may be identified based on a statistical analysis. For example, a variation of the physiological parameter trajectory from the control physiological parameter trajectory that occurs for a portion of the physiological parameter and exceeds the standard deviation of the control physiological parameter trajectory may be identified as the occurrence of the feature of interest.

In some implementations, the signal may be processed over multiple consecutive compressions of a plurality of compression cycles to determine a trend of the physiological parameter and based on the trend, to define a decrease of cerebral oxygenation, cardiac output and/or blood flow. For example, the action of identifying a cerebral oxygenation feature and monitoring the feature may be repeated (e.g. over multiple compression cycles) and/or conducted substantially continuously during CPR. For example, the occurrence of a feature in the signal and/or a value of the physiological parameter determined therefrom may be identified for each recorded compression cycle, after the control physiological parameter trajectory was determined.

At stage 1606, the method 1600 includes determining a change in a tilt angle for the patient support structure based on the monitored and/or processed physiological parameters. For example, processor 3300 may determine a change in one or more of the tilt angles 109a, 109b, 109c, and 109d for a corresponding section of the patient support structure. In an implementation, the method may include determining the elevation of the one or more sections of the patient support structure (e.g., the elevation 110a, 110b, and/or 110c). The change of the tilt angle may include a decrease or an increase of the tilt angle relative to previously set tilt angles. The change of the tilt angle may be based on the identification of the occurrence of a feature in the physiological parameter, the recorded CPR signal or another input useful for determining how various portions of the patient's body should be elevated and/or tilted. For example, if the monitored physiological parameter is characterized by a trend that indicates a gradual decrease in cerebral oxygenation and/or blood flow over multiple heart beats, during which CPR was applied using the same compression depth and rate (e.g., 100 chest compressions per minute), the processor 3300 may determine that the revised tilt angle includes an increase in patient's head tilt angle. In some implementations, the optimal change of tilt angle may be proportional to the changing trend of the physiological parameter. In an implementation, the stage 1606 may include determining CPR compression feedback based on the physiological parameters (e.g., feedback for chest compression rate, chest compression depth, chest release, release velocity, etc.).

At stage 1608, the method 1600 includes generating a tilt angle adjustment output comprising one or more of a control signal and user feedback. The control signal and/or the user feedback may be indicative of the determined change in the tilt angle. In an implementation, the control signal and/or the user feedback may be indicative of a target tilt angle based on the determined change in the tilt angle. The processor 3300 may provide the user feedback to a user interface of the system 100. For example, the defibrillator 112 and/or the local computing device(s) 160 may display the user feedback. Alternatively or additionally, the processor 3300 may provide the control signal to the tilt controller 180. The tilt controller 180 may automatically adjust one or more tilt angles in response to the control signal from the processor 3300. In a further implementation, the user feedback may include the determined CPR compression feedback. Additionally or alternatively, the method 1600 may include generating a control signal for the CC device 104 based on the determined CPR compression feedback. In some implementations, the user feedback may include an alarm that alerts a user of the patient support structure 108 of a required or recommended update of one or more tilt angles.

The example method 1600 may be repeated one or more times, such that the tilt angle associated is adjusted one or more times, based on the physiological parameters, until the completion of CPR treatment. For example, if compression characteristics are within desired target ranges and/or the physiological parameter indicates a target, desirable and/or improving physiological patient condition (e.g., sufficient oxygenation, vascular tone, etc.), CPR parameters may be considered adequate and no changes are made to the current treatment (e.g., tilt adjustment, metronome change, and/or generation of additional prompts). As another example, if the physiological parameter indicates an undesirable and/or deteriorating an arterial or venous waveform is measured and it indicates a decrease in cerebral oxygenation, vascular tone, tilt angle and/or CPR may be considered inadequate, revised elevation, tilt angle and/or rate of chest compressions may be determined. As a result, the care giver may be prompted to modify CPR based on the newly identified tilt angle and/or rate of chest compressions and/or the tilt angle of the patient support apparatus may be modified (e.g., raised, lowered) as desired with the intent of increasing the effectiveness of CPR.

Figure 17:
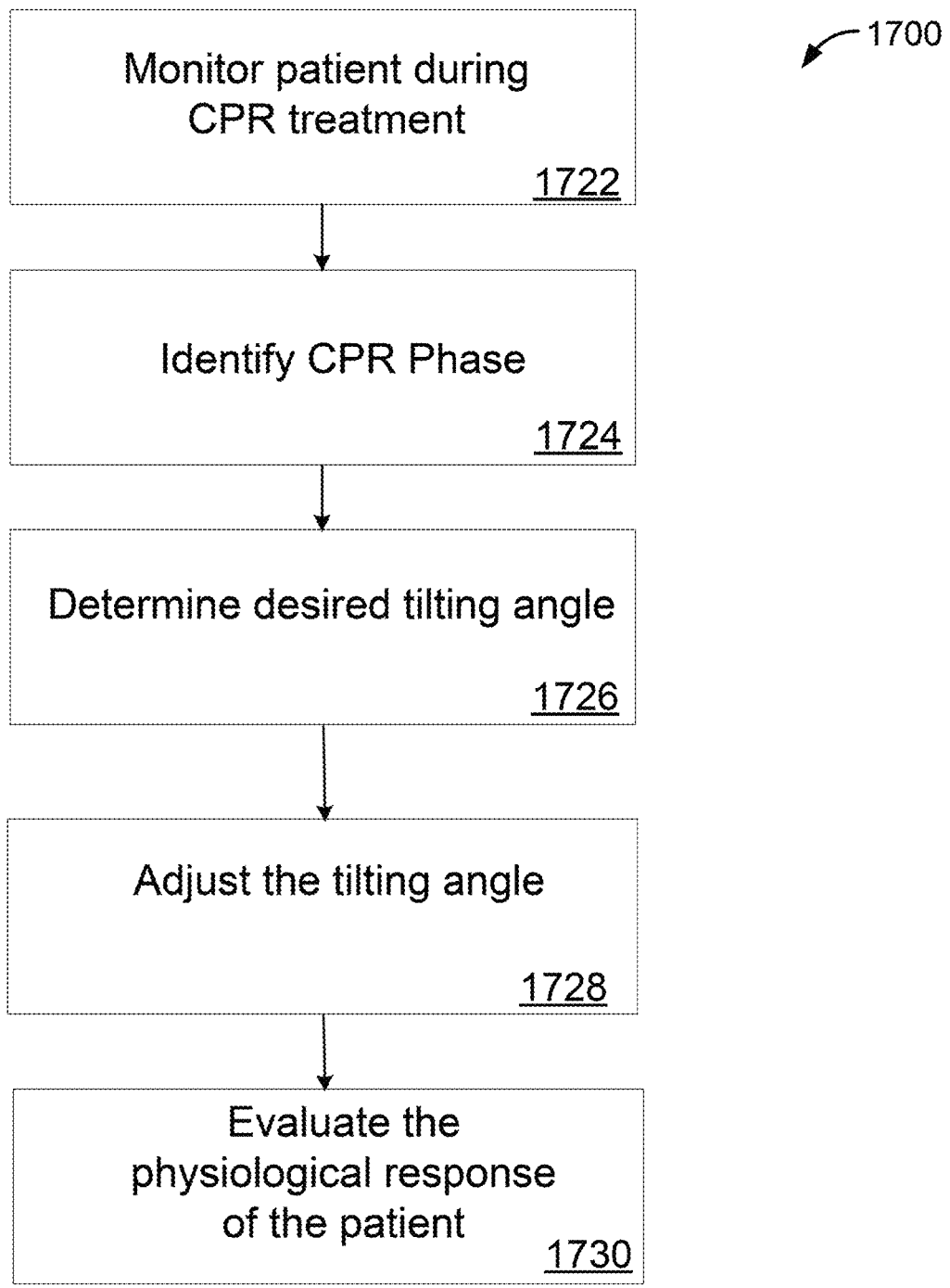
FIG. 17 shows a block diagram of an example of a method for assisting with CPR treatment by determining a tilt angle based on identification of a CPR treatment phase.

Referring to FIG. 17, an example of a method 1700 for assisting with CPR treatment by determining a tilt angle based on identification of a CPR treatment phase is shown. For example, the processor 3300 may perform the method 1700. In an implementation, the processor 3300 may perform the method 1700 in cooperation with the system 100 and one or more of the patient support structures 108, 1000, 1100, 1200, and/or 1300. However, other implementations are possible. The method 1700 is, however, an example only and not limiting. The method 1700 can be altered, e.g., by having stages added, removed, rearranged, combined, and/or performed concurrently.

The patient may be aligned to an alignment feature of the patient support structure. CPR treatment may be applied to the patient manually or may be applied automatically using the CC device 104. The device may be configured to actively compress and/or actively decompress the chest of the patient or to permit passive decompression of the chest of the patient at a first compression rate and depth of a variable resuscitation protocol.

At stage 1722, the method 1700 includes monitoring the patient during the CPR treatment. For example, one or more sensors may provide signals indicative of the phase of CPR treatment to the processor 3300. In some cases, the sensor(s) (e.g., a motion sensor, a pressure sensor, a blood flow sensor, an ECG electrode, etc.) may detect the onset of chest compressions, ventilations and/or other CPR related activity. In some implementations, a plurality of sensors (e.g., ECG electrodes, CPR sensor, blood pressure sensor, SpO2 sensor, etc.) may be attached to the patient to monitor one or more physiological signals during CPR treatment. Alternatively, the processor 3300 may determine the phase of CPR treatment without requiring a physiological sensor. For example, an automated CC device may administer chest compressions to the patient and the processor 3300 may determine the type of CPR treatment provided to the patient based on signals received from the automated CC device. As another example, the care provider may provide input for the processor 3300. One or more user interfaces associated with one or more of the defibrillator 112, the remote computing device 119, the local computing device(s) 160, the patient support structure 108, and the therapeutic delivery device(s) 158 may capture the input from the care provider. The input may indicate a phase of CPR treatment. For example, the user may input into the processor 3300 that chest compressions, electrotherapy, ventilations, or another type of CPR treatment is currently being provided. One or more sections of the patient support structure 108 may be positioned at one or more first tilt angles. The one or more first tilt angles may include an angle of zero such that the patient is in a supine position on the patient support structure 108. The first tilt angle may be between 1 and 90 degrees such that the head of the patient is elevated higher than the torso.

At stage 1724, the method 1700 includes identifying the phase of CPR treatment. Optionally, at the stage 1724, the method 1700 includes determining an amount of time elapsed since the CPR treatment commenced. The amount of time may be determined by a timer module. The timer module may be integrated into a device in the system 100. The process compares the amount of time elapsed since the CPR treatment commenced to a threshold to distinguish between multiple CPR treatment phases. The threshold may be set between approximately 15 and 25 minutes. In some implementations, the threshold may be set at 20 minutes. The comparison may be performed at preset intervals (e.g., every second or every minute). In some implementations, the stage 1024 may also include a comparison of recorded physiological signals to control physiological signals or critical ranges.

At stage 1726, the method 1700 includes determining a desired tilt angle. In an implementation, the stage 1726 includes determining a desired tilt angle range based on the identified CPR phase.

At a stage 1728, the method 1700 includes adjusting the tilt angle of the patient support section based on the desired tiling angle. For example, the method 1700 may include the method 1400 for determining and adjusting the tilt angle. The change of elevation and/or tilt angle rate may include an increase or a decrease of tilt angle. Optionally, the change in tilt angle may include a change in angle relative to the first tilt angle. The preferred change of tilt angle may be based on the amount of time elapsed since the CPR treatment commenced.

At stage 1730, the method 1700 optionally includes evaluating the physiological response of the patient to the adjustment of the tilt angle based on one or more physiological parameters. For example, the physiological parameters may include one or more features of an arterial or venous waveform. In an implementation, the physiological parameter of the patient may be compared to a threshold value, a target value, and/or to a previous value or group of values. Based on the comparison and/or other algorithmic determination, it may be identified that the tilt angle requires further adjustment. In response to evaluating the physiological response of the patient, the method 1700 may optionally include adjusting CPR performance parameters or recommendations. The processor 3300 may automatically control the CC device 104 and/or may provide CPR feedback for the care provider.

As examples, the method may include readjustment of tilt angles and/or CPR procedures if the physiological parameters indicate a critical physiological state. For example, if blood oxygenation is measured and it indicates a decrease to a critical value before the amount of time elapsed since the CPR treatment commenced reached the threshold, CPR may be considered inadequate. If the applied CPR is determined as being inadequate, a revised rate of chest compressions may be determined and the user may be prompted to modify CPR based on the revised rate of chest compressions.

Referring to FIG. 18, a plot 1800 of experimental data obtained from swine administered CPR treatment at various degrees of tilt angles is shown. It should be understood that the plot 1800 is not limiting of the various possible implementations that may be employed and is provided as an example experimental case. Hemodynamics were studied in 14 domestic swine (~20 kg) using standard physiological monitoring. Primary outcome variables included intracranial pressure in the left parietal lobe of the brain, cerebral perfusion pressure (calculated as mean aortic pressure-mean intracranial pressure), and cerebral oxygenation measured on the right parietal lobe of the brain.

After 6 minutes of untreated VF, CPR treatment with load-distributing band (LDB) compressions was initiated at a zero degree tilt. Each animal received break-in LDB-CPR (mild/low compression depth) for approximately 45 to 60 seconds followed by a progressive increase in compression depth over the next 2 minutes to achieve a coronary perfusion pressure (CPP) of at least 15 mmHg. Three experimental groups were studied. Each experimental group had three interventions performed after break-in LDB-CPR and optimized depth was determined. The first group (N=7) examined the hemodynamic effect of varying whole body tilt (30 degrees, 10 degrees, and then 20 degrees head-up tilt). The second group (N=5) examined the effect of constant tilt (30 or 20 degrees head-up tilt) with varying levels of depth of compression (optimized compression depth based on CPP, reduced compression depth, and then back to optimized compression depth). The third group (N=2) examined the effect of varying levels of depth of compression similar to the second group but without head-up tilt. Epinephrine was given in all groups as the fourth intervention and up to three rescue defibrillations were attempted after observing the epinephrine effect (increased aortic pressures).

Cerebral oxygenation values ranged from 53-68% before VF was induced. After 6 minutes of untreated VF, cerebral oxygenation values were reduced to 24-31%. Cerebral oxygenation improved with optimized LDB-CPR and with head-up tilt. Optimizing the depth of compression to achieve a CPP of 15 mmHg at 0 degree head-up tilt always increased cerebral oxygenation (absolute increase of +4.6±0.6%). The act of increasing head-up tilt from 0 to 30 or 20 degrees increased cerebral oxygenation in 10 of the 12 experiments (two animals had values that remained the same) with an absolute average increase of +4.0±0.6%. Increased head-up tilt was also significantly associated with an increased cerebral perfusion pressure, which was primarily driven by a substantial reduction in intracranial pressure. Mean aortic pressure was reduced, which lead to either sustained or reduced CPP during head-up tilt.

Depth of chest compression did not appear to have a significant association to the cerebral oxygenation. Reducing chest compression depth did not result in sizeable reductions in cerebral oxygenation despite the substantial reductions seen in aortic, right atrial, intracranial pressures, and carotid blood flow which again could be attributed to assumptions of the underlying algorithms used in NIRS devices. In the experiments in which ROSC was obtained (n=7), cerebral oxygenation values progressively increased but rarely obtained the same value as baseline/pre-VF.

A result of interest indicates how quickly the cardiovascular health of the animal could be compromised by reducing the head-up tilt position back to zero degrees after a successful defibrillation and obtaining ROSC. In one of the early experiments, ROSC was obtained in a 20 degree head-up tilt position and re-arrest occurred immediately when the tilt position was quickly moved (1-3 degrees/second) to zero degree tilt while in another experiment the change in tilt resulted in a significant period of hemodynamic instability. After these two observations, the change in tilt from 30 or 20 degrees to 0 degrees was done slowly (1-3 degrees/minute) and with careful consideration of the hemodynamic status of the animal.

The exploratory experimental series confirmed that head-up tilt improves cerebral oxygenation with LDB-CPR. On average, the combination of optimized chest compression depth and 30 or 20 degree head-up tilt resulted in a ≈30% relative increase in cerebral oxygenation from prior to starting LDB-CPR. In general, the non-invasive NIRS technology displayed expected trends for cerebral oxygenation (substantial decreases after inducing VF, increased values with head-up tilt and CPR and when ROSC was obtained). In this particular experimental example, no changes in cerebral oxygenation were detected when CPR depth was changed, which could be a result of the algorithms used in the commercial devices tested, a false assumption about the association between depth of compression and cerebral oxygenation, or some other unknown aspect to the physiology of chest compression generated blood flow. These observations suggest that there are methods to perform CPR, which are more protective for the brain but less so for the heart, and vice versa.

Referring back to FIG. 18, it is shown that for both examples, Case 001 and Case 002, adjusting the angle of tilt of the head had notable effects on the cerebral oxygenation. That is, prior to inducement of VF, the cerebral oxygenation was at normal levels, approximately 54-57%, and when VF was induced, the cerebral oxygenation plummeted significantly to approximately 24-28%. However, with chest compressions and elevation of the support surface from 0 degrees to 30 degrees, the cerebral oxygenation was immediately observed to increase. As the degree of tilt was reduced from 30 degrees to 10 degrees, the cerebral oxygenation was observed to decrease. However, when the degree of tilt was raised from 10 degrees to 20 degrees, the cerebral oxygenation was then observed to increase. For Case 001, when the degree of tilt was adjusted from 10 degrees to 20 degrees, the cerebral oxygenation at 20 degrees was observed to be greater than when the cerebral oxygenation was measured at 30 degrees. However, for Case 002, when the degree of tilt was adjusted from 10 degrees to 20 degrees, the cerebral oxygenation at 20 degrees was observed to be slightly less than when the cerebral oxygenation was measured at 30 degrees.

The results shown in FIG. 18 provide an indication that while the measure of cerebral oxygenation may be linked to the elevation of the head, a number of factors are at play in the overall physiological response. That is, the manner and pattern with which the head is elevated so as to provide the most physiological benefit to the patient will vary from situation to situation and is unlikely to fit within a single recipe or protocol. As shown in this example, the degree of tilt of the body does not necessarily provide a one to one correspondence with cerebral oxygenation. Instead, the physiological measurement(s) (e.g., cerebral oxygenation, cerebral perfusion pressure, intracranial pressure, coronary perfusion pressure, etc.) provide information that, taken in context with the physiological and treatment history of the patient, will be beneficial for a care giver to use as a reference point in determining the type of subsequent treatment that should be administered to the patient. In various embodiments, the system may utilize one or more inputs in accordance with the present disclosure in an optimization process that provides feedback (e.g., prompts, control signals to the patient support structure and/or user interface, user instructions) for raising or lowering the head of the patient.

Figure 19:
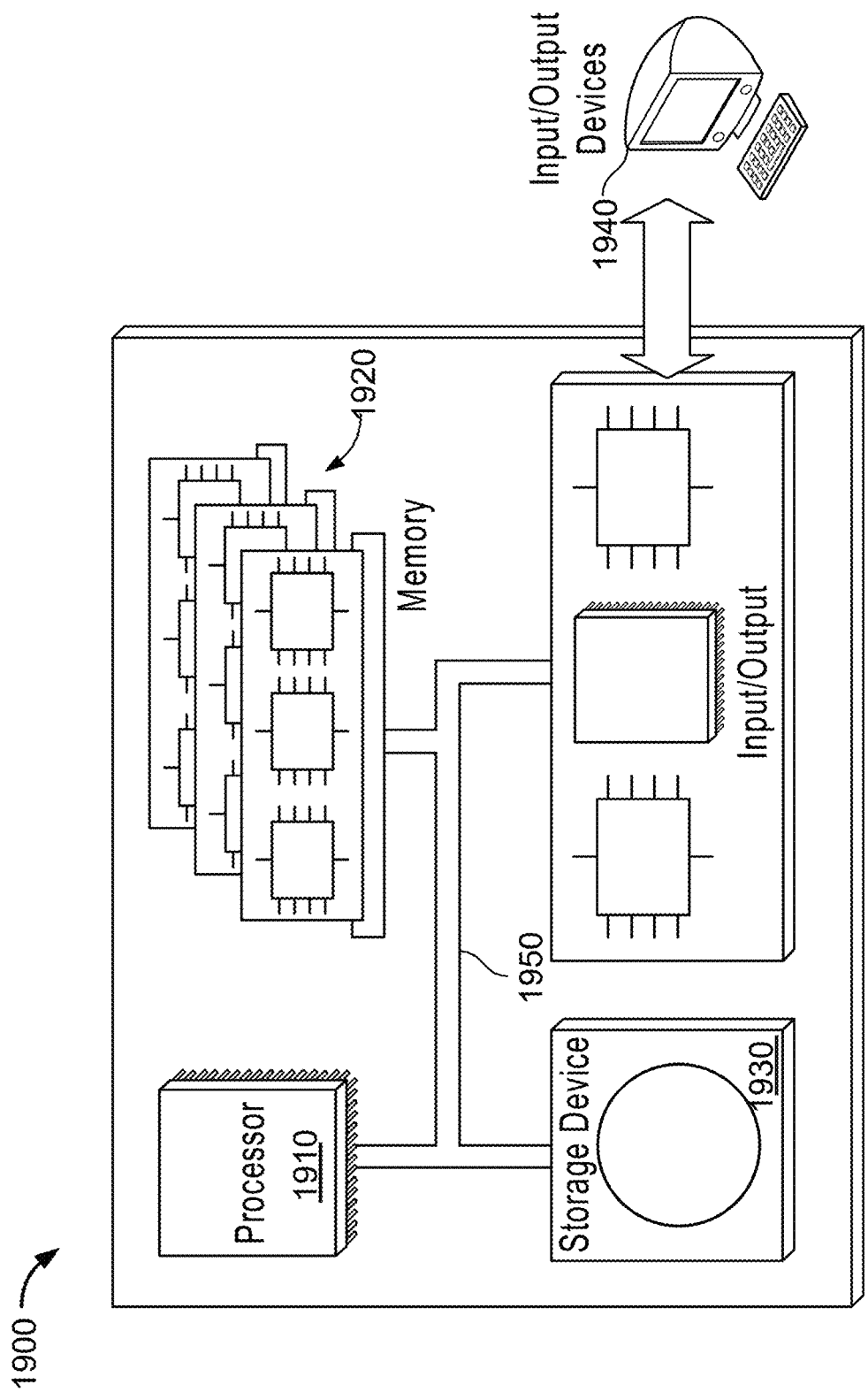
FIG. 19 shows an example of a computer system in accordance with various embodiments.

Referring to FIG. 19, an example of a computer system in accordance with various embodiments is shown. The computer system 1900 may be a computing device or a group of communicatively coupled computing devices. Claimed subject matter is not limited to a particular type, category, size, etc. of computing device.

The particular techniques described here can be assisted by the use of a computer-implemented medical device, such as defibrillator 112 that includes computing capability. The computing portions of such defibrillator 112 or other device (e.g., the CC device 104, the local computing devices 160, the tilt controller 180, the remote computing devices 119, and/or the therapeutic delivery devices 158) is shown generally in FIG. 19, and may communicate with and/or incorporate a computer system 1900 in performing the operations discussed above, including operations for computing the quality of one or more components of CPR provided to a victim and generating feedback to care providers, including feedback to change care providers who are performing certain components of the CPR. The system 1900 can be implemented in various forms of digital computers, including computerized defibrillators laptops, personal digital assistants, tablets, and other appropriate computers. Additionally the system can include portable storage media, such as, Universal Serial Bus (USB) flash drives. For example, the USB flash drives may store operating systems and other applications. The USB flash drives can include input/output components, such as a wireless transmitter or USB connector that can be inserted into a USB port of another computing device.

The computer system 1900 may include a processor 1910, a memory 1920, and an input/output device 1940. In an implementation, the computer system 1900 may further include a storage device 1930. The components 1910, 1920, 1930, and 1940 are communicatively coupled (directly and/or indirectly) to each other for bi-directional communication via a system bus 1950. The processor 1910 and the memory 1920 may include and/or be coupled to associated circuitry in order to perform the functions described herein.

The processor 1910 is capable of processing instructions for execution within the system 100. The processor can be designed using any of a number of architectures. For example, the processor 1110 can be a CISC (Complex Instruction Set Computers) processor, a RISC (Reduced Instruction Set Computer) processor, or a MISC (Minimal Instruction Set Computer) processor. In one implementation, the processor 1910 is a single-threaded processor. In another implementation, the processor 1910 is a multi-threaded processor. The processor 1910 is capable of processing instructions stored in the memory 1920 or on the storage device 1930 to display graphical information for a user interface on the input/output device 1940. The processor 1910 is a physical processor (i.e., an integrated circuit configured to execute operations on the computer system 1900 as specified by software and/or firmware). The processor 1910 may be an intelligent hardware device, e.g., a central processing unit (CPU), one or more microprocessors, a controller or microcontroller, an application specific integrated circuit (ASIC), a general-purpose processor, a digital signal processor (DSP), or other programmable logic device, a state machine, discrete gate or transistor logic, discrete hardware components, or any combination thereof designed to perform the functions described herein and operable to carry out instructions on the computer system 1900. The processor 1910 utilize various architectures including but not limited to a complex instruction set computer (CISC) processor, a reduced instruction set computer (RISC) processor, or a minimal instruction set computer (MISC). In various implementations, the processor 1910 may be a single-threaded or a multi-threaded processor. The processor 1910 may be one or more processors and may be implemented as a combination of computing devices (e.g., a combination of DSP and a microprocessor, a plurality of microprocessors, one or more microprocessors in conjunction with a DSP core, or any other such configuration). The processor 1910 may include multiple separate physical entities that may be distributed in the computer system 1900. The processor 1910 is configured to execute processor-readable, processor-executable software code containing one or more instructions or code for controlling the processor 1910 to perform the functions as described herein.

The processor 1910 is operably coupled to the memory 1920. The memory 1920 refers generally to any type of computer storage medium, including but not limited to RAM, ROM, FLASH, disc drives, fuse devices, and portable storage media, such as Universal Serial Bus (USB) flash drives, etc. The USB flash drives can store operating systems and other applications. The USB flash drives can include input/output components, such as a wireless transmitter and/or USB connector that can be inserted into a USB port of another computing device. The memory 1920 may be long term, short term, or other memory associated with the computer system 1900 and is not to be limited to any particular type of memory or number of memories, or type of media upon which memory is stored. The memory 1920 includes a non-transitory processor-readable storage medium (or media) that stores the processor-readable, processor-executable software code.

The storage device 1930 is a mass storage device for the system 1900. In an implementation, the storage device 1930 is a computer-readable medium. In various implementations, the storage device 1930 may be, for example, a floppy disk device, a hard disk device, an optical disk device, or a tape device.

The input/output device 1940 may be a one or more of a display, a speaker, and a haptic device. The display may provide a graphical user interface (GUI). The display may be, for example, but not limited to, a liquid crystal display (LCD) and/or a light emitting diode (LED) display. In an implementation the input/output device 1940 may be an input/output device capable of capturing user input (e.g., a touch screen). The processor 162 may control the input/output device 1940 to provide one or more of visible feedback, audible feedback, haptic feedback, numerical feedback, and graphical feedback. The feedback may include chest compression parameter feedback and/or resuscitative care feedback. Alternatively, or additionally, the processor 162 may control the input/output device 1940 to provide instructions, alarms, treatment event reminders, treatment event timing information, and/or combinations thereof. The processor 162 may further control the input/output device 1940 to provide resuscitative care prompts and/or instructions for the rescuer. For example, the resuscitative care prompts may include one or more of a prompt to start resuscitative treatment, a prompt to determine if the victim requires CPR, a prompt to start the manual chest compressions, a prompt to determine if the rescuer wants to provide the automated chest compressions, a prompt to attach an automated chest compression device to the victim, and a prompt to determine if the rescuer wants to continue CPR.

The input/output device 1940 may be a component of the local computing device 160. Alternatively, or additionally, the input/output device 1940 may be a discrete component communicatively coupled to the local computing device 160. The communicative connection between the input/output device 1940 and the local computing device 160 may be include wired and/or wireless connections. In an implementation, the input/output device 1940 may include a display unit for displaying graphical user interfaces. The input/output device may include, for example, a touch screen, a keyboard, a mouse, joystick, trackball, or other pointing device, a microphone, a camera, etc.).

Other Considerations

The features described can be implemented in digital electronic circuitry, or in computer hardware, firmware, software, or in combinations of them. The apparatus can be implemented in a computer program product tangibly embodied in an information carrier, e.g., in a machine-readable storage device for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device.

A computer program is a set of instructions that can be used, directly or indirectly, in a computer to perform some activity or bring about some result. A computer program can be written in any form of programming language, including compiled or interpreted languages, and it can be deployed in any form, including as a stand-alone program or as a module, component, subroutine, or other unit suitable for use in a computing environment. Storage devices suitable for tangibly embodying computer program instructions and data include all forms of non-volatile memory, including by way of example semiconductor memory devices, such as EPROM, EEPROM, and flash memory devices, magnetic disks such as internal hard disks and removable disks, magneto-optical disks, and CD-ROM and DVD-ROM disks.

The computing devices described herein may include, or be operatively coupled to communicate with, one or more mass storage devices for storing data files; such devices include magnetic disks, such as internal hard disks and removable disks; magneto-optical disks; and optical disks.

The terms "machine-readable medium," "computer-readable medium," and "processor-readable medium" as used herein, refer to any medium that participates in providing data that causes a machine to operate in a specific fashion. Using a computer system, various processor-readable media (e.g., a computer program product) might be involved in providing instructions/code to processor(s) for execution and/or might be used to store and/or carry such instructions/code (e.g., as signals).

In many implementations, a processor-readable medium is a physical and/or tangible storage medium. Such a medium may take many forms, including but not limited to, non-volatile media and volatile media. Non-volatile media include, for example, optical and/or magnetic disks. Volatile media include, without limitation, dynamic memory.

Common forms of physical and/or tangible processor-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, EPROM, a FLASH-EPROM, any other memory chip or cartridge, a carrier wave as described hereinafter, or any other medium from which a computer can read instructions and/or code.

Various forms of processor-readable media may be involved in carrying one or more sequences of one or more instructions to one or more processors for execution. Merely by way of example, the instructions may initially be carried on a flash device, a device including persistent memory, and/or a magnetic disk and/or optical disc of a remote computer. A remote computer might load the instructions into its dynamic memory and send the instructions as signals over a transmission medium to be received and/or executed by a computer system.

The computing devices described herein may be part of a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include a local area network ("LAN"), a wide area network ("WAN"), peer-to-peer networks (having ad-hoc or static members), grid computing infrastructures, and the Internet. The computer system can include clients and servers. A client and server are generally remote from each other and typically interact through a network, such as the described one. The relationship of client and server arises by virtue of computer programs running on the respective computers and having a client-server relationship to each other.

Substantial variations may be made in accordance with specific requirements. For example, customized hardware might also be used, and/or particular elements might be implemented in hardware, software (including portable software, such as applets, etc.), or both. Further, connection to other computing devices such as network input/output devices may be employed.

Information and signals may be represented using any of a variety of different technologies and techniques. For example, data, instructions, commands, information, signals, and symbols that may be referenced throughout the above description may be represented by voltages, currents, electromagnetic waves, magnetic fields or particles, optical fields or particles, or any combination thereof.

The methods, systems, and devices discussed above are examples. Various alternative configurations may omit, substitute, or add various procedures or components as appropriate. Configurations may be described as a process which is depicted as a flow diagram or block diagram. Although each may describe the operations as a sequential process, many of the operations can be performed in parallel or concurrently. In addition, the order of the operations may be rearranged. A process may have additional stages not included in the figure. Specific details are given in the description to provide a thorough understanding of example configurations (including implementations). However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations will provide those skilled in the art with an enabling description for implementing described techniques. Various changes may be made in the function and arrangement of elements without departing from the scope of the disclosure.

Also, configurations may be described as a process which is depicted as a flow diagram or block diagram. Although each may describe the operations as a sequential process, many of the operations can be performed in parallel or concurrently. In addition, the order of the operations may be rearranged. A process may have additional stages or functions not included in the figure. Furthermore, examples of the methods may be implemented by hardware, software, firmware, middleware, microcode, hardware description languages, or any combination thereof. When implemented in software, firmware, middleware, or microcode, the program code or code segments to perform the tasks may be stored in a non-transitory processor-readable medium such as a storage medium. Processors may perform the described tasks.

Components, functional or otherwise, shown in the figures and/or discussed herein as being connected or communicating with each other are communicatively coupled. That is, they may be directly or indirectly connected to enable communication between them.

As used herein, including in the claims, "and" as used in a list of items prefaced by "at least one of" indicates a disjunctive list such that, for example, a list of "at least one of A, B, and C" means A or B or C or AB or AC or BC or ABC (i.e., A and B and C), or combinations with more than one feature (e.g., AA, AAB, ABBC, etc.). As used herein, including in the claims, unless otherwise stated, a statement that a function or operation is "based on" an item or condition means that the function or operation is based on the stated item or condition and may be based on one or more items and/or conditions in addition to the stated item or condition.

Having described several example configurations, various modifications, alternative constructions, and equivalents may be used without departing from the disclosure. For example, the above elements may be components of a larger system, wherein other rules may take precedence over or otherwise modify the application of the invention. Also, a number of operations may be undertaken before, during, or after the above elements are considered. Also, technology evolves and, thus, many of the elements are examples and do not bound the scope of the disclosure or claims. Accordingly, the above description does not bound the scope of the claims. Further, more than one invention may be disclosed.

Other embodiments are within the scope of the invention. For example, due to the nature of software, functions described above can be implemented using software, hardware, firmware, hardwiring, or combinations of any of these. Features implementing functions may also be physically located at various locations, including being distributed such that portions of functions are implemented at different physical locations.

What is claimed is:

1. A patient support structure for assisting cardiopulmonary resuscitation (CPR) treatment of a patient, the patient support structure comprising:
   a base frame;
   one or more patient support sections wherein at least one of the one or more patient support sections is coupled to and supported by the base frame;
   at least one tilt adjuster coupled to at least one of the one or more patient support sections and configured to:
      communicatively couple with a defibrillator configured to receive sensor data indicative of a phase of CPR treatment,
      receive a control signal indicative of a target tilt angle from the defibrillator, and
      automatically tilt the at least one of the one or more patient support sections, around a transverse axis of the patient support structure, to the target tilt angle in response to the control signal from the defibrillator, wherein the target tilt angle is based at least in part on the phase of CPR treatment determined by the defibrillator from the sensor data indicative of the phase of CPR treatment; and
   a chest compression (CC) device mount disposed on at least one of the one or more patient support sections and configured to adjustably secure a CC device to the patient support structure.

2. The patient support structure of claim 1 wherein the CC device mount is configured to couple to a complementary mounting structure of the CC device.

3. The patient support structure of claim 1 wherein the CC device mount is configured to secure the CC device to the patient support structure without coupling to a complementary mounting structure on the CC device.

4. The patient support structure of claim 1 comprising an alignment feature wherein the alignment feature comprises one or more indicators of a position of an anatomical reference point of the patient that will align the patient with the CC device when the CC device is secured to the patient support structure.

5. The patient support structure of claim 4 wherein the one or more indicators comprise one or more of a bump, a protrusion, a marking, a divot, and a lighted indicator.

6. The patient support structure of claim 1 comprising a manual position adjuster configured for manual adjustment of a position of the CC device relative to the patient support structure.

7. The patient support structure of claim 1 comprising an automated position adjuster configured to automatically adjust a position of the CC device relative to the patient support structure.

8. The patient support structure of claim 7 wherein the automated position adjuster is configured to automatically adjust the position of the CC device in response to the control signal from the defibrillator.

9. The patient support structure of claim 7 wherein the automated position adjuster is configured to automatically adjust the position of the CC device based on an adjustment of the target tilt angle.

10. The patient support structure of claim 1 wherein the target tilt angle is a first tilt angle and the at least one tilt adjuster is configured to adjust the at least on (of the one or more patient support sections to a second tilt angle during the CPR treatment.

11. The patient support structure of claim 1 wherein the one a more patient support sections comprise a first patient support section configured to support an upper body of the patient and the at least one tilt adjuster is configured to tilt the first patient support section to the target tilt angle.

12. The patient support structure of claim 11 comprising one or more angle indicators configured to indicate a current tilt angle.

13. The patient support structure of claim 12 wherein the patient support structure comprises one or more accelerometers and the one or more angle indicators are configured to display angles determined based on an accelerometer signal.

14. The patient support structure of claim 12 wherein the one or more angle indicators are coupled to an alarm configured to emit an alarm signal if the current tilt angle does not correspond to the target tilt angle.

15. The patient support structure of claim 1 comprising:
   two or more patient support sections; and
   a spacer pivotally coupled to the two or more patient support sections and configured to elevate one of the two or more patient support sections relative to another of the two or more patient support sections.

16. The patient support structure of claim 1 wherein the target tilt angle is between approximately 0 and 40 degrees, approximately 0 and 30 degrees, approximately 10 and 30 degrees, approximately 10 and 20 degrees, approximately 20 and 30 degrees, or approximately between 25 and 30 degrees.

17. The patient support structure of claim 1 comprising a user interface and wherein the defibrillator is further configured to provide the target tilt angle to the user interface.

18. The patient support structure of claim 17 wherein the user interface comprises a display configured to display the target tilt angle.

19. The patient support structure of claim 1 wherein the target tilt angle is based on a physiological phase of the patient.

20. The patient support structure of claim 19 wherein the physiological phase of the patient comprises one or more of a return of spontaneous circulation (ROSC) phase, a cardiac event, a respiratory event, an electrical phase, a metabolic phase, and a circulatory phase.

21. The patient support structure of claim 1 wherein the defibrillator is configured to receive the sensor data indicative of the phase of CPR treatment from at least one of a timer, a motion sensor, a pressure sensor, and electrodes.

22. The patient support structure of claim 1 wherein the phase of CPR treatment comprises one or more of an elapsed time of CPR treatment, a number of delivered CPR compressions, a number of delivered CPR ventilations, a number of delivered defibrillation shocks, and an interval within a compression cycle.

23. The patient support structure of claim 1, wherein the target tilt angle is based on physiological sensor input to the defibrillator.

24. The patient support structure of claim 23, wherein the physiological sensor input comprises signals indicative of one or more of cerebral oxygenation, capnography, blood pressure, and blood flow.

25. The patient support structure of claim 1, wherein the one or more patient support sections comprise a first patient support section configured to support a head of the patient and a second patient support section configured to support a torso of the patient.

26. The patient support structure of claim 25, wherein the at least one tilt adjuster is configured to automatically tilt the first patient support section relative to the second patient support section in response to the control signal from the defibrillator.

27. The patient support structure of claim 26, wherein the at least one tilt adjuster is configured to automatically tilt the first patient support section relative to the second patient support section such that the first patient support section is elevated relative to the second patient support section.

28. The patient support structure of claim 1, wherein the at least one tilt adjuster is configured to automatically tilt the at least one of the one or more patient support sections at a rate of angle adjustment based on the control signal from the defibrillator.

29. The patient support structure of claim 1, wherein the target tilt angle comprises a first target tilt angle and wherein the at least one tilt adjuster is configured to automatically tilt the at least one of the one or more patient support sections, around the transverse axis of the patient support structure, based on the control signal from the defibrillator, to a first tilt angle during a first time interval and to a second and different tilt angle during a second time interval during the CPR treatment of the patient.

30. The patient support structure of claim 1, wherein the CC device mount is configured to adjustably secure the CC device to the patient support structure such that the CC device remains aligned with a preferred location on a sternum of the patient during the tilt of the at least one of the one or more patient support sections by the at least one tilt adjuster.

31. The patient support structure of claim 1, wherein the CC device mount is configured to adjustably secure the CC device wherein the CC device comprises a piston-based CC device that includes a suction cup with compression pad.

* * * * *

UNITED STATES PATENT AND TRADEMARK OFFICE
CERTIFICATE OF CORRECTION

PATENT NO. : 11,179,286 B2  
APPLICATION NO. : 15/787735  
DATED : November 23, 2021  
INVENTOR(S) : Gary A. Freeman et al.

Page 1 of 1

It is certified that error appears in the above-identified patent and that said Letters Patent is hereby corrected as shown below:

In the Specification

Column 11, Line 58 - delete "and or", insert -- and/or --
Column 25, Line 5 - delete "pressures", insert -- pressure --
Column 43, Line 55 - delete "components", insert -- components. --

In the Claims

Claim 10, Column 60, Line 31 - delete "on (of", insert -- one of --
Claim 11, Column 60, Line 35 - delete "one a", insert -- one or --

Signed and Sealed this
Fifteenth Day of February, 2022

Drew Hirshfeld
*Performing the Functions and Duties of the*
*Under Secretary of Commerce for Intellectual Property and*
*Director of the United States Patent and Trademark Office*